United States Patent
Kumar et al.

(10) Patent No.: US 8,987,278 B2
(45) Date of Patent: *Mar. 24, 2015

(54) THIENOPYRIMIDINEDIONE DERIVATIVES AS TRPA1 MODULATORS

(71) Applicant: Glenmark Pharmaceuticals S.A., La Chaux-de-Fonds (CH)

(72) Inventors: Sukeerthi Kumar, Navi Mumbai (IN); Abraham Thomas, Navi Mumbai (IN); Nayan Taterao Waghmare, Dist-Pune (IN); Sanjay Margal, Navi Mumbai (IN); Neelima Khairatkar-Joshi, Thane (IN); Indranil Mukhopadhyay, Navi Mumbai (IN)

(73) Assignee: Glenmark Pharmaceuticals S.A., La Chaux-de-Fonds (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/925,975

(22) Filed: Jun. 25, 2013

(65) Prior Publication Data

US 2013/0289054 A1    Oct. 31, 2013

Related U.S. Application Data

(63) Continuation of application No. 12/936,451, filed as application No. PCT/IB2010/000930 on Mar. 23, 2010, now Pat. No. 8,507,503.

(60) Provisional application No. 61/171,355, filed on Apr. 21, 2009, provisional application No. 61/251,994, filed on Oct. 15, 2009, provisional application No. 61/294,470, filed on Jan. 12, 2010.

(30) Foreign Application Priority Data

| Mar. 23, 2009 | (IN) | .......................... 665/MUM/2009 |
| Sep. 23, 2009 | (IN) | .......................... 2213/MUM/2009 |
| Dec. 16, 2009 | (IN) | .......................... 2906/MUM/2009 |

(51) Int. Cl.
*A61K 31/519* (2006.01)
*C07D 495/04* (2006.01)

(52) U.S. Cl.
CPC .................. *C07D 495/04* (2013.01)
USPC ....................... 514/260.1; 544/278

(58) Field of Classification Search
USPC ....................... 514/260.1; 544/278
See application file for complete search history.

(56) References Cited

U.S. PATENT DOCUMENTS

| 6,028,074 | A | 2/2000 | Cheshire et al. |
| 7,465,581 | B2 | 12/2008 | Bevan et al. |
| 2004/0038994 | A1 | 2/2004 | Wilson |
| 2004/0122028 | A1 | 6/2004 | Ingall et al. |
| 2005/0070558 | A1 | 3/2005 | Vidan Juan et al. |
| 2007/0032531 | A1 | 2/2007 | Smith et al. |
| 2007/0099940 | A1 | 5/2007 | Spearing |
| 2007/0105920 | A1 | 5/2007 | Palin et al. |
| 2007/0196866 | A1 | 8/2007 | Patapoutian et al. |
| 2009/0062258 | A1 | 3/2009 | Hamamura et al. |
| 2009/0143377 | A1 | 6/2009 | Ng et al. |
| 2009/0233907 | A1 | 9/2009 | Austin et al. |
| 2009/0325987 | A1 | 12/2009 | Muthuppalniappan et al. |
| 2011/0009430 | A1 | 1/2011 | Moran et al. |

FOREIGN PATENT DOCUMENTS

| EP | 1657238 A1 | 5/2006 |
| GB | 1445697 | 8/1976 |
| WO | 2008/094909 A2 | 8/2008 |
| WO | 2009/158719 A2 | 12/2009 |

OTHER PUBLICATIONS

MacPherson et al., "Noxious compounds activate TRPA1 ion channels through covalent modification of cysteines", Nature, Feb. 2007, pp. 541-545, vol. 445, Nature Publishing Group.
L. Carroll King and Robert J. Hlavacek, "The Reaction of Ketones with Iodine and Thiourea", J. Am. Chem. Soc., Aug. 1950, pp. 3722-3725, vol. 72.
G. F. Duffin and J. D. Kendall, "The Reaction of Diazonium Salts with 1-Aryl-Δ2-pyrazolines", J. Chem. Soc., 1954, pp. 408-415.
H. Egg and I. Volgger, "A Convenient Synthesis of 1,3 Dialkyl-6-methyluracils and 1,3-Dialkyl-6-ethylthymines", Synthesis, Dec. 1982, pp. 1071-1073, Georg Thieme Verlag, Stuttgart, New York.
Satyanarayana et al., "Cycloaromatization of α-Oxoketene Dithioacetals with Enaminone Derived Carbanions", Tetrahedron Letters, 1992, pp. 6173-6176, vol. 33—issue No. 41, Pergamon Press Ltd.
Hirota et al., "Convenient Synthesis of Pyrido[4,3-d]Pyrimidine-2,4-(1H,3H)-Diones", Heterocycles, 1998, pp. 871-882, vol. 47-issue No. 2.

(Continued)

*Primary Examiner* — Samantha Shterengarts
(74) *Attorney, Agent, or Firm* — Pergament Gilman & Cepeda LLP; Milagros A. Cepeda; Edward D. Pergament

(57) ABSTRACT

The present invention is related to novel thienopyrimidinedione derivatives as TRPA (Transient Receptor Potential subfamily A) modulators. In particular, compounds described herein are useful for treating or preventing diseases, conditions and/or disorders modulated by TRPA1 (Transient Receptor Potential subfamily A, member 1). Also provided herein are processes for preparing compounds described herein, intermediates used in their synthesis, pharmaceutical compositions thereof, and methods for treating or preventing diseases, conditions and/or disorders modulated by TRPA1.

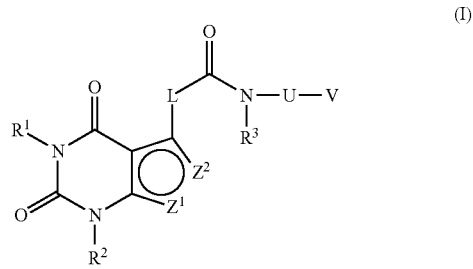

(I)

29 Claims, No Drawings

(56) References Cited

OTHER PUBLICATIONS

Stephen B. McMahon and John N. Wood, "Increasingly Irritable and Close to Tears: TRPA1 in Inflammatory Pain", Cell, Mar. 24, 2006, pp. 1123-1125, vol. 124, Elsevier Inc.
Senda et al., "Pyrimidine Derivatives and Related Compounds. XII. The Vilsmeier Reaction of Barbituric Acid Derivatives and Uracil Derivatives", Yakugaku Zasshi, 1971, pp. 1372-1376, vol. 91-issue No. 12.
Dipak Prajapati and Jagir Singh Sandhu, "Studies on Pyrimidine-Annelated Heterocyles; 8 Intramolecular Cycloaddition of Thiophene and Nitrile Oxide or Nitrone Groups Bonded to 1,3-Dimethyluracils", Synthesis, Apr. 1988, pp. 342-344.
Richard B. Silverman and Michael P. Groziak, "Model Chemistry for a Covalent Mechanism of Action of Orotidine 5'-Phosphate Decarboxylase", J. Am. Chem. Soc., 1982, pp. 6434-6439, vol. 104-issue No. 23, American Chemical Society.
Story et al., "ANKTM1, a TRP-like Channel Expressed in Nociceptive Neurons, Is Activated by Cold Temperatures", Cell, Mar. 21, 2003, pp. 819-829, vol. 112, Cell Press.
Thomas L. Little and Stephen E. Webber, "A Simple and Practical Synthesis of 2-Aminoimidazoles", J. Org. Chem.,1994, pp. 7299-7305, vol. 59, American Chemical Society.
Tormyshev et al., "Aryl Alkyl Ketones in a One-Pot Gewald Synthesis of 2-Aminothiophenes", Synlett, 2006, pp. 2559-2564, issue No. 16, Thieme Stuttgart, New York.
Voorhoeve et al., "A Genetic Screen Implicates miRNA-372 and miRNA-373 As Oncogenes in Testicular Germ Cell Tumors", Cell, Mar. 24, 2006, pp. 1169-1181, vol. 124, Elsevier Inc.
Wissenbach et al., "TRP channels as potential drug targets", Biology of the Cell, 2004, pp. 47-54, vol. 96, Elsevier SAS.
Hirota et al., "Pyrimidines. 65 [1]. Synthesis of 6-Substituted Thieno[2,3-d]pyrimidine-2,4(1H,3H)-diones", J. Heterocyclic Chem., Mar.-Apr. 1990, pp. 717-721, vol. 27.
Kotha et al., "A Simple Synthetic Approach to Allylated Aromatics via the Suzuki-Miyaura Cross-Coupling Reaction", Synlett, 2005, pp. 1877-1880, issue No. 12, Thieme Stuttgart, New York.
Kennis et al., "New 2-Substituted 1,2,3,4-Tetrahydrobenzofuro[3,2-c]pyridine Having Highly Active and Potent Central α2-Antagonistic Activity as Potential Antidepressants", Bioorganic & Medicinal Chemistry Letters, 2000, pp. 71-74, vol. 10, Elsevier Science Ltd.
Mashraqui et al., "Dipyridyl/pyridinium thieno[2,3-b]thiophenes as new atropisomeric systems. Synthesis, conformational analysis and energy minimization", Tetrahedron, 2005, pp. 3507-3513, vol. 61, Elsevier Ltd.
Mohler et al., "A Facile Synthesis of Homologous 4,4'-Dialkanoic Acid Substituted 2,2'-Bipyridines", Synthesis, 2002, pp. 745-748, issue No. 6, Thieme Stuttgart, New York.
He et al., "Conformational Color Polymorphism and Control of Crystallization of 5-Methyl-2-[(4-methyl-2-nitrophenyl) amino]-3-thiophenecarbonitrile", Journal of Pharmaceutical Sciences, Mar. 2001, pp. 371-388, vol. 90-issue No. 3, Wiley-Liss, Inc. and the American Pharmaceutical Association.
Prakash et al., "N-Halosuccinimide/BF3-H2O, Efficient Electrophilic Halogenating Systems for Aromatics", J. Am. Chem. Soc., 2004, pp. 15770-15776, vol. 126-issue No. 48, American Chemical Society.
Postema et al., "Synthesis and Partial Biological Evaluation of a Small Library of Differentially-Linked β-C Disaccharides", J. Org. Chem., 2003, pp. 4748-4754, vol. 68-issue No. 12, American Chemical Society.
Tsupak et al., "Pyrrolopyrimidines. 5. Reaction of 6-Amino-1,3-Dimethylpyrrolo[3,4-d]Pyrimidine-2,4(1H,3H)-Diones With 1,3-Diketones", Chemistry of Heterocyclic Compounds, 2003, pp. 953-959, vol. 39-issue No. 7, Plenum Publishing Corporation.
Samir J. Naik and Uma P. Halkar, "Synthesis and application of novel 4,5,6,7-tetrahydrobenzothiazole based azo disperse dyes", Arkivoc, 2005, pp. 141-149, vol. xiii, Arkat USA, Inc.
Toth et al., "Arachidonyl dopamine as a ligand for the vanilloid receptor VR1 of the rat", Life Sciences, 2003, pp. 487-498, vol. 73, Elsevier Science Inc.
McNamara et al., "TRPA1 mediates formalin-induced pain", PNAS, Aug. 14, 2007, pp. 13525-13530, vol. 104-issue No. 33, The National Academy of Sciences of the USA.
Press et al., "Furo[3,4-d]pyrimidine-2,4-dione derivatives with antihypertensive activity. Analogues of thienopyrimidine-2,4-diones", Eur. J. Med. Chem., 1989, pp. 627-630, vol. 24, Elsevier, Paris.
Sladowska et al., "Synthesis and pharmacological properties of N, N-dialkyl(dialkenyl)amides of 7-methyl-3-phenyl-1-[2-hydroxy-3-(4-phenyly-1-piperazinyl)propy1]-2-4-dioxo-1,2,3,4-tetrahydropyrido-[2,3-d]pyrimidine-5-carboxylic acid", Farmaco, Jan. 2003, pp. 25-32, vol. 58-issue No. 1, Elsevier SAS.
Childers et al., "Advances in the development of novel analgesics", Expert Opin. Ther. Patents, Sep. 1, 2008, pp. 1027-1067, vol. 18-issue No. 9, Informa UK Ltd.
International Search Report and Written Opinion dated Oct. 6, 2010 for International Patent Application No. PCT/IB2010/000930.
International Search Report and Written Opinion dated Jun. 28, 2010 for International Patent Application No. PCT/IB2010/000834.
International Search Report and Written Opinion dated Jun. 28, 2010 for International Patent Application No. PCT/IB2010/000840.
International Search Report and Written Opinion dated Sep. 20, 2010 for International Patent Application No. PCT/IB2010/001073.
International Search Report dated Aug. 26, 2010 for International Patent Application No. PCT/IB2010/000553.
Supplemental European Search Report dated Jun. 25, 2012 for EP10755503.
Extended European Search Report dated Jul. 4, 2013 for corresponding European Application No. EP 13 00 2731.
Non-Final Office Action mailed by the USPTO on Nov. 5, 2012, for U.S. Appl. No. 12/936,451.

THIENOPYRIMIDINEDIONE DERIVATIVES AS TRPA1 MODULATORS

RELATED APPLICATIONS

This Application is a Continuation of U.S. patent application Ser. No. 12/936,451 filed Oct. 5, 2010, which is a National Stage Application under 35 U.S.C. 371 of PCT International application No. PCT/IB2010/000930, filed Mar. 23, 2010, which claims priority to Indian Patent Application Nos. 665/MUM/2009 filed on Mar. 23, 2009; 2213/MUM/2009 filed on Sep. 23, 2009; 2906/MUM/2009 filed on Dec. 16, 2009; and US Provisional Application Nos. 61/171,355 filed on Apr. 21, 2009; 61/251,994 filed on Oct. 15, 2009 and 61/294,470 filed on Jan. 12, 2010, all of which are hereby incorporated by reference in their entireties.

TECHNICAL FIELD

The present patent application relates to thienopyrimidinedione derivative as TRPA1 modulators with transient receptor potential ankyrinl (TRPA1) activity.

BACKGROUND OF THE INVENTION

The transient receptor potential (TRP) channels or receptors are pain receptors. They have been classified into seven subfamilies: TRPC (canonical), TRPV (vanilloid), TRPM (melastatin), TRPP (polycystin), TRPML (mucolipin), TRPA (ankyrin, ANKTM1) and TRPN(NOMPC) families. The TRPC family can be divided into 4 subfamilies (i) TRPC1 (ii) TRPC2 (iii) TRPC3, TRPC6, TRPC7 and (iv) TRPC4, TRPC5 based on sequence functional similarities. Currently the TRPV family has 6 members. TRPV5 and TRPV6 are more closely related to each other than to TRPV1, TRPV2, TRPV3 or TRPV4. TRPA1 is most closely related to TRPV3 and is more closely related to TRPV1 and TRPV2 than to TRPV5 and TRPV6. The TRPM family has 8 members. Constituents include the following: the founding member TRPM1 (melastatin or LTRPC1), TRPM3 (KIAA1616 or LTRPC3), TRPM7 (TRP-PLIK, ChaK(1), LTRPC7), TRPM6 (ChaK2), TRPM2 (TRPC7 or LTRPC2), TRPM8 (TRP-p8 or CMR1), TRPM5 (MTR1 or LTRPC5) and TRPM4 (FLJ20041 or LTRPC4). The TRPML family consists of the mucolipins, which include TRPML1 (mucolipin 1), TRPML2 (mucolipin 2) and TRPML3 (mucolipin 3). The TRPP family consists of two groups of channels: those predicted to have six transmembrane domains and those that have eleven. TRPP2 (PKD2), TRPP3 (PKD2L1), TRPP5 (PKD2L2) are all predicted to have six transmembrane domains. TRPP1 (PKD1, PC1), PKD-REJ and PKD-1L1 are all thought to have eleven transmembrane domains. The sole mammalian member of the TRPA family is ANKTM1.

It is believed TRPA1 is expressed in nociceptive neurons. Nociceptive neurons of the nervous system sense the peripheral damage and transmit pain signals. TRPA1 is membrane bound and most likely acts as a heterodimeric voltage gated channel. It is believed to have a particular secondary structure, its N-terminus is lined with a large number of ankyrin repeats which are believed to form a spring-like edifice. TRPA1 is activated by a variety of noxious stimuli, including cold temperatures (activated at 17° C.), pungent natural compounds (e.g., mustard, cinnamon and garlic) and environmental irritants (MacPherson L J et al, Nature, 2007, 445; 541-545). Noxious compounds activate TRPA1 ion channels through covalent modification of cysteines to form covalently linked adducts. Variety of endogenous molecules produced during tissue inflammation/injury have been identified as pathological activators of TRPA1 receptor. These include hydrogen peroxide which is produced due to oxidative stress generated during inflammation, alkenyl aldehyde 4-HNE—an intracellular lipid peroxidation product and cyclopentenone prostaglandin 15dPGJ2 which is produced from PGD2 during inflammation/allergic response. TRPA1 is also activated in receptor dependant fashion by Bradykinin (BK) which is released during tissue injury at peripheral terminals The difference between TRPA1 and other TRP receptors is that TRPA1 ligand binding persists for hours due to which the physiological response (e.g., pain) is greatly prolonged. Hence to dissociate the electrophile, an effective antagonist is required.

WO 2009/158719, WO 2009/002933, WO 2008/0949099, WO 2007/073505, WO 2004/055054 and WO 2005/089206 describe the TRP channels as the targets for the treatment of pain and related conditions.

In efforts to discover better analgesics for the treatment of both acute and chronic pain and to develop treatments for various neuropathic and nociceptive pain states, there exists a need for a more effective and safe therapeutic treatment of diseases, conditions and/or disorders modulated by TRPA1.

SUMMARY OF THE INVENTION

The present invention relates to compounds of the formula (I):

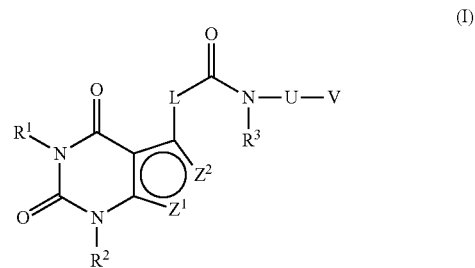

or a pharmaceutically acceptable salt thereof,
wherein, $R^1$ and $R^2$, which may be the same or different, are independently selected from hydrogen, substituted or unsubstituted alkyl, haloalkyl, alkenyl, alkynyl, cycloalkyl, cycloalkylalkyl, arylalkyl, $(CR^xR^y)_nOR^x$, $COR^x$, $COOR^x$, $CONR^xR^y$, $(CH_2)_nNR^xR^y$, $(CH_2)_nCHR^xR^y$ and $(CH_2)_nNHCOR^x$;

$R^3$ is selected from hydrogen, substituted or unsubstituted alkyl, alkenyl, alkynyl, cycloalkyl, cycloalkylalkyl, cycloalkenyl;

L is a linker selected from $—(CR^xR^y)_n—$, $—O—(CR^xR^y)_n—$, $—C(O)—$, $—NR^x—$, $—S(O)_mNR^x—$, $—NR^x(CR^xR^y)_n—$ and $—S(O)_mNR^x(CR^xR^y)_n$;

$Z_1$ and $Z_2$ are independently sulfur or $CR^a$; with a proviso that one of $Z_1$ or $Z_2$ is always sulfur and other is $CR^a$;

$R^a$ is selected from hydrogen, cyano, halogen, substituted or unsubstituted alkyl, haloalkyl, alkenyl, alkynyl, cycloalkyl, cycloalkylalkyl, $OR^x$, $(CR^xR^y)_nOR^x$, $COR^x$, $COOR^x$, $CONR^xR^y$, $S(O)_mNR^xR^y$, $NR^xR^y$, $NR^x(CR^xR^y)_nOR^x$, $(CH_2)_nNR^xR^y$, $(CH_2)_nCHR^xR^y$, $NR^x(CR^xR^y)_nCONR^xR^y$, $(CH_2)_nNHCOR^x$, $(CH_2)_nNH(CH_2)_nSO_2R^x$, $(CH_2)_nNHSO_2R^x$, $SR^x$ and $OR^x$;

U is selected from substituted or unsubstituted aryl, substituted or unsubstituted five membered heterocycles selected from the group consisting of thiazole, isothiazole, oxazole, isoxazole, thiadiazole, oxadiazole, pyrazole, imidazole, furan, thiophene, pyrroles, 1,2,3-triazoles, and 1,2,4-triazole, or substituted or unsubstituted six membered heterocycle selected from the group consisting of pyrimidine, pyridine and pyridazine;

V is selected from hydrogen, cyano, nitro, —NR$^x$R$^y$, halogen, hydroxyl, substituted or unsubstituted alkyl, alkenyl, alkynyl, cycloalkyl, cycloalkylalkyl, cycloalkenyl, haloalkyl, haloalkoxy, cycloalkylalkoxy, aryl, arylalkyl, biaryl, heteroaryl, heteroarylalkyl, heterocyclic ring and heterocyclylalkyl, —C(O)OR$^x$, —OR$^x$, —C(O)NR$^x$R$^y$, —C(O)R$^x$, and —SO$_2$NR$^x$R$^y$; or U and V together may form an optionally substituted 3 to 7 membered saturated or unsaturated cyclic ring that may optionally include one or more heteroatoms selected from O, S and N;

at each occurrence, R$^x$ and R$^y$ are independently selected from hydrogen, hydroxyl, halogen, substituted or unsubstituted alkyl, alkenyl, alkynyl, cycloalkyl, cycloalkylalkyl, cycloalkenyl, aryl, arylalkyl, heteroaryl, heteroarylalkyl, heterocyclic ring and heterocyclylalkyl; and at each occurrence, 'm' and 'n' are independently selected from 0 to 2, both inclusive.

According to one embodiment, there is provided a compound of the formula (Ia):

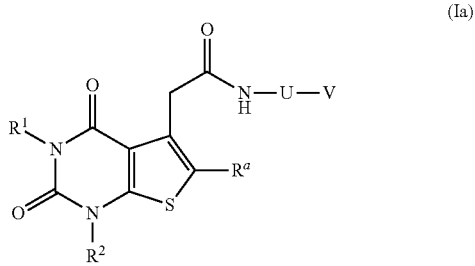

(Ia)

or a pharmaceutically acceptable salt thereof, wherein,

R$^1$ and R$^2$, which may be the same or different, are independently selected from hydrogen, substituted or unsubstituted alkyl, haloalkyl, alkenyl, alkynyl, cycloalkyl, cycloalkylalkyl, arylalkyl, (CR$^x$R$^y$)$_n$OR$^x$, COR$^x$, COOR$^x$, CONR$^x$R$^y$, (CH$_2$)$_n$NR$^x$R$^y$, (CH$_2$)$_n$CHR$^x$R$^y$ and (CH$_2$)$_n$NHCOR$^x$;

R$^a$ is selected from hydrogen, cyano, halogen, substituted or unsubstituted alkyl, haloalkyl, alkenyl, alkynyl, cycloalkyl, cycloalkylalkyl, OR$^x$, (CR$^x$R$^y$)$_n$OR$^x$, COR$^x$, COOR$^x$, CONR$^x$R$^y$, S(O)$_m$NR$^x$R$^y$, NR$^x$R$^y$, NR$^x$(CR$^x$R$^y$)$_n$OR$^x$, (CH$_2$)$_n$NR$^x$R$^y$, (CH$_2$)$_n$CHR$^x$R$^y$, NR$^x$(CR$^x$R$^y$)$_n$CONR$^x$R$^y$, (CH$_2$)$_n$NHCOR$^x$, (CH$_2$)$_n$NH(CH$_2$)$_n$SO$_2$R$^x$, (CH$_2$)$_n$NHSO$_2$R$^x$, SR$^x$ and OR$^x$;

U is selected from substituted or unsubstituted aryl, substituted or unsubstituted five membered heterocycles selected from the group consisting of thiazole, isothiazole, oxazole, isoxazole, thiadiazole, oxadiazole, pyrazole, imidazole, furan, thiophene, pyrroles, 1,2,3-triazoles, and 1,2,4-triazole, or substituted or unsubstituted six membered heterocycle selected from the group consisting of pyrimidine, pyridine and pyridazine;

V is selected from hydrogen, cyano, nitro, —NR$^x$R$^y$, halogen, hydroxyl, substituted or unsubstituted alkyl, alkenyl, alkynyl, cycloalkyl, cycloalkylalkyl, cycloalkenyl, haloalkyl, haloalkoxy, cycloalkylalkoxy, aryl, arylalkyl, biaryl, heteroaryl, heteroarylalkyl, heterocyclic ring and heterocyclylalkyl, —C(O)OR$^x$, —OR$^x$, —C(O)NR$^x$R$^y$, —C(O)R$^x$, and —SO$_2$NR$^x$R$^y$; or U and V together may form an optionally substituted 3 to 7 membered saturated or unsaturated cyclic ring that may optionally include one or more heteroatoms selected from O, S and N;

at each occurrence, R$^x$ and R$^y$ are independently selected from hydrogen, hydroxyl, halogen, substituted or unsubstituted alkyl, alkenyl, alkynyl, cycloalkyl, cycloalkylalkyl, cycloalkenyl, aryl, arylalkyl, heteroaryl, heteroarylalkyl, heterocyclic ring and heterocyclylalkyl; and at each occurrence, 'm' and 'n' are independently selected from 0 to 2, both inclusive.

The embodiments below are illustrative of the present invention and are not intended to limit the claims to the specific embodiments exemplified.

According to one embodiment, specifically provided are compounds of the formula (Ia) in which R$^a$ is hydrogen or (C$_1$-C$_4$) alkyl.

According to another embodiment, specifically provided are compounds of the formula (Ia) in which R$^1$ and R$^2$ are (C$_1$-C$_4$) alkyl, preferably methyl.

According to yet another embodiment, specifically provided are compounds of the formula (Ia) in which 'U' is substituted or unsubstituted five membered heterocycle, preferably thiazole, imidazole, isoxazole, pyrazole or thiadiazole.

According to yet another embodiment, specifically provided are compounds of the formula (Ia) in which 'U' is substituted or unsubstituted six membered heterocycle, preferably pyrimidine.

According to yet another embodiment, specifically provided are compounds of the formula (Ia) in which 'V' is substituted or unsubstituted aryl, preferably phenyl. In this embodiment the substituents on phenyl may be one or more and are independently selected from halogen (for example F, Cl or Br), cyano, alkyl (for example t-butyl), haloalkyl (for example CF$_3$), and haloalkoxy (for example OCHF$_2$, OCF$_3$, OCH$_2$CF$_3$, or OCH$_2$CH$_2$CF$_3$).

According to one embodiment, there is provided a compound of the formula (Ib):

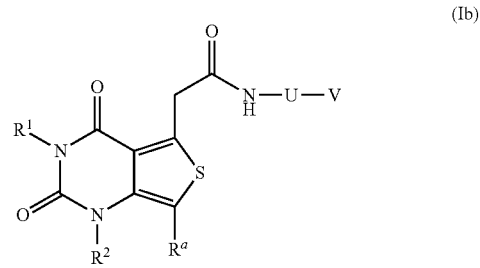

(Ib)

or a pharmaceutically acceptable salt thereof, wherein,

U, V, R$^1$, R$^2$ and R$^a$ are as defined above.

The embodiments below are illustrative of the present invention and are not intended to limit the claims to the specific embodiments exemplified.

According to one embodiment, specifically provided are compounds of the formula (Ib) in which $R^a$ is hydrogen.

According to another embodiment, specifically provided are compounds of the formula (Ib) in which $R^1$ and $R^2$ are methyl.

According to yet another embodiment, specifically provided are compounds of the formula (Ib) in which 'U' is substituted or unsubstituted five membered heterocycle, preferably thiazole.

According to yet another embodiment, specifically provided are compounds of the formula (Ib) in which 'V' is substituted or unsubstituted aryl, preferably phenyl. In this embodiment the substituents on phenyl may be one or more and are independently selected from halogen (for example F, Cl or Br), alkyl ($CH_2CH(CH_3)_2$), haloalkyl (for example $CF_3$), and haloalkoxy (for example $OCHF_2$, $OCF_3$ or $OCH_2CF_3$).

According to one embodiment, there is provided a compound of the formula (Ic):

(Ic)

or a pharmaceutically-acceptable salt thereof.

wherein, $R^1$, $R^2$ and $R^a$, which may be the same or different, are each independently hydrogen or ($C_1$-$C_4$)alkyl;

$R^4$, $R^5$, $R^6$, $R^7$, $R^8$ and $R^9$, which may be same or different, are each independently selected from the group comprising of hydrogen, halogen, cyano, hydroxyl, nitro, amino, substituted or unsubstituted alkyl, alkoxy, haloalkyl, haloalkoxy, cycloalkyl, cycloalkylalkyl, cycloalkenyl, cycloalkylalkoxy, aryl, arylalkyl, biaryl, heteroaryl, heteroarylalkyl, heterocyclic ring and heterocyclylalkyl.

The embodiments below are illustrative of the present invention and are not intended to limit the claims to the specific embodiments exemplified.

According to one embodiment, specifically provided are compounds of the formula (Ic) in which $R^1$ and $R^2$ are methyl.

According to another embodiment, specifically provided are compounds of the formula (Ic) in which $R^4$, $R^5$, $R^6$ and $R^7$ are independently selected from hydrogen, fluoro, trifluoromethyl or trifluoromethoxy.

According yet another embodiment, specifically provided are compounds of the formula (Ic) in which $R^8$ is hydrogen.

According yet another embodiment, specifically provided are compounds of the formula (Ic) in which $R^9$ is hydrogen.

According to one embodiment, there is provided a compound of the formula (Id):

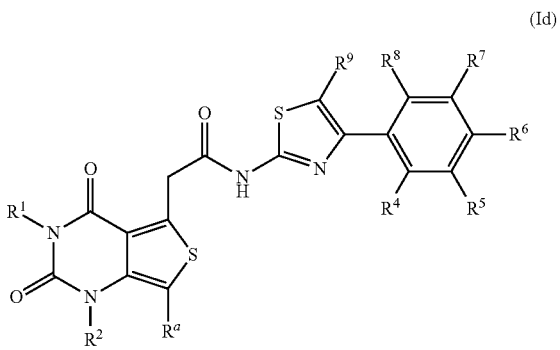

(Id)

or a pharmaceutically-acceptable salt thereof.

wherein, $R^1$, $R^2$, and $R^a$, which may be the same or different, are each independently hydrogen or ($C_1$-$C_4$)alkyl;

$R^4$, $R^5$, $R^6$, $R^7$, $R^8$ and $R^9$, which may be same or different, are each independently selected from the group comprising of hydrogen, halogen, cyano, hydroxyl, nitro, amino, substituted or unsubstituted alkyl, alkoxy, haloalkyl, haloalkoxy, cycloalkyl, cycloalkylalkyl, cycloalkenyl, cycloalkylalkoxy, aryl, arylalkyl, biaryl, heteroaryl, heteroarylalkyl, heterocyclic ring and heterocyclylalkyl.

The embodiments below are illustrative of the present invention and are not intended to limit the claims to the specific embodiments exemplified.

According to one embodiment, specifically provided are compounds of the formula (Id) in which $R^1$ and $R^2$ are methyl.

According to another embodiment, specifically provided are compounds of the formula (Id) in which $R^4$, $R^5$, $R^6$ and $R^7$ are independently selected from hydrogen, fluoro, trifluoromethyl or trifluoromethoxy.

According yet another embodiment, specifically provided are compounds of the formula (Id) in which $R^8$ is hydrogen.

According yet another embodiment, specifically provided are compounds of the formula (Id) in which $R^9$ is hydrogen.

It should be understood that the formulas (I), (Ia), (Ib), (Ic) and (Id) structurally encompasses all stereoisomers, enantiomers and diastereomers, and pharmaceutically acceptable salts that may be contemplated from the chemical structure of the genera described herein.

Particularly contemplated are compounds of the formulas (I), (Ia), (Ib), (Ic) and (Id), which possess human $IC_{50}$ of less than 250 nM, preferably, less than 100 nM, more preferably, less than 50 nM with respect to TRPA1 activity as measured by method as described in the present patent application.

The compound of the present invention as TRPA1 modulator is used herein because it is more selective for one TRP isoform than others, e.g., 2-fold, 5-fold, 10-fold, and more preferably at least 20, 40, 50, 60, 70, 80, or at least 100- or even 1000-fold more selective for TRPA1 over one or more of TRPC6, TRPV5, TRPV6, TRPM8, TRPV1, TRPV2, TRPV4, and/or TRPV3.

In accordance with another aspect, the present patent application provides a pharmaceutical composition that includes at least one compound described herein and at least one pharmaceutically acceptable excipient (such as a pharmaceutically acceptable carrier or diluent). Preferably, the pharmaceutical composition comprises a therapeutically effective amount of at least one compound described herein. The compounds described in the present patent application may be associated with a pharmaceutically acceptable excipient (such as a carrier or a diluent) or be diluted by a carrier, or enclosed within a carrier which can be in the form of a capsule, sachet, paper or other container.

The compounds of the present invention can be administered as pharmaceutical composition containing, for example, 0.1 to 99.5% (more preferably, 0.5 to 90%) of active ingredient in combination with a pharmaceutically acceptable carrier. The ultimate dose will depend on the condition being treated, the route of administration and the age, weight and condition of the patient and will be the doctor's discretion.

Compounds of the present invention may be used in the manufacture of medicaments for the treatment of any diseases disclosed herein. The compounds and pharmaceutical compositions described herein are useful for modulating TRPA1 receptors, wherein modulation is believed to be related to a variety of disease states.

The compound of the present invention can be administered alone or in combination with other therapeutic agents. For instance, the TRPA1 modulator is administered conjointly with one or more of an anti-inflammatory agent, anti-acne agent, anti-wrinkle agent, anti-scarring agent, anti-psoriatic agent, anti-proliferative agent, anti-fungal agent, anti-viral agent, anti-septic agent, anti-migraine agent, keratolytic agent, or a hair growth inhibitor In accordance with another aspect, the present patent application further provides a method of inhibiting TRPA1 receptors in a subject in need thereof by administering to the subject one or more compounds described herein in the amount effective to cause inhibition of such receptor.

DETAILED DESCRIPTION OF THE INVENTION

Definitions

The terms "halogen" or "halo" includes fluorine, chlorine, bromine or iodine.

The term "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl and 1,1-dimethylethyl (tert-butyl). The term "$C_{1-6}$alkyl" refers to an alkyl chain having 1 to 6 carbon atoms. Unless set forth or recited to the contrary, all alkyl groups described herein may be straight chain or branched, substituted or unsubstituted.

The term "alkenyl" refers to an aliphatic hydrocarbon group containing a carbon-carbon double bond and which may be a straight or branched chain having 2 to about 10 carbon atoms, e.g., ethenyl, 1-propenyl, 2-propenyl (allyl), iso-propenyl, 2-methyl-1-propenyl, 1-butenyl and 2-butenyl. Unless set forth or recited to the contrary, all alkenyl groups described herein may be straight chain or branched, substituted or unsubstituted.

The term "alkynyl" refers to a straight or branched chain hydrocarbyl radical having at least one carbon-carbon triple bond and having 2 to about 12 carbon atoms (with radicals having 2 to about 10 carbon atoms being preferred) e.g., ethynyl, propynyl and butynyl. Unless set forth or recited to the contrary, all alkynyl groups described herein may be straight chain or branched, substituted or unsubstituted.

The term "alkoxy" refers to a straight or branched, saturated aliphatic hydrocarbon radical bonded to an oxygen atom that is attached to a core structure. Examples of alkoxy groups include but are not limited to methoxy, ethoxy, propoxy, isopropoxy, butoxy, isobutoxy, tert-butoxy, pentoxy, 3-methyl butoxy and the like. Unless set forth or recited to the contrary, all alkoxy groups described herein may be straight chain or branched, substituted or unsubstituted.

The term "haloalkyl" and "haloalkoxy" means alkyl or alkoxy, as the case may be, substituted with one or more halogen atoms, where alkyl and alkoxy groups are as defined above. The term "halo" is used herein interchangeably with the term "halogen" means F, Cl, Br or I. Examples of "haloalkyl" include but are not limited to trifluoromethyl, difluoromethyl, 2,2,2-trifluoroethyl, pentafluoroethyl, pentachloroethyl 4,4,4-trifluorobutyl, 4,4-difluorocyclohexyl, chloromethyl, dichloromethyl, trichloromethyl, 1-bromoethyl and the like. Examples of "haloalkoxy" include but are not limited to fluoromethoxy, difluoromethoxy, trifluoromethoxy, 2,2,2-trifluoroethoxy, pentafluoroethoxy, pentachloroethoxy, chloromethoxy, dichlorormethoxy, trichloromethoxy, 1-bromoethoxy and the like. Unless set forth or recited to the contrary, all "haloalkyl" and "haloalkoxy" groups described herein may be straight chain or branched, substituted or unsubstituted.

The term "cycloalkyl" denotes a non-aromatic mono or multicyclic ring system of 3 to about 12 carbon atoms, such as cyclopropyl, cyclobutyl, cyclopentyl and cyclohexyl. Examples of multicyclic cycloalkyl groups include, but are not limited to, perhydronapthyl, adamantyl and norbornyl groups, bridged cyclic groups or sprirobicyclic groups, e.g., spiro(4,4) non-2-yl. Unless set forth or recited to the contrary, all cycloalkyl groups described herein may be substituted or unsubstituted.

The term "cycloalkylalkyl" refers to a cyclic ring-containing radical having 3 to about 8 carbon atoms directly attached to an alkyl group. The cycloalkylalkyl group may be attached to the main structure at any carbon atom in the alkyl group that results in the creation of a stable structure. Non-limiting examples of such groups include cyclopropylmethyl, cyclobutylethyl and cyclopentylethyl. Unless set forth or recited to the contrary, all cycloalkylalkyl groups described herein may be substituted or unsubstituted.

The term "cycloalkylalkoxy" is used to denote alkoxy substituted with cycloalkyl, wherein 'alkoxy' and 'cycloalkyl' are as defined above (either in the broadest aspect or a preferred aspect). Examples of cycloalkylalkoxy groups include cyclopropylmethoxy, 1- or 2-cyclopropylethoxy, 1-, 2- or 3-cyclopropylpropoxy, 1-, 2-, 3- or 4-cyclopropyl-butoxy, cyclobutylmethoxy, 1- or 2-cyclobutylethoxy, 1-, 2- or 3-cyclobutylpropoxy, 1-, 2-, 3- or 4-cyclobutylbutoxy, cyclopentylmethoxy, 1- or 2-cyclopentylethoxy, 1-, 2- or 3-cyclopentylpropoxy, 1-, 2-, 3- or 4-cyclopentylbutoxy, cyclohexylmethoxy, 1- or 2-cyclohexylethoxy and 1-, 2- or 3-cyclohexylpropoxy. Preferably, 'cycloalkylalkoxy' is ($C_{3-6}$)cycloalkyl-($C_{1-6}$)alkoxy. Unless set forth or recited to the contrary, all cycloalkylalkoxy groups described herein may be substituted or unsubstituted.

The term "cycloalkenyl" refers to a cyclic ring-containing radical having 3 to about 8 carbon atoms with at least one carbon-carbon double bond, such as cyclopropenyl, cyclobutenyl and cyclopentenyl. Unless set forth or recited to the contrary, all cycloalkenyl groups described herein may be substituted or unsubstituted.

The term "aryl" means a carbocyclic aromatic system containing one, two or three rings wherein such rings may be fused. If the rings are fused, one of the rings must be fully unsaturated and the fused ring(s) may be fully saturated, partially unsaturated or fully unsaturated. The term "fused" means that a second ring is present (ie, attached or formed) by having two adjacent atoms in common (i.e., shared) with the first ring. The term "fused" is equivalent to the term "condensed". The term "aryl" embraces aromatic radicals such as phenyl, naphthyl, tetrahydronaphthyl, indane and biphenyl. Unless set forth or recited to the contrary, all aryl groups described herein may be substituted or unsubstituted.

The term "arylalkyl" refers to an aryl group as defined above directly bonded to an alkyl group as defined above, e.g., —$CH_2C_6H_5$ or —$C_2H_4C_6H_5$. Unless set forth or recited to the contrary, all arylalkyl groups described herein may be substituted or unsubstituted.

The term "heterocyclic ring" refers to a stable 3- to 15-membered ring radical which consists of carbon atoms and from one to five heteroatoms selected from nitrogen, phosphorus, oxygen and sulfur. For purposes of this invention, the heterocyclic ring radical may be a monocyclic, bicyclic or tricyclic ring system, which may include fused, bridged or spiro ring systems and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heterocyclic or heteroaryl). Examples of such heterocyclic ring radicals include, but are not limited to, azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazolyl, imidazolyl, tetrahydroisoqinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxazolidinyl, triazolyl, indanyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofuryl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl and isochromanyl. The heterocyclic ring radical may be attached to the main structure at any heteroatom or carbon atom that results in the creation of a stable structure. Unless set forth or recited to the contrary, all heterocyclic ring described herein may be substituted or unsubstituted.

The term "heterocyclyl" refers to a heterocyclic ring radical as defined above. The heterocyclyl ring radical may be attached to the main structure at any heteroatom or carbon atom that results in the creation of a stable structure. Unless set forth or recited to the contrary, all heterocyclyl groups described herein may be substituted or unsubstituted.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure. Unless set forth or recited to the contrary, all heterocyclylalkyl groups described herein may be substituted or unsubstituted.

The term "heteroaryl" refers to an aromatic heterocyclic ring radical. The heteroaryl ring radical may be attached to the main structure at any heteroatom or carbon atom that results in the creation of a stable structure. Unless set forth or recited to the contrary, all heteroaryl groups described herein may be substituted or unsubstituted.

The term "heteroarylalkyl" refers to a heteroaryl ring radical directly bonded to an alkyl group. The heteroarylalkyl radical may be attached to the main structure at any carbon atom in the alkyl group that results in the creation of a stable structure. Unless set forth or recited to the contrary, all heteroarylalkyl groups described herein may be substituted or unsubstituted.

Unless otherwise specified, the term "substituted" as used herein refers to substitution with any one or more or any combination of the following substituents: hydroxy, halogen, carboxyl, cyano, nitro, oxo (=O), thio (=S), substituted or unsubstituted alkyl, substituted or unsubstituted haloalkyl, substituted or unsubstituted alkoxy, substituted or unsubstituted haloalkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenylalkyl, substituted or unsubstituted cycloalkenyl, substituted or unsubstituted amino, substituted or unsubstituted aryl, substituted or unsubstituted heteroaryl, substituted or unsubstituted heterocyclylalkyl ring, substituted or unsubstituted heteroarylalkyl, substituted or unsubstituted heterocyclic ring, substituted or unsubstiuted guanidine, —CO—$OR^{x'}$, —$C(O)R^{x'}$, —$C(S)R^{x'}$, —$C(O)NR^{x'}R^{y'}$, —$C(O)ONR^{x'}R^{y'}$, —$NR^{x'}CONR^{y'}R^{z'}$, —$N(R^{x'})SOR^{y'}$, —$N(R^{x'})SO_2R^{y'}$, —(=N—N($R^{x'}$)$R^{y'}$), —$NR^{x'}C(O)OR^{y'}$, —$NR^{x'}R^{y'}$, —$NR^{x'}C(O)R^{y'}$, —$NR^{x'}C(S)R^{y'}$, —$NR^{x'}C(S)NR^{y'}R^{z'}$, —$SONR^{x'}R^{y'}$, —$SO_2NR^{x'}R^{y'}$, —$OR^{x'}$, —$OR^{x'}C(O)NR^{y'}R^{z'}$, $OR^{x'}C(O)OR^{y'}$, —$OC(O)R^{x'}$, —$OC(O)NR^{x'}R^{y'}$, —$R^{x'}NR^{y'}C(O)R^{z'}$, —$R^{x'}OR^{y'}$, —$R^{x'}C(O)OR^{y'}$, —$R^{x'}C(O)NR^{y'}R^{z'}$, —$R^{x'}C(O)R^{y'}$, —$R^{x'}OC(O)R^{y'}$, —$SR^{x'}$, —$SOR^{x'}$, —$SO_2R^{x'}$ and —$ONO_2$, wherein $R^{x'}$, $R^{y'}$ and $R^{z'}$ are independently selected from hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl or substituted or unsubstituted heterocyclic ring.

The term "treating" or "treatment" of a state, disorder or condition includes; (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof; or (c) relieving the disease, i.e., causing regression of the state, disorder or condition or at least one of its clinical or subclinical symptoms.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disorder or condition, is sufficient to effect such treatment. The "therapeutically effective amount" will vary depending on the compound, the disease and its severity and the age, weight, physical condition and responsiveness of the subject to be treated.

The compounds described in the present patent application may form salts. Non-limiting examples of pharmaceutically acceptable salts forming part of this patent application include salts derived from inorganic bases salts of organic bases, salts of chiral bases, salts of natural amino acids and salts of non-natural amino acids.

Certain compounds of the present invention, including compounds of formula (I), (Ia), (Ib), (Ic) and (Id) are capable of existing in stereoisomeric forms (e.g. diastereomers and enantiomers). The present invention includes these stereoisomeric forms (including diastereomers and enantiomers) and mixtures of them. The various stereoisomeric forms of the compounds of the present invention may be separated from one another by methods known in the art or a given isomer may be obtained by stereospecific or asymmetric synthesis. Tautomeric forms and mixtures of compounds described herein are also contemplated.

Pharmaceutical Compositions

The pharmaceutical composition of the present patent application includes at least one compound described herein and at least one pharmaceutically acceptable excipient (such as a pharmaceutically acceptable carrier or diluent). Preferably, the pharmaceutical composition includes the compound(s) described herein in an amount sufficient to inhibit TRPA1 in a subject (e.g., a human). The inhibitory activity of compounds falling within the formulas (I), (Ia), (Ib), (Ic) and (Id) may be measured by an assay provided below.

The compound of the present invention may be associated with a pharmaceutically acceptable excipient (such as a carrier or a diluent) or be diluted by a carrier, or enclosed within a carrier which can be in the form of a capsule, sachet, paper or other container.

The pharmaceutical compositions may be prepared by techniques known in the art. For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be in conventional forms, for example, capsules, tablets, aerosols, solutions, suspensions or products for topical application.

Methods of Treatment

The compounds and pharmaceutical compositions of the present invention can be administered to treat any disorder, condition, or disease treatable by inhibition of TRPA 1. For instance, the compounds and pharmaceutical compositions of the present invention are suitable for treatment or prophylaxis of the following diseases, conditions and disorders mediated or associated with the activity of TRPA1 receptors: pain, chronic pain, complex regional pain syndrome, neuropathic pain, postoperative pain, rheumatoid arthritic pain, osteoarthritic pain, back pain, visceral pain, cancer pain, algesia, neuralgia, migraine, neuropathies, chemotherapy-induced neuropathies, eye-irritation, bronchial-irritation, skin-irritation (atopic dermatitis), Frost-bites (cold-bite), spasticity, catatonia, catalepsy, parkinsons, diabetic neuropathy, sciatica, HIV-related neuropathy, post-herpetic neuralgia, fibromyalgia, nerve injury, ischaemia, neurodegeneration, stroke, post stroke pain, multiple sclerosis, respiratory diseases, asthma, cough, COPD, inflammatory disorders, oesophagitis, gastroeosophagal reflux disorder (GERD), irritable bowel syndrome, inflammatory bowel disease, pelvic hypersensitivity, urinary incontinence, cystitis, burns, psoriasis, eczema, emesis, stomach duodenal ulcer and pruritus. The connection between therapeutic effect and inhibition of TRPA1 is illustrated, for example, in Story, G. M. et al. *Cell*, 2003, 112, 819-829; McMahon, S. B. and Wood, J. N., *Cell*, 2006, 124, 1123-1125; Voorhoeve, P. M. et al. *Cell*, 2006, 124, 1169-1181; Wissenbach, U, Niemeyer, B. A. and Flockerzi, V. *Biology of the Cell*, 2004, 96, 47-54; and the references cited therein.

Pain can be acute or chronic. While acute pain is usually self-limiting, chronic pain persists for 3 months or longer and can lead to significant changes in a patient's personality; lifestyle, functional ability and overall quality of life (K. M. Foley, *Pain*, in Cecil Textbook of Medicine; J. C. Bennett & F. Plum (eds.), 20th ed., 1996, 100-107). The sensation of pain can be triggered by any number of physical or chemical stimuli and the sensory neurons which mediate the response to this harmful stimulus are termed as "nociceptors". Nociceptors are primary sensory afferent (C and Aδ fibers) neurons that are activated by a wide variety of noxious stimuli including chemical, mechanical, thermal and proton (pH<6) modalities. Nociceptors are the nerves which sense and respond to parts of the body which suffer from damage. They signal tissue irritation, impending injury, or actual injury. When activated, they transmit pain signals (via the peripheral nerves as well as the spinal cord) to the brain.

Chronic pain can be classified as either nociceptive or neuropathic. Nociceptive pain includes tissue injury-induced pain and inflammatory pain such as that associated with arthritis. Neuropathic pain is caused by damage to the sensory nerves of the peripheral or central nervous system and is maintained by aberrant somatosensory processing. The pain is typically well localized, constant and often with an aching or throbbing quality. Visceral pain is the subtype of nociceptive pain that involves the internal organs. It tends to be episodic and poorly localized. Nociceptive pain is usually time limited, meaning when the tissue damage heals, the pain typically resolves (arthritis is a notable exception in that it is not time limited).

General Methods of Preparation

The compounds described herein, including compounds of general formula (I), (Ia), (Ib), (Ic) and (Id) and specific examples are prepared using techniques known to one skilled in the art through the reaction sequences depicted in Schemes 1-10 as well as by other methods. Furthermore, in the following Synthetic schemes, where specific acids, bases, reagents, coupling agents, solvents, etc. are mentioned, it is understood that other suitable acids, bases, reagents, coupling agents etc. may be used and are included within the scope of the present invention. The compounds obtained by using the general reaction sequences may be of insufficient purity. These compounds can be purified by using any of the methods for purification of organic compounds known to persons skilled in the art, for example, crystallization or silica gel or alumina column chromatography using different solvents in suitable ratios. All possible stereoisomers are envisioned within the scope of this invention.

A general approach for the synthesis of thienopyrimidinyl acetamides of the general formula (I), wherein $Z^1, Z^2, R^1, R^2, R^3$, U, V and L are as defined above in description is prepared as described in Scheme 1. Coupling reaction of the compounds of the formula (I) with amines of the formula (2) in the presence of a suitable coupling agent such as 1-ethyl-3-(3'-dimethylaminopropyl)carbodiimide hydrochloride (EDCI)

and base in suitable solvent gives compounds of the formula (3). The selective N-alkylation of the compounds of the formula (3) with suitable alkylating agent of the formula (4) in the presence of base and solvent gives compounds of the general formula (I).

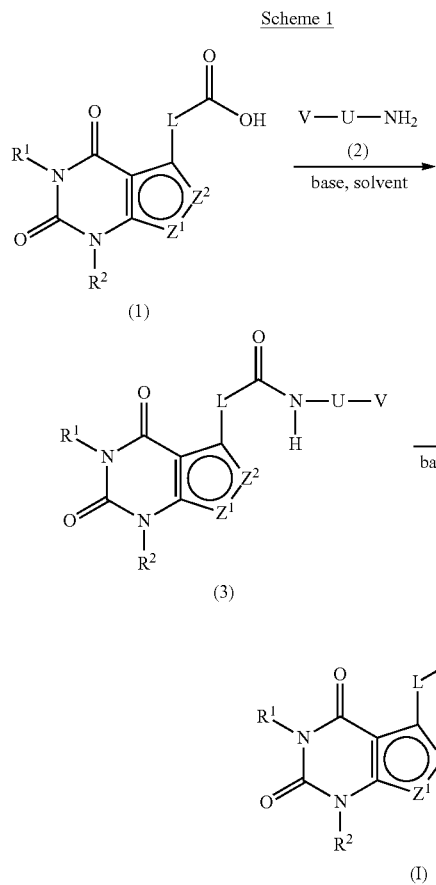

Scheme 1

(1)

(3)

(I)

A general approach for the synthesis of thieno[2,3-d]pyrimidinyl acetamides of the general formula (Ia'), wherein $R^1$, $R^2$, U and V are as defined above is prepared as described in Scheme 2. Synthesis starts from commercially available 1,3-dialkylbarbituric acid of the formula (5). The known 6-chloro-5-formyl-1,3-dimethyluracil (6) is prepared according to the reported procedure (Singh, J. S. et al, *Synthesis* 1988, 342-344) by formylation of intermediate (5) with $POCl_3$ and DMF. The treatment of 6-chloro-5-formyl-1,3-dialkyluracil (6) with hydroxylamine in methanol followed by dehydration with phosphorous oxychloride give 6-chloro-5-cyano-1,3-dimethyluracil of formula (7). Treatment of compounds of the formula (7) with alkyl mercaptoacetate of the formula (8) (wherein R is alkyl) in the presence of suitable base affords amino ester of the formula (9) through a coupling reaction followed by insitu cyclization. This conversion is similar to described by Motoi, Y. et al, *J. Heterocyclic Chem.*, 1990, 717-721. The amino ester (9) on diazotization followed by halide substitution with copper halide (such as copper bromide or copper iodide) affords an intermediate of the formula (10) where X is halogen. Aryl halide of formula (10) on reaction with allyl boronic acid pinacol ester of the formula (11) in the presence of a palladium catalyst, such as bis(triphenylphosphine)palladium dichloride or tetrakis (triphenylphosphine) palladium(0) gives allyl derivative of the formula (12) [e.g. a procedure similar to the Suzuki-Miyaura Coupling described by Kotha, et al, *Synlett* 2005, 12, 1877-1890]. Hydrolysis and decarboxylation of allyl thiophene derivative of the formula (12) using copper in the presence of quinoline at elevated temperature gives the allyl thienopyrimidinedione of the formula (14) [procedure is similar to that is reported by Ludo., E. J. Kennis. et al in *Biorg. & Med. Chem. Lett.*, 2000, 10, 71-74, and Mashraqui, S. H. et al, in *Tetrahedron,* 2005, 61, 3507-3513]. Ozonolysis of compounds of the formula (14) in methanol under basic condition followed by hydrolysis of the ester (15) with aqueous acid gave compounds of the formula (16). (This conversion is similar to described by Mohler, D. L. et al, Synthesis, 2002, 745-748). The coupling of compounds of formula (16) with respective amines of formula (2) by using a standard amide coupling method gives compounds of general formula (Ia').

Scheme 2

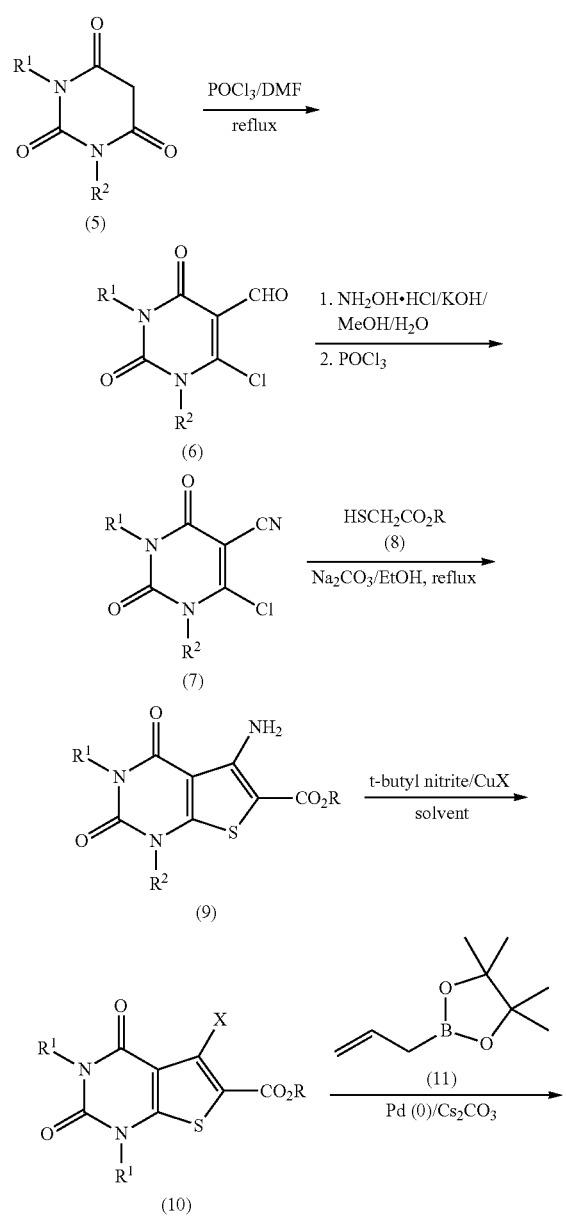

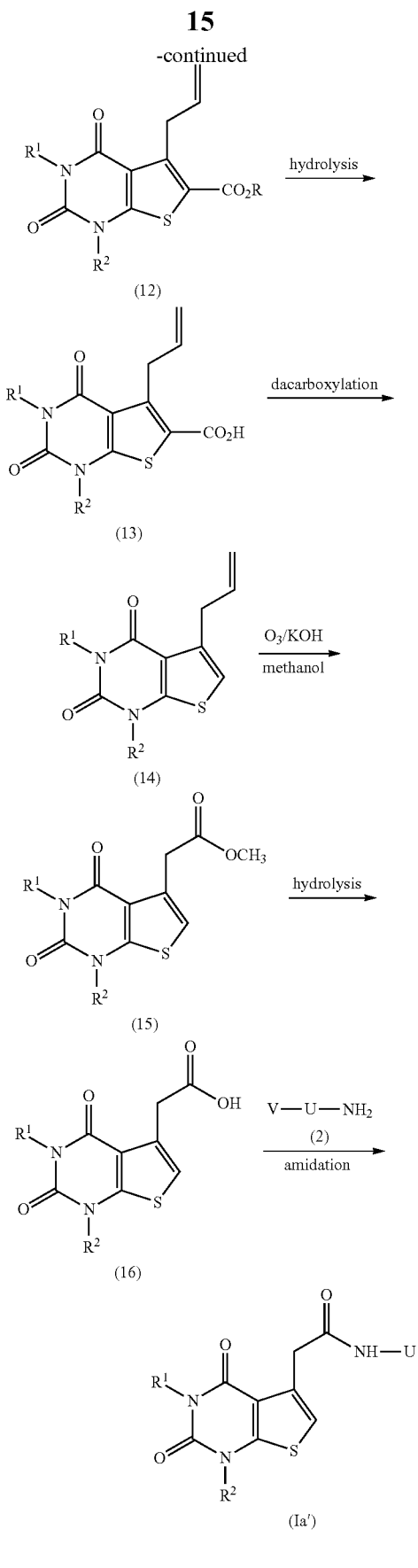

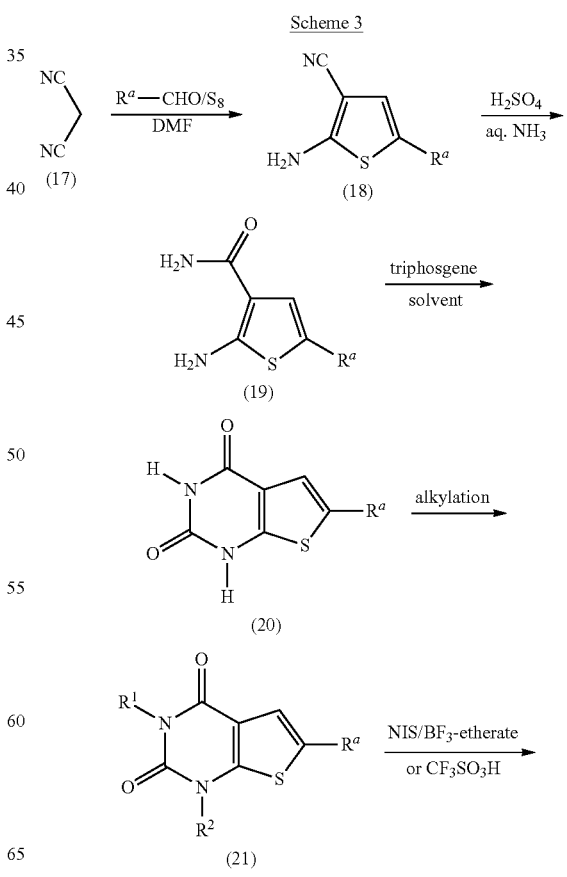

An approach for the synthesis of thieno[2,3-d]pyrimidinyl acetamides of the formula (Ia) wherein $R^a$ is an alkyl group (e.g., methyl, ethyl, propyl, isopropyl) and $R^1$, $R^2$, U and V are as defined above is shown in Scheme 3. Functionalized thiophene of the formula (18) is prepared by a one pot 3-component coupling reaction (Gewald's synthesis) using malononitrile, appropriate aldehyde and sulfur powder (Byrn, S. R. et al, *J. Pharm, Sci.,* 2001, 90, 371). The compound of the formula (18) is converted into compounds of formula (19) by a sequence of transformations well known in the art of organic synthesis. Cyclisation of compounds of the formula (19) with triphosgene gave the compounds of the formula (20), which on selective N-alkylation afforded compounds of the formula (21). Halogenation of formula (21) (e.g., N-bromosuccinimide or N-iodosuccinimide in the presence of $BF_3$-etherate or trifluoromethanesulphonic acid) gave compounds of the formula (22). This conversion is according to procedure reported by George, O. L. et al, *J. Am. Chem. soc.,* 2004, 126, 15770-15776. Suzuki-Miyaura Coupling of aryl halide of the formula (22) with allyl boronic acids of formula (11) in the presence of Pd (0) affords allyl thiophene of the formula (23) as described in scheme 1. Transformation of compounds of formula (23) into compounds of formula (24) can be accomplished by methods known to those skilled in the art [e.g., Postema, M. H. D. et al. in *J. Org. Chem.,* 2003, 68, 4748-4754]. The compounds of the formula (24) can be converted to compounds of the formula (25) by oxidation methods well known in the literature. The coupling of compounds of formula (25) with respective amines of formula (2) by using a standard amide coupling method gives compounds of general formula (Ia).

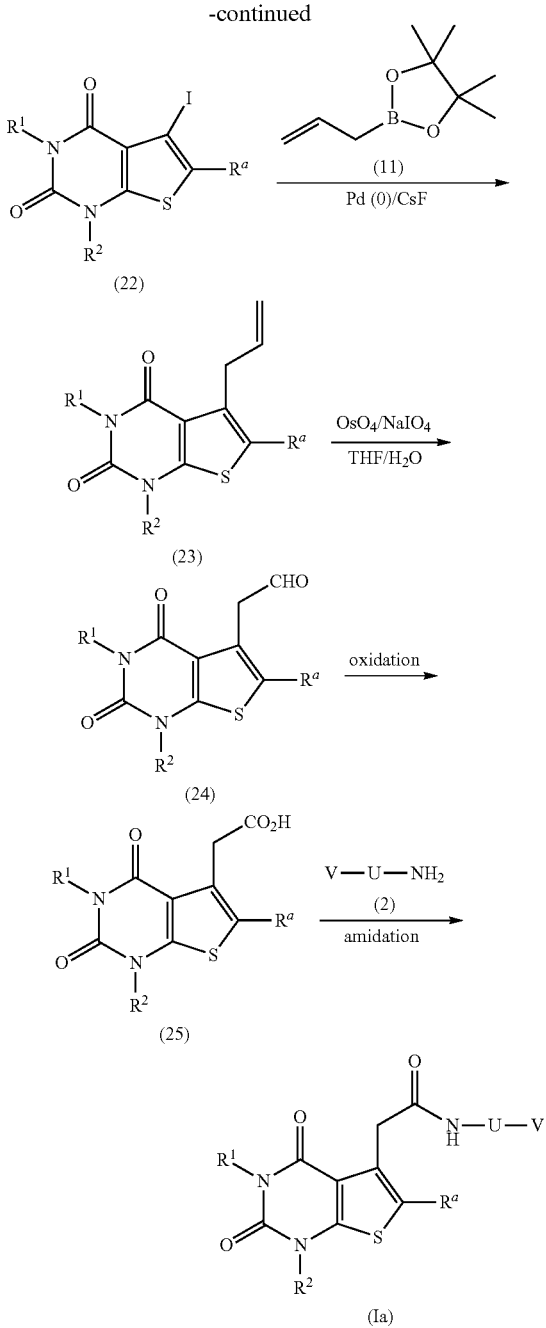

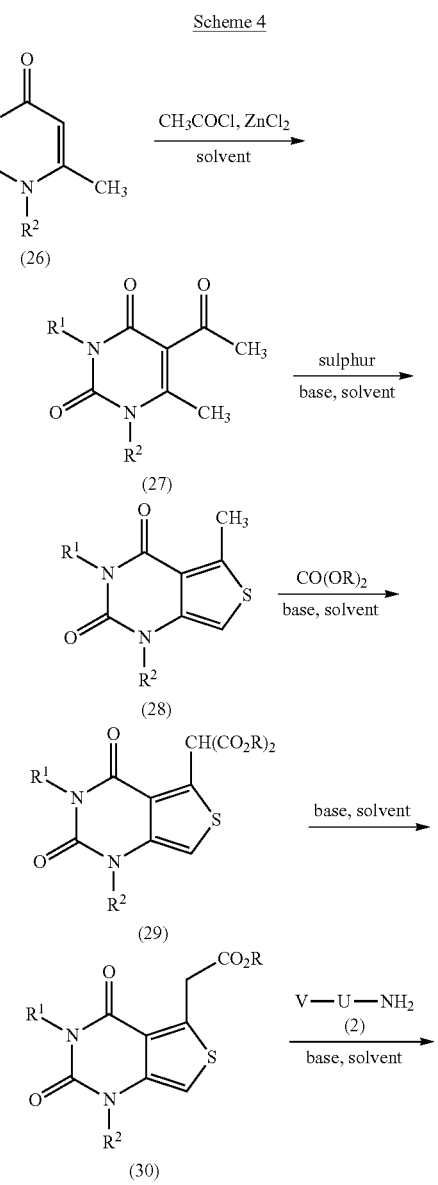

reported by Tsupak, E. B. et al in *J. Chemistry heterocyclic compounds,* 2003, 39, 953-959]. Cyclisation of the compounds of the formula (27) by Gewald's synthesis gives expected 5-methylthieno[3,4-d]pyrimidinedione of the formula (28) as described by Tormyshey, V. M. et al in *Synlett,* 2006, 2559-2164). Reaction of compounds of formula (28) with dialkyl carbonate in the presence of suitable base such as sodium hydride in a suitable solvent gives the diester of the formula (29). Dealkoxycarbonylation of compounds of the formula (29) using suitable base such as sodium hydride or using DMSO/NaCl/water afforded desired thieno[3,4-d]pyrimidinedione ester of the formula (30). Coupling reaction of ester of the formula (30) with appropriate amines of formula (2) by using suitable base such as sodium hydride in the presence of suitable solvent such as dry toluene or xylene gave compounds of general formula (Ib').

A general approach for the synthesis of thieno[3,4-d]pyrimidinyl acetamides of the formula (Ib') wherein $R^1$, $R^2$, U and V are as defined above and is prepared as shown in Scheme 4. The known 6-methyluracil derivative (26) can be prepared by two different methods. In one approach N,N-dimethyl urea is condensed with acetic anhydride in presence of pyridine as reported by Egg, H. et al in *Synthesis,* 1982, 1071-1073. Alternatively, intermediate (26) can be prepared by alkylation of 6-methyluracil according to the procedure reported by Siverman, R. B. et al, *J. Am. Chem. Soc.,* 1982, 104, 6434-6439. Friedel-Crafts acylation of intermediate (26) in the presence of catalytic amount of Lewis acid e.g., $ZnCl_2$ gives compounds of the formula (27). A similar procedure is -continued

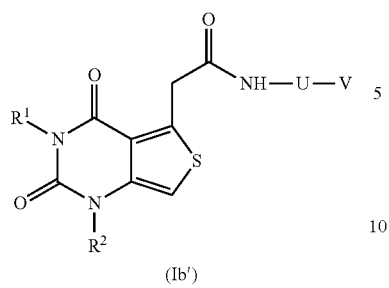

(Ib')

Another approach for the synthesis of thieno[3,4-d]pyrimidinyl acetamides of the formula (Ic) wherein $R^a$ is alkyl groups such as methyl, ethyl, propyl etc and $R^1$, $R^2$, U and V are as defined above can be prepared as shown in Scheme 5. The uracil derivative (26) prepared as describe in Scheme 4 is treated with alkyl halide of the formula $R^aX$ in the presence of a suitable base such as lithium diisopropyl amide gives compounds of the formula (31). Similar approach is reported by Hiriyakkanavar, J. et al in *Tetrahedron Lett.* 1992, 33 (41), 6173-6176]. Friedel-Crafts acylation of intermediates of the formula (31) gives the ketone (32). Cyclisation of the compounds of the formula (32) by Gewald's synthesis gives the desired thieno[3,4-d]pyrimidinedione of the formula (33). Compounds of formula (33) can be converted to ester of the formula (34) by reaction of (33) with dialkyl carbonate in the presence of a strong base such as sodium hydride followed by dealkoxycarbonylation as described in Scheme 4. Coupling reaction of ester of the formula (34) with appropriate amines of formula (2) by using suitable base such as sodium hydride in the presence of suitable solvent such as dry toluene or xylene gives compounds of general formula (Ib).

Scheme 5

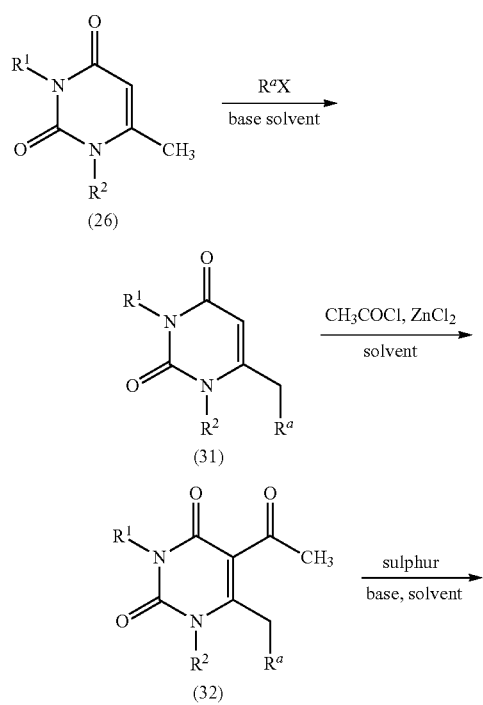

-continued

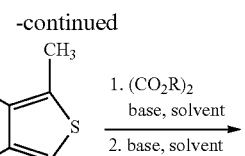

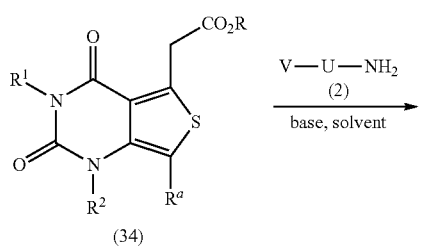

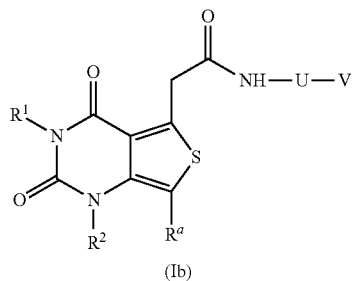

(Ib)

An alternative approach for the synthesis of thieno[3,4-d] pyrimidinyl acetamides of the formula (Ib') wherein $R^1$, $R^2$, U and V are as defined above is shown in Scheme 6. Formylation of uracil derivative (26) with phosphorous oxychloride and dry DMF gave 5-formyl derivative of the formula (35) as described by Shirahashi, M. et al, in *Yakugaku Zasshi*, 1971, 91, 1372. Treatment of 5-formyl derivative (35) with hydroxylamine hydrochloride followed by dehydration with phosphorous oxychloride gave 5-cyano derivative of the formula (36). A similar approach is reported by Hirota, K. et al in *Heteocycle*, 1998, 47, 871-882). Aminothiophene of the formula (37) is obtained by reaction of intermediate of formula (36) with sulfur powder and morpholine under Gewald's reaction conditions. Amino thiophene (37) on diazotization followed by halide substitution with a metal halide such as copper bromide or copper iodide affords a halide derivative of the formula (38). Aryl halide of the formula (38) can be transformed into allyl thiophene of the formula (39) by Suzuki-Miyaura coupling reaction with allyl boronic acid pinacol ester of the formula (11) in the presence of Pd(0) catalyst. Allyl thiophene of the formula (39) can be converted into thieno[3,4-d]pyrimidinylacetic acid of the formula (40) by oxidative cleavage of the terminal double bond as described in Scheme 1. The coupling of compounds of formula (40) with amines of the general formula (2) by using a standard amide coupling method gives compounds of general formula (Ib').

Scheme 6

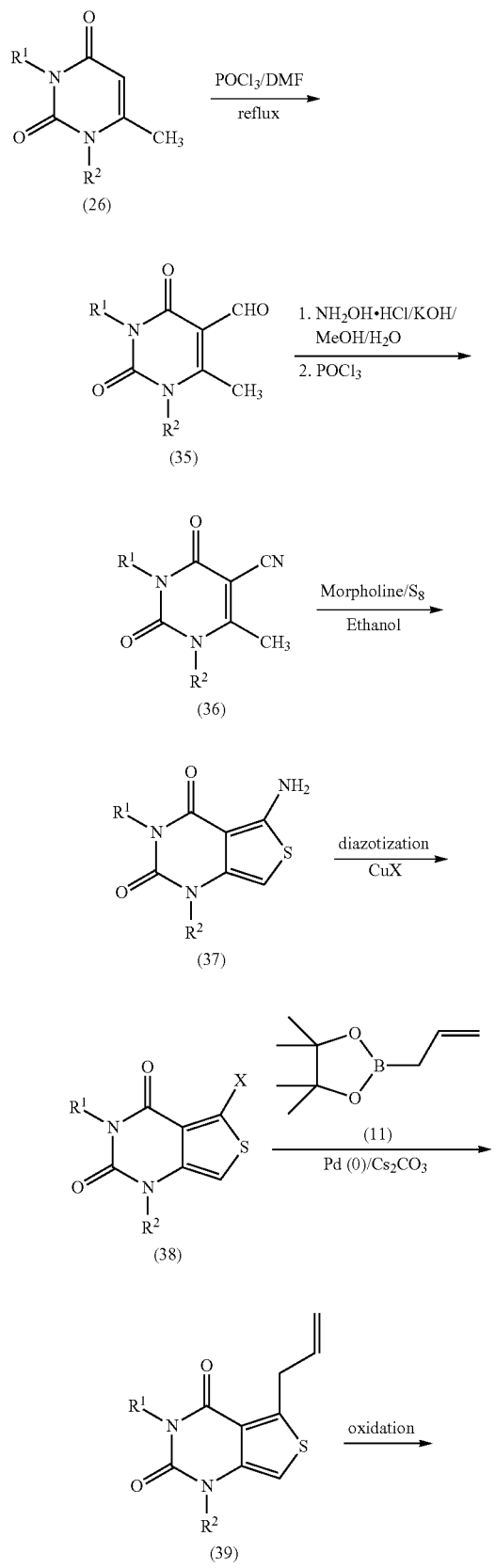

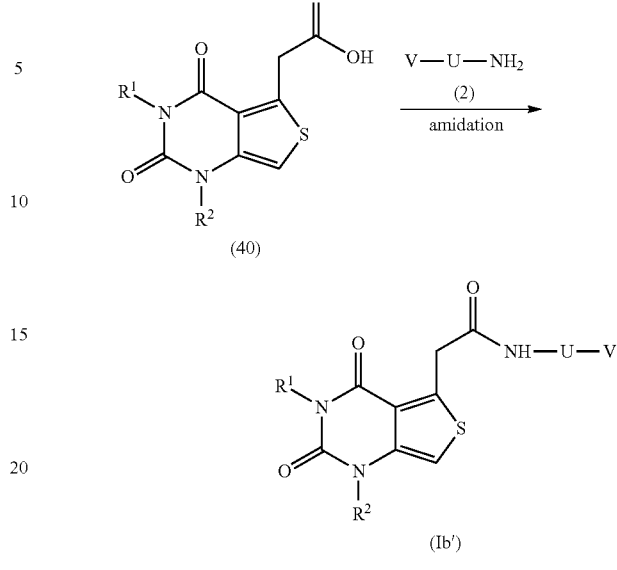

A general approach for the synthesis of compounds of formula (Ic) or (Id) wherein $R^a$ is hydrogen or alkyl, $R^1$, $R^2$, $R^4$, $R^5$, $R^6$, $R^7$ $R^8$ and $R^9$ are as defined above is prepared as shown is Scheme 7. The coupling of compounds of formula (25) with respective amines of formula (46) by using a standard amide coupling method will give compounds of general formula (Ic).

Similarly the coupling of compounds of formula (40) with respective amines of formula (46) by using a standard amide coupling method will give compounds of general formula (Id).

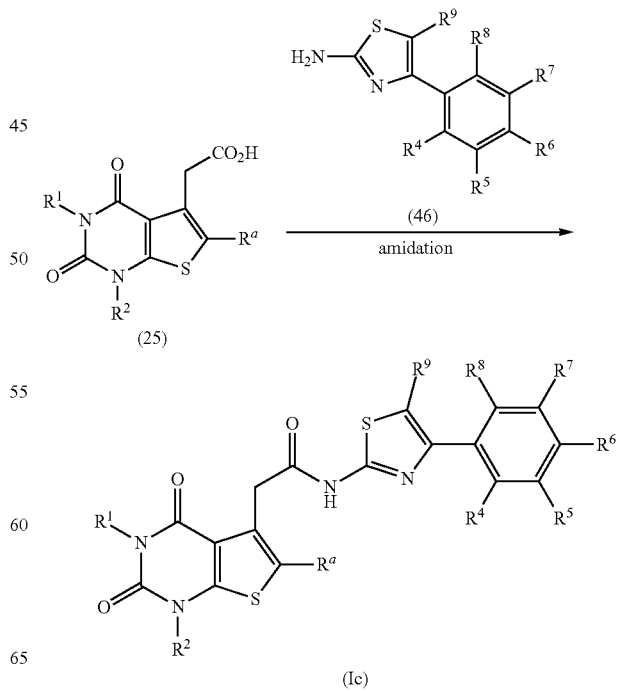

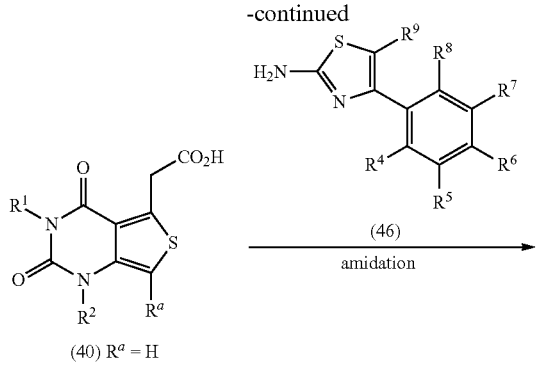

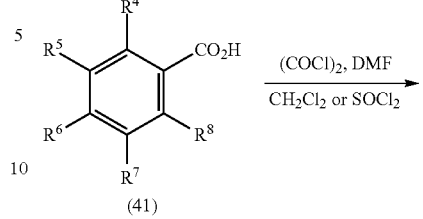

Scheme 8

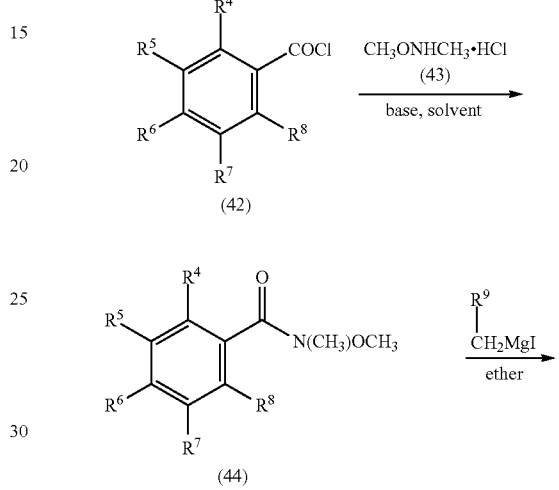

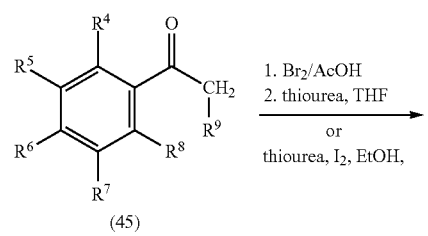

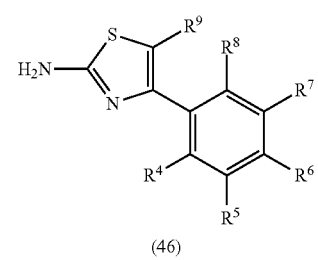

Scheme 8 depicts synthesis of 2-amino-4-aryl thiazoles of the formula (46) (wherein $R^4$, $R^5$, $R^6$, $R^7$ $R^8$ and $R^9$ are as defined above) which is prepared from acetophenones of the formula (45) using known approaches. Certain di- and tri-substituted acetophenones were not commercially available and they were prepared from the corresponding benzoic acid derivative of formula (41) in three steps. Thus, acid of formula (41) was converted to the corresponding acid chloride of formula (42) using oxalyl chloride in the presence of catalytic amounts of DMF in dry dichloromethane. The acid chloride of formula (42) was converted to corresponding Weinerb amide of formula (44) by treating with N,O-dimethylhydroxylamine hydrochloride of formula (43) in the presence of a suitable base such as triethylamine. The addition of alkyl magnesium iodide to Weinreb amide of formula (44) afforded acetophenone derivative of formula (45).

Conversion of acetophenone derivative of formula (45) to 2-amino-4-substituted aryl thiazole of the formula (46) can be effected by two approaches as described in Scheme 8. In the first case acetophenone was converted to the corresponding phenacyl bromide, which in turn was reacted with thiourea in a suitable solvent such as tetrahydrofuran at refluxing condition. Alternatively, acetophenone derivative of formula (45) can be converted to 2-amino-4-aryl thiazole (46) in one step by its reaction with thiourea and iodine in refluxing ethanol (Carroll, K. et al, *J. Am. Chem. Soc.*, 1950, 3722 and Naik, S. J.; Halkar, U. P., *ARKIVOC*, 2005, xiii, 141-149).

Synthesis of 2-amino-4-arylimidazolamine of the formula (48) (wherein $R^4$, $R^5$, $R^6$, $R^7$ $R^8$ and $R^9$ are as defined above) is described in Scheme 9. Thus, reaction of acetophenone derivative of formula (45) with bromine in acetic acid gives phenacyl bromide, which on reaction with acetyl guanidine in acetonitrile at reflux temperature gives N-acetyl imidazole of the formula (47). The N-deacetylation of (47) under acidic conditions affords 2-amino-4-arylimidazoles of the formula (48). This is similar to the procedure reported by Thomas, L. et al in *J. Org. Chem.*, 1994, 59, 7299-7305.

Scheme 9

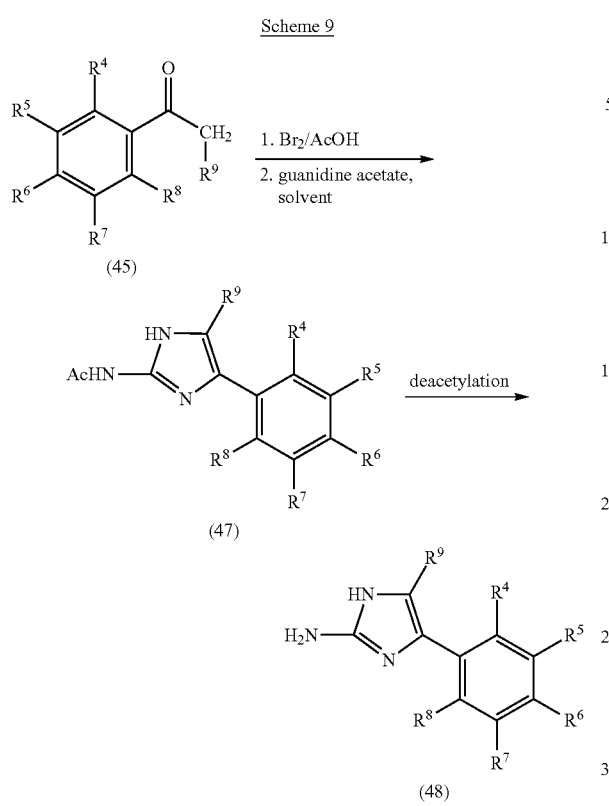

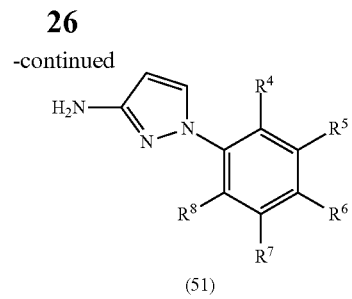

Some of the 5-amino-3-phenylpyrazoles used for the synthesis of compounds of present invention were commercially available. Commercially unavailable 3-amino-1-arylpyrazoles were prepared as shown in Scheme 10. Reaction of phenylhydrazine derivative of formula (49) with acrylonitrile in the presence of a suitable base such as sodium ethoxide or sodium methoxide in refluxing ethanol affords the dihydro derivative of compound of formula (50). Intermediate (50) on oxidation with N-bromosuccinimide as described by Duffin, G. F. et al, *J. Chem. Soc.,* 1954, 408-415, gives 3-amino-1-arylpyrazoles derivative of formula (51) (wherein $R^4$, $R^5$, $R^6$, $R^7$ and $R^8$ are as defined above).

Scheme 10

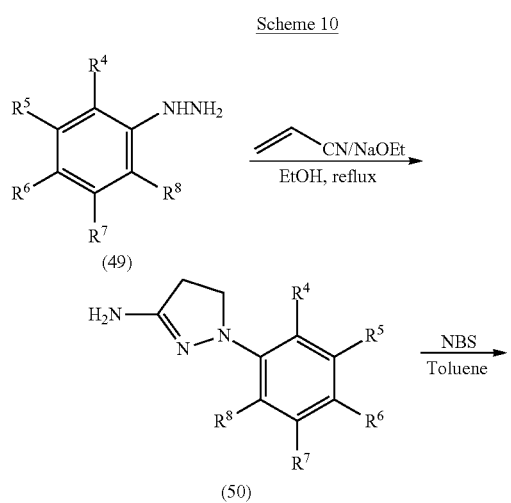

EXPERIMENTAL

Unless otherwise stated, work-up includes distribution of the reaction mixture between the organic and aqueous phase indicated within parentheses, separation of layers and drying the organic layer over sodium sulphate, filtration and evaporation of the solvent. Purification, unless otherwise mentioned, includes purification by silica gel chromatographic techniques, generally using ethyl acetate/petroleum ether mixture of a suitable polarity as the mobile phase. Use of a different eluent system is indicated within parentheses. The following abbreviations are used in the text: DMSO-$d_6$: Hexadeuterodimethyl sulfoxide; DMAP: 4-dimethylaminopyridine; DMF: N,N-dimethylformamide, J: Coupling constant in units of Hz; RT or rt: room temperature (22-26° C.). Aq.: aqueous AcOEt: ethyl acetate; equiv. or eq.: equivalents.

INTERMEDIATES

Intermediate 1

(1,3-Dimethyl-2,4-dioxo-1,2,3,4-tetrahydrothieno[2,3-d]pyrimidin-5-yl)acetic acid

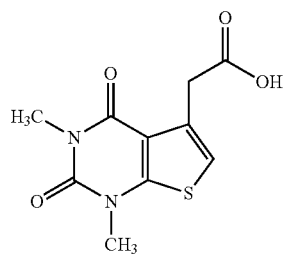 [SMILES: Cn1c(=O)c2c(CC(=O)O)csc2n(C)c1=O]

Step 1

6-Chloro-1,3-dimethyl-2,4-dioxo-1,2,3,4-tetrahydropyrimidine-5-carboxaldehyde: Phosphorous oxychloride (690 ml) was added slowly to dry N,N-dimethyl formamide (180 ml) at 0° C. The mixture was then allowed to warm to room temperature. 1,3-Dimethylbarbituric acid (60 g, 384.27 mmol) was added portion wise and refluxed for 45 min. The excess of phosphorous oxychloride and DMF were distilled off under reduced pressure and the viscous residue was poured into ice-cold water (2000 ml). The reaction mixture was allowed to room temperature and extracted with chloroform (3×500 ml). The combined organic extracts were dried over $Na_2SO_4$ and concentrated. The crude material obtained was then stirred in 10% ethyl acetate in hexane (150 ml) to obtain 58 g of the product as the pale yellow solid; $^1$H NMR (300 MHz, $CDCl_3$) δ 3.41 (s, 3H), 3.69 (s, 3H), 10.18 (br s, 1H).

Step 2

6-Chloro-1,3-dimethyl-2,4-dioxo-1,2,3,4-tetrahydropyrimidine-5-carboxaldehyde oxime: To a mixture of Step 1 intermediate (56 g, 262.37 mmol) and hydroxylamine hydrochloride (22.8 g, 327.97 mmol) in methanol (525 ml) was added drop-wise a solution of KOH (18.3 g, 327.97 mmol) in water (32 ml) over a period of 1 h, while reaction mixture was maintained below 10° C. The mixture was stirred at room temperature for 1 h, and the resulting oxime precipitate was collected by filtration, washed with water (2×250 ml), methanol (2×150 ml) and dried to give 46.3 g of the product as a pale yellow solid; $^1$H NMR (300 MHz, DMSO-d$_6$) δ 3.19 (s, 3H), 3.51 (s, 3H), 7.94 (s, 1H), 11.40 (br s, 1H).

Step 3

6-Chloro-1,3-dimethyl-2,4-dioxo-1,2,3,4-tetrahydropyrimidine-5-carbonitrile: Step 2 intermediate (46 g, 263.48 mmol) was added portion-wise to phosphorous oxychloride (410 ml) at room temperature and reaction was stirred further for 2 h. The excess of phosphorous oxychloride was evaporated under reduced pressure. The crude residue obtained was washed with diethyl ether several times and triturated with water. The solid obtained was filtered, washed with methanol and dried to give 33.4 g of the product as an off-white solid; $^1$H NMR (300 MHz, DMSO-d$_6$) δ 3.38 (s, 3H), 3.69 (s, 3H).

Step 4

Ethyl 5-amino-1,3-dimethyl-2,4-dioxo-1,2,3,4-tetrahydrothieno[2,3-d]pyrimidine-6-carboxylate: A mixture of Step 3 intermediate (32 g, 160.00 mmol), ethyl mercapto acetate (19.4 ml, 176.88 mmol) and anhydrous sodium carbonate (17.0 g, 105.99 mmol) in ethanol (800 ml) were refluxed with stirring for 3 h. The reaction mixture was cooled to room temperature. The solid obtained was collected by filtration, washed with water, ethanol and dried to give 41.6 g of the product as an off-white solid; $^1$H NMR (300 MHz, CDCl$_3$) δ 1.35 (t, J=6.6 Hz, 3H), 3.39 (s, 3H), 3.49 (s, 3H), 4.29 (q, J=6.9 Hz, 2H), 6.83 (br s, 2H).

Step 5

Ethyl 5-bromo-1,3-dimethyl-2,4-dioxo-1,2,3,4-tetrahydrothieno[2,3-d]pyrimidine-6-carboxylate: To a stirred solution of tert-butyl nitrite (26.3 ml, 220.21 mmol) in acetonitrile (590 ml) was added copper bromide (31.5 g, 220.21 mmol) slowly during 10-15 min. Step 4 intermediate (41.4 g, 146.191 mmol) was added portion-wise at room temperature. The reaction was heated at 65° C. for 3 h. The mixture was cooled to room temperature, quenched with saturated solution of sodium thiosulphate, 1 N HCl (200 ml) was added and extracted with ethyl acetate. The combined organic layers were washed with water, dried over sodium sulphate and concentrated. The crude product obtained was then purified by silica gel column chromatography using 3% ethyl acetate in chloroform to give 24.6 g of the product as an off-white solid; $^1$H NMR (300 MHz, CDCl$_3$) δ 1.41 (t, J=6.9 Hz, 3H), 3.42 (s, 3H), 3.57 (s, 3H), 4.39 (q, J=6.9 Hz, 2H).

Step 6

Ethyl 5-allyl-1,3-dimethyl-2,4-dioxo-1,2,3,4-tetrahydrothieno[2,3-d]pyrimidine-6-carboxylate: To a stirred solution of Step 5 intermediate (24.5 g, 70.60 mmol) in dry THF (350 ml) was added cesium carbonate (46.0 g, 141.20 mmol) and allyl boronic acid pinacol ester (23.8 ml, 127.08 mmol) under nitrogen atmosphere and the mixture was degassed for 10 min. Tetrakis(triphenylphosphine)palladium(0) (8.1 g, 7.06 mmol) was added and the reaction was refluxed for 24 h under nitrogen atmosphere. The reaction mixture was diluted with water (250 ml) and extracted with ethyl acetate (3×100 ml). The combined extracts were concentrated and the residue obtained was purified by silica gel column chromatography using 5% ethyl acetate in pet ether to give 4.62 g of the product as an off-white solid; $^1$H NMR (300 MHz, CDCl$_3$) δ 1.39 (t, J=7.2 Hz, 3H), 3.41 (s, 3H), 3.56 (s, 3H), 4.18-4.24 (m, 2H), 4.31-4.40 (m, 2H), 4.99-5.15 (m, 2H), 5.95-6.03 (m, 1H).

Step 7

5-Allyl-1,3-dimethyl-2,4-dioxo-1,2,3,4-tetrahydrothieno[2,3-d]pyrimidine-6-carboxylic acid: To a stirred solution of Step 6 intermediate (4.6 g, 14.93 mmol) in ethanol (50 ml) was added 1.25 M aqueous KOH (15.5 ml) and mixture was refluxed for 2 h. The solvent was concentrated under reduced pressure and acidified with 1 N HCl. The solid separated out was filtered and dried to give 3.50 g of the product as an off-white solid; $^1$H NMR (300 MHz, CDCl$_3$) δ 3.42 (s, 3H), 3.56 (s, 3H), 4.24 (d, J=6.0 Hz, 2H), 5.01-5.18 (m, 2H), 5.95-6.05 (m, 1H).

Step 8:

5-Allyl-1,3-dimethylthieno[2,3-d]pyrimidine-2,4(1H,3H)-dione: Copper powder (231 mg, 3.642 g atom) was added to a suspension of Step 7 intermediate (3.4 g, 12.142 mmol) in quinoline (60 ml) and the resulting mixture was stirred and heated at 235° C. for 3 h under nitrogen. The reaction mixture was cooled to room temperature, diluted with ethyl acetate, washed with 1 N HCl and water. The combined organic layers were dried and concentrated. The purification of crude product by silica gel column chromatography by using 5% ethyl acetate in petroleum ether gave 2.17 g of the product as an off-white solid; $^1$H NMR (300 MHz, CDCl$_3$) δ 3.41 (s, 3H), 3.55 (s, 3H), 3.71 (s, 2H), 5.09-5.15 (m, 2H), 5.97-6.10 (m, 1H), 6.50 (s, 1H).

Step 9

Methyl (1,3-dimethyl-2,4-dioxo-1,2,3,4-tetrahydrothieno[2,3-d]pyrimidin-5-yl)acetate: To a solution of Step 8 intermediate (2.14 g, 9.033 mmol) in dichloromethane (106 ml) was added 2.5 M methanolic NaOH solution (60 ml). The solution was cooled (−78° C.) and ozone gas was bubbled through for 90 min. The reaction mixture was warmed to room temperature, diluted with water and extracted with ethyl acetate. The combined organic layers were washed with water, dried over Na$_2$SO$_4$ and concentrated. The residue obtained was purified by silica gel column chromatography by using 5% ethyl acetate in petroleum ether to afford 1.35 g of the product as a pale yellow solid; $^1$H NMR (300 MHz, CDCl$_3$) δ 3.39 (s, 3H), 3.47 (s, 3H), 3.74 (s, 3H), 3.95 (s, 2H), 6.70 (s, 1H).

Step 10

(1,3-Dimethyl-2,4-dioxo-1,2,3,4-tetrahydrothieno[2,3-d]pyrimidin-5-yl)acetic acid: A mixture of Step 9 intermediate (1.3 g, 4.850 mmol) and 6 N H$_2$SO$_4$ (12 ml) in 1,4-dioxane (12 ml) was stirred at reflux temperature for 1 h to give a homogeneous pale yellow solution. This solution was cooled, diluted with water and extracted with ethyl acetate (2×50 ml). The combined organic layers were washed with water, dried over Na$_2$SO$_4$ and concentrated. The residue obtained was triturated in diethyl ether, solid obtained was collected by filtration to give 450 mg of the product as a white solid; $^1$H NMR (DMSO-d$_6$, 300 MHz) δ 3.21 (s, 3H), 3.45 (s, 3H), 3.79 (s, 2H), 7.01 (s, 1H), 12.22 (br s, 1H).

Intermediate 2

(1,3,6-Trimethyl-2,4-dioxo-1,2,3,4-tetrahydrothieno[2,3-d]pyrimidin-5-yl)acetic acid

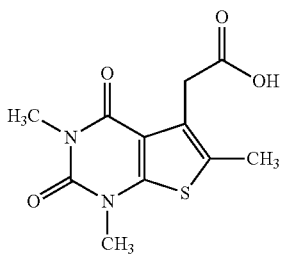

Step 1

2-Amino-5-methylthiophene-3-carbonitrile: To a stirred solution of propionaldehyde (87.99 g, 1514 mmol) and sulphur powder (48.4 g, 1514 mmol) in dry DMF (320 ml), triethylamine (127.7 ml, 909 mmol) was added dropwise at 0° C. The resulting dark solution was then warmed to room temperature over a period of 1 h. A solution of malononitrile (100 g, 1514 mmol) in dry DMF (180 ml) was transferred to the addition funnel and added in a dropwise manner. The resulting brownish mixture was stirred overnight at room temperature. The reaction mixture was diluted with water and extracted with ethyl acetate with ethyl acetate (3×500 ml). The combined organic extracts were washed with water (2×300 ml), dried over $Na_2SO_4$ and concentrated. The residue obtained was purified by silica gel column chromatography using 10% ethyl acetate in petroleum ether to obtain 25.8 g of the product as a pale brown solid; $^1$H NMR (300 MHz, $CDCl_3$) δ 2.28 (s, 3H), 4.60 (br. s, 2H), 6.33 (s, 1H).

Step 2

2-Amino-5-methylthiophene-3-carboxamide: The Step 1 intermediate (25.5 g, 163.46 mmol) was added portion-wise to concentrated sulfuric acid (163 ml) under stirring and the mixture was then heated at 55° C. for 1 h. The reaction mixture was cooled to room temperature and poured over crushed ice. The mixture was basified by the addition of liquid ammonia. The solid separated out was collected by filtration to give 16.8 g of the product as a pale brown solid; $^1$H NMR (300 MHz, $CDCl_3$) δ 2.27 (s, 3H), 5.34 (br. s, 2H), 6.01 (br. s, 2H), 6.33 (s, 1H).

Step 3

6-Methylthieno[2,3-d]pyrimidine-2,4(1H,3H)-dione: To a stirred solution of Step 2 intermediate (16.5 g, 94.82 mmol) in dry THF (316 ml) was added triphosgene (14.07 g, 47.41 mmol) and the mixture was refluxed for overnight under nitrogen atmosphere. The mixture was cooled to room temperature and diluted with water (200 ml) under stirring. The solid precipitated out was collected by filtration and dried to give 13.8 g of the desired product; $^1$H NMR (300 MHz, DMSO-$d_6$) δ 2.36 (s, 3H), 6.82 (s, 1H), 11.07 (br. s, 1H), 11.79 (br. s, 1H).

Step 4

1,3,6-Trimethylthieno[2,3-d]pyrimidine-2,4(1H,3H)-dione: A solution of Step 3 intermediate (13.5 g, 74.17 mmol) in dry DMF (148 ml) was added anhydrous $K_2CO_3$ (51.25 g, 370.85 mmol) and the mixture was stirred at room temperature for 1 h. Methyl iodide (34.74 g, 244.78 mmol) was added slowly with stirring and further stirred at room temperature for 24 h. The reaction mixture was diluted with water and the solid precipitated out was filtered, washed with water and dried to give 12.6 gm of the product as a brown solid; $^1$H NMR (300 MHz, DMSO-$d_6$) δ 2.42 (s, 3H), 3.22 (s, 3H), 3.42 (s, 3H), 6.90 (s, 1H).

Step 5

5-Iodo-1,3,6-trimethylthieno[2,3-d]pyrimidine-2,4(1H,3H)-dione: To a stirred solution of Step 4 intermediate (12.5 g, 59.52 mmol) in boron trifluoride diethyl etherate (300 ml) was added N-iodosuccinimide (19.9 g, 89.28 mmol) and the mixture was stirred for 3 h at room temperature under nitrogen atmosphere. The reaction mixture was diluted with water (100 ml), extracted with ethyl acetate (3×200 ml) and the combined organic layers were washed with water (2×150 ml), dried over $Na_2SO_4$ and concentrated under reduced pressure. The crude product was purified by silica gel column chromatography using 2% ethyl acetate in chloroform to obtain 9.7 g of the product as a pale brown solid; $^1$H NMR (300 MHz, DMSO-$d_6$) δ 2.37 (s, 3H), 3.21 (s, 3H), 3.42 (s, 3H); MS (m/z) 337.11 (M+H)$^+$.

Step 6

5-Allyl-1,3,6-trimethylthieno[2,3-d]pyrimidine-2,4(1H,3H)-dione: This compound was prepared as described in Step 6 of Intermediate 1. Coupling of Step 5 intermediate (9.0 g, 26.78 mmol) with allyl boronic acid pinacol ester (9.0 ml, 48.21 mmol) in the presence of tetrakis(triphenylphosphine)palladium(0) (3.09 g, 2.678 mmol) and cesium fluoride (8.13 g, 53.56 mmol) in dry THF gave 4.5 g of title compound as off white solid. $^1$H NMR (300 MHz, $CDCl_3$) δ 2.22 (s, 3H), 3.40 (s, 3H), 3.51 (s, 3H), 3.66 (d, J=5.4 Hz, 2H), 5.00-4.92 (m, 2H), 6.03-5.90 (m, 1H).

Step 7

(1,3,6-Trimethyl-2,4-dioxo-1,2,3,4-tetrahydrothieno[2,3-d]pyrimidin-5-yl)acetaldehyde: Osmium tetraoxide (2.5 wt. % in tert. butanol, 10 mg, 0.008 mmol) was added to a slurry of Step 6 intermediate (1.0 g, 4.0 mmol), sodium periodate (1.78 g, 8.48 mmol) in THF: $H_2O$ (1:4, 80 ml) and resulting mixture was stirred at room temperature for 6 h. The reaction was quenched by the addition of saturated solution of sodium thiosulphate and extracted with ethyl acetate (3×150 ml). The combined organic extracts were washed with brine, dried over $Na_2SO_4$ and the evaporation of the solvent gave 0.92 g of title compound as white solid. $^1$H NMR (300 MHz, $CDCl_3$) δ 2.32 (s, 3H), 3.38 (s, 3H), 3.52 (s, 3H), 4.01 (s, 2H), 9.79 (br. s, 1H).

Step 8

(1,3,6-Trimethyl-2,4-dioxo-1,2,3,4-tetrahydrothieno[2,3-d]pyrimidin-5-yl)acetic acid: To a solution of Step 7 intermediate (900 mg, 3.57 mmol) and sulphamic acid (693 mg, 7.142 mmol) in acetone (17.8 ml) was added sodium chlorite (484 mg, 5.357 mmol) in water (5.35 ml) and reaction mixture was stirred for 2 h. The solvent was evaporated, diluted with water and acidified with 1N HCl. Solid obtained was filtered and dried to give 375 mg of title compound as a white solid. $^1$H NMR (300 MHz, DMSO-$d_6$) δ 2.30 (s, 3H), 3.20 (s, 3H), 3.42 (s, 3H), 3.80 (s, 2H), 12.19 (br s, 1H); MS (m/z) 249.10 (M+H)$^+$.

Intermediate 3

(6-Ethyl-1,3-dimethyl-2,4-dioxo-1,2,3,4-tetrahydrothieno[2,3-d]pyrimidin-5-yl)acetic acid

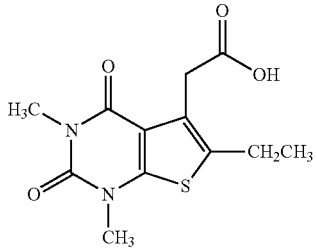 [SMILES: CCc1sc2c(c1CC(=O)O)c(=O)n(C)c(=O)n2C]

This compound was prepared in 8 steps by following the procedure described for the preparation of Intermediate 2, except for the use of butyraldehyde in the place of propionaldehyde in the first step. The compound was isolated as a white solid; $^1$H NMR (300 MHz, DMSO-$d_6$) δ 1.12-1.27 (m, 3H), 2.50-2.78 (m, 2H), 3.23 (s, 3H), 3.43 (s, 3H), 3.80 (s, 2H), 12.19 (br s, 1H).

Intermediate 4

(1,3-Dimethyl-2,4-dioxo-6-propyl-1,2,3,4-tetrahydrothieno[2,3-d]pyrimidin-5-yl)acetic acid

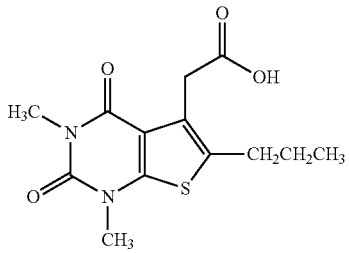

This compound was prepared in 8 steps by following the procedure described for the preparation of Intermediate 2, except for the use of valeraldehyde in the place of propionaldehyde in the first step. The compound was isolated as a white solid; $^1$H NMR (300 MHz, DMSO-$d_6$) δ 0.91 (t, J=7.5 Hz, 3H), 1.51-1.60 (m, 2H), 2.69 (t, J=6.9 Hz, 2H), 3.20 (s, 3H), 3.35 (s, 3H), 3.79 (s, 2H), 12.19 (br s, 1H).

Intermediate 5

(6-Isopropyl-1,3-dimethyl-2,4-dioxo-1,2,3,4-tetrahydrothieno[2,3-d]pyrimidin-5-yl)acetic acid

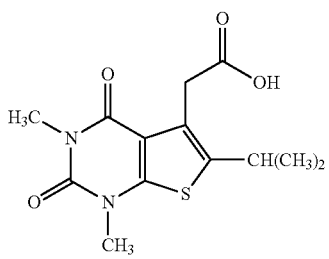 [SMILES: CC(C)c1sc2c(c1CC(=O)O)c(=O)n(C)c(=O)n2C]

This compound was prepared in 8 steps by following the procedure described for the preparation of Intermediate 2, except for the use of isovaleraldehyde in the place of propionaldehyde in the first step. The compound was isolated as a white solid; $^1$H NMR (300 MHz, DMSO-$d_6$) δ 1.22 (d, J=6.3 Hz, 6H), 3.20 (s, 3H), 3.32-3.38 (m, 1H, overlapped with DMSO peak), 3.44 (s, 3H), 3.83 (s, 2H), 12.19 (br s, 1H).

Intermediate 6

Ethyl (1,3-dimethyl-2,4-dioxo-1,2,3,4-tetrahydrothieno[3,4-d]pyrimidin-5-yl)acetate

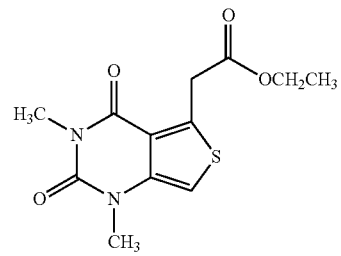 [SMILES: CCOC(=O)Cc1scc2c1c(=O)n(C)c(=O)n2C]

Step 1

1,3,6-Trimethylpyrimidine-2,4(1H,3H)-dione: To a solution of N,N-dimethyl urea (10.0 g, 113.588 mmol) and 4-dimethylamino pyridine (13.873 g, 113.588 mmol) in dry pyridine (30 ml), acetic anhydride (32.20 ml, 340.67 mmol) was added dropwise at 0° C. The reaction mixture was stirred at room temperature for overnight. The reaction mixture was quenched into 2 N HCl (250 ml) and extracted with chloroform (2×250 ml). The organic layer was washed with 1 N HCl (100 ml), sodium bicarbonate solution (75 ml), brine (75 ml) and dried ($Na_2SO_4$). The solvent was evaporated under reduced pressure to obtain 10.25 g of the product as a yellow solid; $^1$H NMR (300 MHz, CDCl$_3$) δ 2.24 (s, 3H), 3.33 (s, 3H), 3.40 (s, 3H), 5.62 (s, 1H).

Step 2

5-Acetyl-1,3,6-trimethylpyrimidine-2,4(1H,3H)-dione: A mixture of Step 1 intermediate (10.0 g, 62.893 mmol), acetyl chloride (4.47 ml, 62.893 mmol) and anhydrous zinc chloride (8.57 g, 62.893 mmol) in dry benzene (150 ml) was refluxed for 48 h. The solvent was completely evaporated under reduced pressure, diluted with water (500 ml) and extracted with chloroform (3×150 ml). The combined organic layers were washed with water (150 ml), dried ($Na_2SO_4$) and concentrated. The residue obtained was purified by silica gel column chromatography by using 30% ethyl acetate in petroleum ether to afford 4.7 g of the product as a pale yellow solid; $^1$H NMR (300 MHz, CDCl$_3$) δ 2.38 (s, 3H), 2.55 (s, 3H), 3.37 (s, 3H), 3.48 (s, 3H).

Step 3

1,3,5-trimethylthieno[3,4-d]pyrimidine-2,4(1H,3H)-dione: To a stirred solution of Step 2 intermediate (3.0 g, 14.150 mmol) in dry ethanol (56 ml) were added morpholine (1.854 ml, 21.226 mmol), sulphur (679.2 mg, 21.226 mmol) and acetic acid (424 μl, 7.075 mmol) at room temperature. After refluxing for 72 h, the reaction mixture was cooled to room temperature, diluted with water (150 ml) and extracted with ethyl acetate (150 ml). The combined organic layers washed with sodium bicarbonate solution (75 ml), brine (50 ml), dried ($Na_2SO_4$) and filtered. The filtrate was concentrated under reduced pressure. The residue obtained after the evaporation of the solvent was purified by silica gel column chromatography using 15% ethyl acetate in petroleum ether to obtain 1.5 g of the product as an off-white solid; $^1$H NMR (300 MHz, CDCl$_3$) δ 2.87 (s, 3H), 3.39 (s, 3H), 3.46 (s, 3H), 6.25 (s, 1H).

Step 4

Diethyl (1,3-dimethyl-2,4-dioxo-1,2,3,4-tetrahydrothieno[3,4-d]pyrimidin-5-yl)acetate: To a stirred solution of Step 3 intermediate (2.3 g, 10.952 mmol) in diethylcarbonate (43 ml) was added sodium hydride (60% dispersion in mineral oil, 1.05 g, 26.29 mmol) and refluxed for 48 h. The reaction mixture was cooled to room temperature, quenched into water and extracted with ethyl acetate (3×75 ml). The combined organic layers were washed with brine (50 ml), dried over Na$_2$SO$_4$ and concentrated. Purification of crude product by silica gel column chromatography using 12% ethyl acetate in petroleum ether to obtain 1.56 g of the product as a yellow solid; $^1$H NMR (300 MHz, CDCl$_3$) δ 1.30 (t, J=6.9 Hz, 6H), 3.39 (s, 3H), 3.48 (s, 3H), 4.20-4.31 (m, 4H), 6.40 (s, 1H), 6.58 (s, 1H).

Step 5

Ethyl (1,3-dimethyl-2,4-dioxo-1,2,3,4-tetrahydrothieno[3,4-d]pyrimidin-5-yl)acetate: To a stirred solution of Step 4 intermediate (1.5 g, 4.237 mmol) in dry ethanol (17 ml) was added a catalytic amount of sodium hydride (60% dispersion in mineral oil, 16.94 mg, 0.423 mmol) at room temperature and refluxed for 2 h. The solvent was completely evaporated under reduced pressure and diluted with water, solid obtained was filtered and dried to obtain 615 mg of the product as an off-white solid; $^1$H NMR (300 MHz, CDCl$_3$) δ 1.29 (t, J=7.2 Hz, 3H), 3.38 (s, 3H), 3.47 (s, 3H), 4.22 (q, J=7.2 Hz, 2H), 4.37 (s, 2H), 6.44 (s, 1H).

General Procedure for the Preparation of 2-amino-4-aryl thiazoles

Method 1

A solution of acetophenone derivative (1.0 equiv.) in glacial acetic acid (5 vol.) was added liquid bromine (1.0 equiv.) at 0° C. and reaction mixture was stirred at room temperature for 2 h. The reaction mixture was diluted with water and extracted with ethyl acetate, washed with brine and dried over Na$_2$SO$_4$. The crude product obtained upon concentration was dissolved in dry THF (10 vol.) and thiourea (2.0 equiv.) was added and refluxed overnight. The reaction mixture was diluted with ethyl acetate, washed with sodium thiosulphate solution and organic layer was treated with 1 N HCl to result salt formation of the amine. The precipitated salt was collected by filtration. The salt was then treated with saturated solution of NaHCO$_3$ to regenerate the amine. The mixture was extracted with dichloromethane (2×50 ml) and the combined organic extracts were washed with water and brine. The solvent was evaporated under reduced pressure to afford the 2-amino-4-aryl-thiazole derivative.

Method 2

A solution of acetophenone derivative (1.0 equiv.), thiourea (2.0 equiv.) and iodine (1.0 equiv.) in dry ethanol (5 vol) was refluxed for 24 h. The reaction mixture was diluted with ethyl acetate and the layers were separated. The organic layer was washed with sodium thiosulphate solution to remove iodine. The ethyl acetate solution was treated with 1N HCl and precipitated salt was collected by filtration. The free amine was regenerated as described in Method 1 given above.

All the 2-amino-4-aryl-thiazole derivatives were prepared by either Method 1 or Method 2 starting from appropriate aryl alkyl ketones. Structure information and characterization data for selected intermediates are given in Table 1.

TABLE 1

Structural details and $^1$H NMR data of selected 2-aminothiazole intermediates

| S No | Structure | Mol. Formula (Mol. Wt.) | $^1$H NMR (δ ppm, 300 MHz) |
|---|---|---|---|
| 1. | 2-amino-4-(trifluoromethyl)thiazole | C$_4$H$_3$F$_3$N$_2$S 168.14 | DMSO-d$_6$: 7.26 (s, 1H), 7.42 (br. s, 2H) |
| 2. | 2-amino-4-(4-chlorophenyl)thiazole | C$_9$H$_7$ClN$_2$S 210.68 | DMSO-d$_6$: 7.05 (s, 1H), 7.07 (br. s, 2H), 7.39 (d, J = 7.8 Hz, 2H), 7.78 (d, J = 8.4, 2H) |
| 3. | 2-amino-4-(3-trifluoromethoxyphenyl)thiazole | C$_{10}$H$_6$F$_4$N$_2$S 262.24 | CDCl$_3$: 5.08 (br s, 2H), 6.75 (s, 1H), 7.10 (d, J = 7.8 Hz, 1H), 7.36 (t, J = 7.8 Hz, 1H), 7.61-7.68 (m, 2H) |
| 4. | 2-amino-4-(3-fluoro-4-trifluoromethylphenyl)thiazole | C$_{10}$H$_6$F$_4$N$_2$S 262.23 | DMSO-d$_6$: 7.24 (br. s, 2H), 7.40 (s, 1H), 7.73-7.88 (m, 3H) |
| 5. | 2-amino-4-(4-fluoro-3-trifluoromethylphenyl)thiazole | C$_{10}$H$_6$F$_4$N$_2$S 262.23 | DMSO-d$_6$: 7.20 (br. s, 2H), 7.24 (s, 1H), 7.52 (t, J = 8.7 Hz, 1H), 8.13 (d, J = 6.0 Hz, 2H) |

TABLE 1-continued

Structural details and $^1$H NMR data of selected 2-aminothiazole intermediates

| S No | Structure | Mol. Formula (Mol. Wt.) | $^1$H NMR (δ ppm, 300 MHz) |
|---|---|---|---|
| 6. | 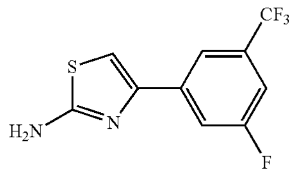 [SMILES: Nc1nc(-c2cc(F)cc(C(F)(F)F)c2)cs1] | $C_{10}H_6F_4N_2S$ 262.23 | DMSO-$d_6$: 7.23 (br s, 2H); 7.41 (s, 1H); 7.55 (d, J = 9.0, 1H); 7.89 (d, J = 10.2, 1H); 7.99 (s, 2H). |
| 7. | 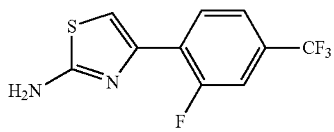 [SMILES: Nc1nc(-c2ccc(C(F)(F)F)cc2F)cs1] | $C_{10}H_6F_4N_2S$ 262.23 | CDCl$_3$: 5.00 (br s, 2H); 7.16 (s, 1H); 7.37 (d, J = 11.7, 1H); 7.44 (d, J = 8.4, 1H); 8.18 (t, J = 7.8, 1H). |
| 8. | 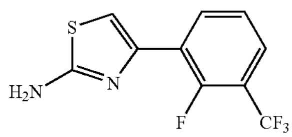 [SMILES: Nc1nc(-c2cccc(C(F)(F)F)c2F)cs1] | $C_{10}H_6F_4N_2S$ 262.23 | CDCl$_3$: 5.04 (br s, 2H), 7.10 (s, 1H), 7.27 (t, J = 7.5 Hz, 1H), 7.51 (t, J = 6.9 Hz, 1H), 8.21-8.28 (m, 1H) |
| 9. | 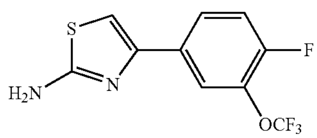 [SMILES: Nc1nc(-c2ccc(F)c(OC(F)(F)F)c2)cs1] | $C_{10}H_6F_4N_2OS$ 278.23 | DMSO-$d_6$: 7.18 (br. s, 3H), 7.50 (t, J = 8.7, 1H), 7.85-7.92 (m, 2H) |
| 10. | 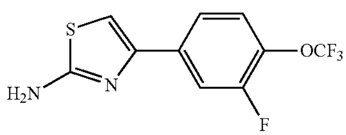 [SMILES: Nc1nc(-c2ccc(OC(F)(F)F)c(F)c2)cs1] | $C_{10}H_6F_4N_2OS$ 278.23 | DMSO-$d_6$: 7.18 (br.s, 2H), 7.24 (s, 1H), 7.55 (d, J = 8.1 Hz, 1H), 7.73 (d, J = 8.7, 1H), 7.80-7.87 (m, 1H) |
| 11. | 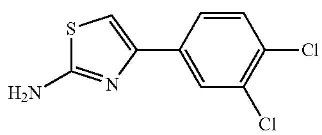 [SMILES: Nc1nc(-c2ccc(Cl)c(Cl)c2)cs1] | $C_9H_6Cl_2N_2S$ 245.13 | CDCl$_3$: 7.85 (s, 1H); 7.56 (dd, J = 8.4, 2.1, 1H); 7.39 (d, J = 8.4, 1H); 6.72 (s, 1H); 5.01 (br.s, 2H). |
| 12. | 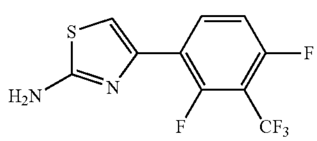 [SMILES: Nc1nc(-c2ccc(F)c(C(F)(F)F)c2F)cs1] | $C_{10}H_5F_5N_2S$ 280.22 | DMSO-$d_6$: 7.05 (s, 1H), 7.21 (br. s, 2H), 7.35-7.48 (m, 1H), 8.21-8.35 (m, 1H) |
| 13. | 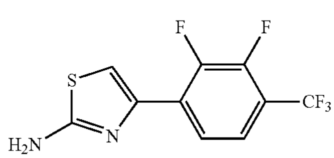 | $C_{10}H_5F_5N_2S$ 280.22 | DMSO-$d_6$: 7.24 (s, 1H), 7.28 (br. s, 2H), 7.65 (t, J = 7.2, 1H), 7.94 (t, J = 7.5, 1H). |
| 14. | 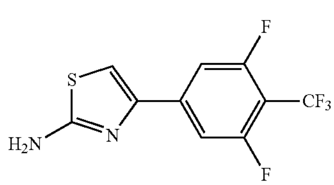 [SMILES: Nc1nc(-c2cc(F)c(C(F)(F)F)c(F)c2)cs1] | $C_{10}H_5F_5N_2S$ 280.22 | DMSO-$d_6$: 7.05 (s, 1H), 7.21 (br. s, 2H), 7.43 (t, J = 9.0 Hz, 1H), 8.35-8.23 (m, 1H) |
| 15. | 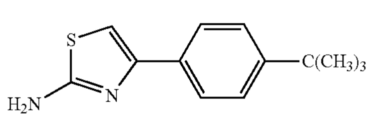 | $C_{13}H_{16}N_2S$ 232.35 | DMSO-$d_6$: 1.28 (s, 9H), 6.89 (s, 1H), 7.01 (br.s, 2H), 7.34 (d, J = 9.0 Hz, 2H), 7.67 (d, J = 8.1 Hz, 2H) |

TABLE 1-continued

Structural details and $^1$H NMR data of selected 2-aminothiazole intermediates

| S No | Structure | Mol. Formula (Mol. Wt.) | $^1$H NMR (δ ppm, 300 MHz) |
|---|---|---|---|
| 16. | 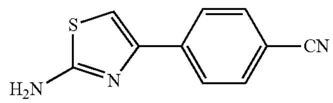 [SMILES: N#Cc1ccc(-c2csc(N)n2)cc1] | $C_{10}H_7N_3S$ 201.25 | DMSO-$d_6$: 7.17 (br. s, 2H), 7.31 (s, 1H), 7.79 (d, J = 8.4, 2H), 7.94 (d, J = 8.4 Hz, 2H) |
| 17. | 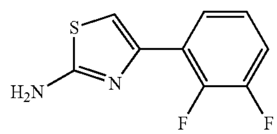 [SMILES: Nc1nc(-c2cccc(F)c2F)cs1] | $C_9H_6F_2N_2S$ 212.22 | CDCl$_3$: 5.06 (br s, 2H), 7.00-7.12 (m, 3H), 7.70-7.78 (m, 1H) |
| 18. | 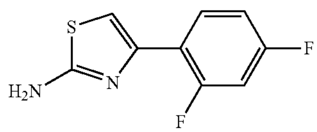 [SMILES: Nc1nc(-c2ccc(F)cc2F)cs1] | $C_9H_6F_2N_2S$ 212.22 | CDCl$_3$: 5.04 (br. s, 2H), 6.80-6.93 (m, 3H), 7.95-8.04 (m, 1H) |
| 19. | 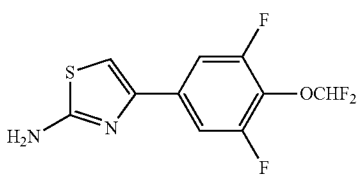 [SMILES: Nc1nc(-c2cc(F)c(OC(F)F)c(F)c2)cs1] | $C_{10}H_6F_4N_2OS$ 278.23 | DMSO-$d_6$: 7.20 (br. s, 2H), 7.24 (t, J = 72.3 Hz, 1H), 7.48 (s, 1H), 7.65 (d, J = 9.0, 2H) |
| 20. | 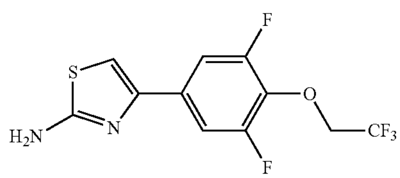 [SMILES: Nc1nc(-c2cc(F)c(OCC(F)(F)F)c(F)c2)cs1] | $C_{11}H_7F_5N_2OS$ 310.24 | DMSO-$d_6$: 4.82 (q, J = 9.0, 2H), 7.16 (br. s, 2H), 7.21 (s, 1H), 7.55 (s, 1H), 7.59 (s, 1H) |
| 21. | 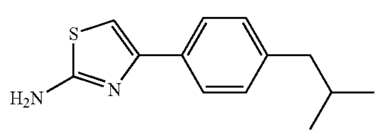 [SMILES: CC(C)Cc1ccc(-c2csc(N)n2)cc1] | $C_{13}F_{16}N_2S$ 232.35 | DMSO-$d_6$: 7.68 (d, J = 7.8, 2H); 7.13 (d, J = 8.1, 2H); 7.03 (br. s, 2H); 6.92 (s, 1H); 2.43 (d, J = 6.9, 2H); 1.86-1.76 (m, 1H); 0.86 (d, J = 6.6, 6H) |

Preparation of 4-[3-Fluoro-4-(trifluoromethyl)phenyl]-1H-imidazol-2-amine

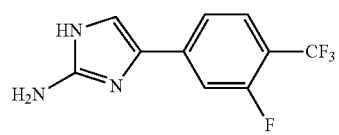 [SMILES: Nc1nc(-c2ccc(C(F)(F)F)c(F)c2)c[nH]1]

Step 1

N-{4-[3-Fluoro-4-(trifluoromethyl)phenyl]-1H-imidazol-2-yl}acetamide: To a stirred solution of 2-bromo-1-[3-fluoro-4-(trifluoromethyl)phenyl]ethanone (4.5 g, 15.73 mmol) in acetonitrile (45 ml) was added acetyl guanidine (2.38 g, 23.60 mmol) at room temperature. After refluxing for 4 h the reaction mixture was cooled to room temperature and diluted with ethyl acetate and water. The layers were separated. The aqueous layer was extracted 2-3 times with ethyl acetate and the combined organic layers were washed with water, followed by brine, dried (Na$_2$SO$_4$) and filtered. The filtrate was concentrated under reduced pressure. The residue obtained after the evaporation of the solvent was purified by silica gel column chromatography using 2% methanol in chloroform to obtain 1.15 g of the product as a yellow solid; $^1$H NMR (300 MHz, DMSO-$d_6$) δ 2.07 (s, 3H), 7.58 (s, 1H), 7.69-7.78 (m, 3H), 11.31 (br s, 1H), 11.91 (br s, 1H).

Step 2

4-[3-Fluoro-4-(trifluoromethyl)phenyl]-1H-imidazol-2-amine: To a stirred solution of Step 1 intermediate (1.1 g, 3.829 mmol) in a mixture of methanol (20 ml) and water (20 ml) was added conc. H$_2$SO$_4$ (2 ml) and the resulting mixture was refluxed for 24 h. Reaction mixture was cooled to room temperature, basified with potassium carbonate solution (pH=10) and extracted with ethyl acetate (2×50 ml). The organic layer was dried (Na$_2$SO$_4$) and filtered. The filtrate was concentrated under reduced pressure. The residue obtained after the evaporation of the solvent was purified by silica gel column chromatography using 5% methanol in chloroform to obtain 290 mg of the product as a yellow solid; $^1$H NMR (300 MHz, DMSO-$d_6$) δ 5.55 (br s, 2H), 7.32 (s, 1H), 7.59-7.67 (m, 3H), 11.30 (br s, 1H).

Preparation of 4-[3-(Trifluoromethoxy)phenyl]-1H-imidazol-2-amine

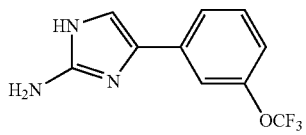

Step 1

N-{4-[3-(trifluoromethoxy)phenyl]-1H-imidazol-2-yl}acetamide: The title compound was prepared according to described procedure using 2-bromo-1-[3-(trifluoromethoxy) phenyl]ethanone (1.7 g, 6.00 mmol) and acetyl guanidine (0.91 g, 9.01 mmol)) in acetonitrile (17 ml) to obtain 460 g of the product as a yellow solid; $^1$H NMR (300 MHz, CDCl$_3$) δ 2.07 (s, 3H), 5.50 (s, 1H), 7.10-7.15 (m, 1H), 7.39 (t, J=7.8, 1H), 7.47-7.64 (m, 3H), 7.92 (s, 1H).

Step 2

4-[3-(Trifluoromethoxy)phenyl]-1H-imidazol-2-amine: The title compound was prepared according to described procedure using Step 1 intermediate (450 mg, 1.578 mmol) in a mixture of methanol-water (22 ml) and conc. H$_2$SO$_4$ (1 ml) to give 130 mg of the product as a yellow solid; $^1$H NMR (300 MHz, DMSO-d$_6$) δ 5.75 (br s, 2H), 7.08 (d, J=8.1, 1H), 7.21 (s, 1H), 7.41 (t, J=7.8, 1H), 7.55-7.64 (m, 2H), 11.30 (br s, 1H).

Preparation of 1-(4-Bromophenyl)-1H-pyrazol-3-amine

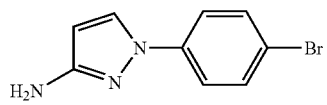 [SMILES: Nc1ccn(-c2ccc(Br)cc2)n1]

The title compound was prepared by the reaction of 4-bromophenylhydrazine with acrylonitrile in the presence of a suitable base such as sodium ethoxide in refluxing ethanol followed by oxidation with N-bromosuccinimide; $^1$H NMR (300 MHz, DMSO-d$_6$) δ 3.81 (br s, 2H), 5.84 (s, 1H), 7.41 (d, J=8.7 Hz, 2H), 7.47 (d, J=8.7 Hz, 2H), 7.63 (s, 1H).

-(4-Bromophenyl)pyrimidin-2-amine was prepared by the reaction of 4-bromoacetophenone with N,N-dimethylformamide dimethyl acetal followed by cyclisation with guanidine hydrochloride in presence of suitable base such as potassium carbonate in refluxing dimethylene glycol monoethyl ether. $^1$H NMR (300 MHz, DMSO-d$_6$) δ 6.69 (br s, 2H), 7.11 (d, J=5.1 Hz, 1H), 7.67 (d, J=8.4 Hz, 2H), 7.99 (d, J=8.1 Hz, 2H), 8.29 (d, J=4.8, 1H. 3-(4-Chlorophenyl)isoxazol-5-amine, 5-(4-bromophenyl)isoxazol-3-amine, 3-(4-chlorophenyl)-1H-pyrazol-5-amine, 5-(4-bromophenyl)-1,3,4-thiadiazol-2-amine were used in the synthesis were commercially available and purchased from Aldrich.

The illustrative examples described herein were synthesized by coupling thienopyrimidine acetic acid derivatives with appropriate aryl amines.

EXAMPLES

General Procedure for the Preparation of Examples

Method A:

To a stirred solution of carboxylic acid derivative (1.0 equiv.) in 1,2-dichloroethane was added EDCI (1.2 equiv.), HOBt (0.3 equiv.) and 4-dimethylaminopyridine (0.1 equiv.) and the mixture was stirred at room temperature for 10-15 min. An appropriate amine (1.0 equiv.) was then added and mixture was stirred at the same temperature for 48 h. The solvent was evaporated under reduced pressure and the residue obtained was diluted with methanol and stirred at room temperature for 30 min. The solid separated out was collected by filtration. The solid product was further purified by recrystalisation from isopropanol or methanol to give the desired products.

Method B:

To a stirred solution of carboxylic acid derivative (1.0 equiv.) in a mixture of tetrahydrofuran and N,N-dimethylformamide (3:1) was added EDCI (2.0 equiv.) and the mixture was stirred for 30 min. An appropriate amine (1.0 equiv.) and DMAP (0.2 equiv.) was added and mixture was maintained at 80° C. under stirring for another 24 h. Most of the tetrahydrofuran is evaporated under reduced pressure and the mixture was acidified to pH 6.0 by addition of 2N hydrochloric acid. The solid precipitated out was collected by filtration. The product was further purified by crystallization or by silica gel column chromatography using methanol-chloroform mixture.

Method C:

To a stirred solution of appropriate thiazole amine (1.2 equiv.) in dry toluene was added sodium hydride and the mixture was stirred at room temperature for 30 min. thienopyrimidine acetic acid ester (1.0 equiv.) was added and the mixture was heated to reflux for overnight. The mixture was cooled and acidified to pH 6.0 by addition of 2N hydrochloric acid. The solid precipitated out was collected by filtration. The product was further purified by crystallization or by silica gel column chromatography using a mixture of methanol and chloroform.

Example 1

2-(1,3-Dimethyl-2,4-dioxo-1,2,3,4-tetrahydrothieno[2,3-d]pyrimidin-5-yl)-N-[4-(trifluoromethyl)-1,3-thiazol-2-yl]acetamide

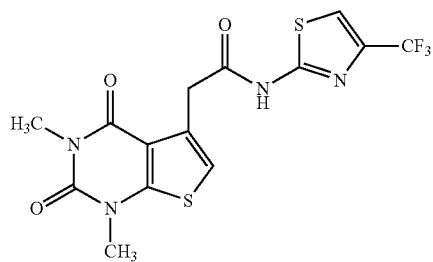 [SMILES: Cn1c(=O)c2c(CC(=O)Nc3nc(C(F)(F)F)cs3)csc2n(C)c1=O]

The title compound was prepared according to the general procedure (Method A) by coupling Intermediate 1 (100 mg, 0.393 mmol) with 4-(trifluoromethyl)-1,3-thiazol-2-amine (66 mg, 0.393 mmol) in the presence of EDCI hydrochloride (90 mg, 0.471 mmol), HOBt (16 mg, 0.118 mmol) and DMAP (5 mg, 0.039 mmol) in 1,2 dichloroethane (4 ml) to give 27 mg of the product as a white solid; ¹H NMR (300 MHz, DMSO-d₆) δ 3.18 (s, 3H), 3.46 (s, 3H), 4.05 (s, 2H), 7.07 (s, 1H), 7.91 (s, 1H), 12.70 (br s, 1H); APCI-MS (m/z) 404.97 (M+H)⁺.

Example 2

N-[4-(4-Chlorophenyl)-1,3-thiazol-2-yl]-2-(1,3-dimethyl-2,4-dioxo-1,2,3,4-tetrahydrothieno[2,3-d]pyrimidin-5-yl)acetamide

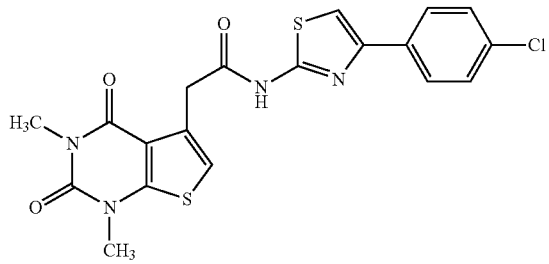 [SMILES: Cn1c(=O)c2c(CC(=O)Nc3nc(-c4ccc(Cl)cc4)cs3)csc2n(C)c1=O]

The title compound was prepared according to the general procedure (Method A) by coupling Intermediate 1 (200 mg, 0.709 mmol) with 4-(4-chlorophenyl)-1,3-thiazol-2-amine (149 mg, 0.709 mmol) in the presence of EDCI hydrochloride (163 mg, 0.851 mmol), HOBt (28 mg, 0.212 mmol) and DMAP (8.60 mg, 0.079 mmol) in 1,2 dichloroethane (4 ml) to give 95 mg of the product as an off-white solid; ¹H NMR (300 MHz, DMSO-d₆) δ 3.19 (s, 3H), 3.47 (s, 3H), 4.06 (s, 2H), 7.07 (s, 1H), 7.50 (d, J=8.4 Hz, 2H), 7.66 (s, 1H), 7.92 (d, J=8.4 Hz, 2H), 12.41 (br s, 1H); APCI-MS (m/z) 445.27 (M+H)⁺.

Example 3

2-(1,3-Dimethyl-2,4-dioxo-1,2,3,4-tetrahydrothieno[2,3-d]pyrimidin-5-yl)-N-{4-[3-(trifluoromethoxy)phenyl]-1,3-thiazol-2-yl}acetamide

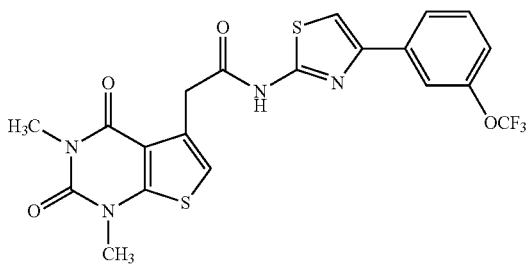 [SMILES: Cn1c(=O)c2c(CC(=O)Nc3nc(-c4cccc(OC(F)(F)F)c4)cs3)csc2n(C)c1=O]

The title compound was prepared according to the general procedure (Method A) by coupling Intermediate 1 (150 mg, 0.590 mmol) with 4-[3-(trifluoromethoxy)phenyl]-1,3-thiazol-2-amine (155 mg, 0.590 mmol) in the presence of EDCI hydrochloride (135 mg, 0.708 mmol), HOBt (24 mg, 0.177 mmol) and DMAP (7.21 mg, 0.059 mmol) in 1,2 dichloroethane (6 ml) to give 40 mg of the product as a white solid; ¹H NMR (300 MHz, DMSO-d₆) δ 3.19 (s, 3H), 3.47 (s, 3H), 4.07 (s, 2H), 7.07 (s, 1H), 7.32 (d, J=7.8 Hz, 1H), 7.58 (t, J=7.8 Hz, 1H), 7.78 (s, 1H), 7.87 (s, 1H), 7.94 (d, J=8.1 Hz, 1H), 12.44 (br s, 1H); ESI-MS (m/z) 497.03 (M+H)⁺.

Example 4

2-(1,3-Dimethyl-2,4-dioxo-1,2,3,4-tetrahydrothieno[2,3-d]pyrimidin-5-yl)-N-[4-(4-isobutylphenyl)-1,3-thiazol-2-yl]acetamide

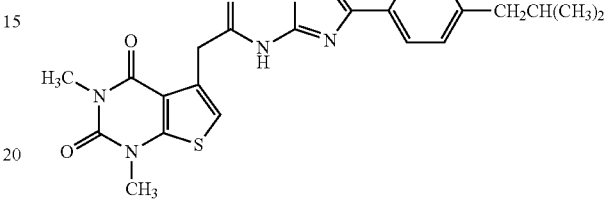

The title compound was prepared according to the general procedure (Method A) by coupling Intermediate 1 (100 mg, 0.393 mmol) with 4-(4-isobutylphenyl)-1,3-thiazol-2-amine (91 mg, 0.393 mmol) in the presence of EDCI hydrochloride (90 mg, 0.472 mmol), HOBt (16 mg, 0.117 mmol) and DMAP (5 mg, 0.039 mmol) in 1,2 dichloroethane (4 ml) to give 42 mg of the product as a white solid; ¹H NMR (300 MHz, CDCl₃) δ 0.88 (d, J=6.3 Hz, 6H), 1.83-1.90 (m, 1H), 2.48 (d, J=6.9 Hz, 2H), 3.51 (s, 3H), 3.57 (s, 3H), 4.06 (s, 2H), 6.88 (s, 1H), 7.04 (s, 1H), 7.16 (d, J=7.8 Hz, 2H), 7.72 (d, J=7.8 Hz, 2H), 10.73 (br s, 1H); APCI-MS (m/z) 469.14 (M+H)⁺.

Example 5

2-(1,3-Dimethyl-2,4-dioxo-1,2,3,4-tetrahydrothieno[2,3-d]pyrimidin-5-yl)-N-{4-[4-fluoro-3-(trifluoromethyl)phenyl]-1,3-thiazol-2-yl}acetamide

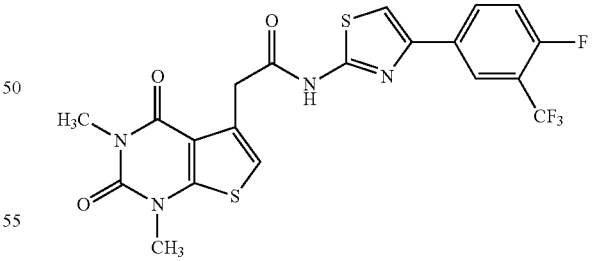

The title compound was prepared according to the general procedure (Method A) by coupling Intermediate 1 (102 mg, 0.401 mmol) with 4-[3-fluoro-4-(trifluoromethyl)phenyl]-1,3-thiazol-2-amine (105 mg, 0.401 mmol) in the presence of EDCI hydrochloride (92 mg, 0.481 mmol), HOBt (16 mg, 0.120 mmol) and DMAP (5 mg, 0.040 mmol) in 1,2 dichloroethane (4 ml) to give 16 mg of the product as a white solid; ¹H NMR (300 MHz, DMSO-d₆) δ 3.19 (s, 3H), 3.47 (s, 3H), 4.07 (s, 2H), 7.07 (s, 1H), 7.83-8.01 (m, 4H), 12.51 (br s, 1H); ESI-MS (m/z) 499.05 (M+H)$^+$.

Example 6

2-(1,3-Dimethyl-2,4-dioxo-1,2,3,4-tetrahydrothieno[2,3-d]pyrimidin-5-yl)-N-{4-[4-fluoro-3-(trifluoromethyl)phenyl]-1,3-thiazol-2-yl}acetamide

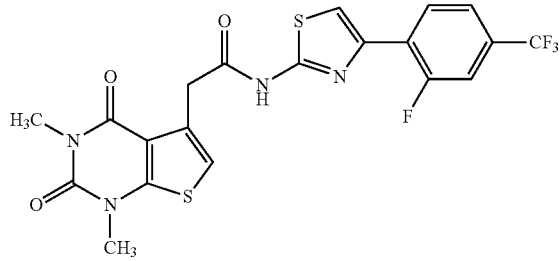 [SMILES: Cn1c(=O)c2c(CC(=O)Nc3nc(-c4ccc(C(F)(F)F)cc4F)cs3)csc2n(C)c1=O]

The title compound was prepared according to the general procedure (Method A) by coupling Intermediate 1 (102 mg, 0.401 mmol) with 4-[4-fluoro-3-(trifluoromethyl)phenyl]-1,3-thiazol-2-amine (105 mg, 0.401 mmol) in the presence of EDCI hydrochloride (92 mg, 0.481 mmol), HOBt (16 mg, 0.120 mmol) and DMAP (5 mg, 0.040 mmol) in 1,2 dichloroethane (4 ml) to give 23 mg of the product as a white solid; $^1$H NMR (300 MHz, DMSO-d$_6$) δ 3.19 (s, 3H), 3.47 (s, 3H), 4.06 (s, 2H), 7.07 (s, 1H), 7.64 (t, J=9.0 Hz, 1H), 7.83 (s, 1H), 8.08-8.36 (m, 2H), 12.48 (br s, 1H); ESI-MS (m/z) 499.10 (M+H)$^+$.

Example 7

2-(1,3-Dimethyl-2,4-dioxo-1,2,3,4-tetrahydrothieno[2,3-d]pyrimidin-5-yl)-N-{4-[2-fluoro-4-(trifluoromethyl)phenyl]-1,3-thiazol-2-yl}acetamide

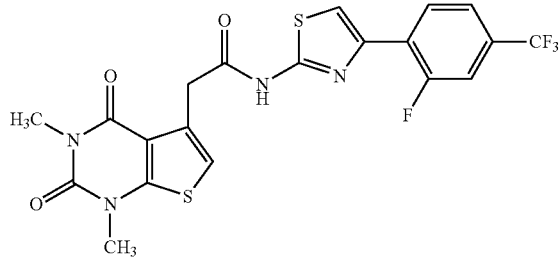 [SMILES: Cn1c(=O)c2c(CC(=O)Nc3nc(-c4ccc(C(F)(F)F)cc4F)cs3)csc2n(C)c1=O]

The title compound was prepared according to the general procedure (Method A) by coupling Intermediate 1 (150 mg, 0.590 mmol) with 4-[2-fluoro-4-(trifluoromethyl)phenyl]-1,3-thiazol-2-amine (155 mg, 0.590 mmol) in the presence of EDCI hydrochloride (135 mg, 0.708 mmol), HOBt (24 mg, 0.177 mmol) and DMAP (7.21 mg, 0.059 mmol) in 1,2 dichloroethane (6 ml) to give 35 mg of the product as a white solid; $^1$H NMR (300 MHz, DMSO-d$_6$) δ 3.19 (s, 3H), 3.47 (s, 3H), 4.08 (s, 2H), 7.08 (s, 1H), 7.70-7.84 (m, 3H), 8.23-8.28 (m, 1H), 12.52 (br s, 1H); APCI-MS (m/z) 497.21 (M+H)$^+$.

Example 8

2-(1,3-Dimethyl-2,4-dioxo-1,2,3,4-tetrahydrothieno[2,3-d]pyrimidin-5-yl)-N-{4-[3-fluoro-5-(trifluoromethyl)phenyl]-1,3-thiazol-2-yl}acetamide

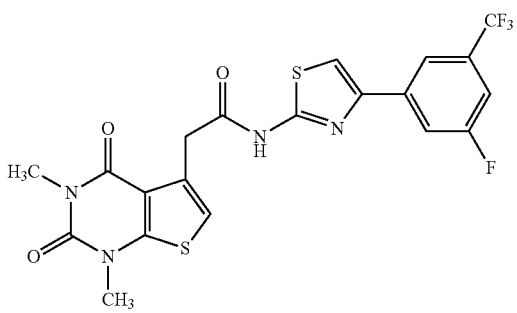 [SMILES: Cn1c(=O)c2c(CC(=O)Nc3nc(-c4cc(F)cc(C(F)(F)F)c4)cs3)csc2n(C)c1=O]

The title compound was prepared according to the general procedure (Method A) by coupling Intermediate 1 (100 mg, 0.393 mmol) with 4-[3-fluoro-5-(trifluoromethyl)phenyl]-1,3-thiazol-2-amine (103 mg, 0.393 mmol) in the presence of EDCI hydrochloride (90 mg, 0.471 mmol), HOBt (16 mg, 0.117 mmol) and DMAP (5 mg, 0.039 mmol) in 1,2 dichloroethane (6 ml) to give 21 mg of the product as a white solid; $^1$H NMR (300 MHz, DMSO-d$_6$) δ 3.19 (s, 3H), 3.47 (s, 3H), 4.07 (s, 2H), 7.07 (s, 1H), 7.64 (d, J=8.1 Hz, 1H), 7.97 (s, 1H), 8.06 (d, J=9.0 Hz, 1H), 8.13 (s, 1H), 12.49 (br s, 1H); APCI-MS (m/z) 497.20 (M−H)$^-$.

Example 9

2-(1,3-Dimethyl-2,4-dioxo-1,2,3,4-tetrahydrothieno[2,3-d]pyrimidin-5-yl)-N-{4-[2-fluoro-3-(trifluoromethyl)phenyl]-1,3-thiazol-2-yl}acetamide

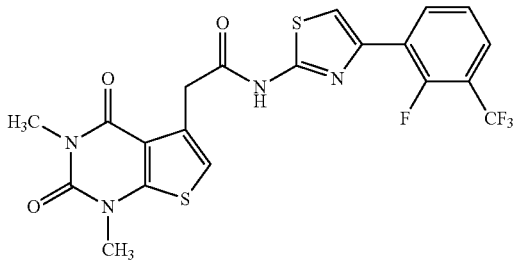 [SMILES: Cn1c(=O)c2c(CC(=O)Nc3nc(-c4cccc(C(F)(F)F)c4F)cs3)csc2n(C)c1=O]

The title compound was prepared according to the general procedure (Method A) by coupling Intermediate 1 (100 mg, 0.393 mmol) with 4-[2-fluoro-3-(trifluoromethyl)phenyl]-1,3-thiazol-2-amine (103 mg, 0.393 mmol) in the presence of EDCI hydrochloride (90 mg, 0.472 mmol), HOBt (16 mg, 0.117 mmol) and DMAP (5 mg, 0.039 mmol) in 1,2 dichloroethane (6 ml) to give 40 mg of the product as an off-white solid; $^1$H NMR (300 MHz, DMSO-d$_6$) δ 3.19 (s, 3H), 3.47 (s, 3H), 4.08 (s, 2H), 7.07 (s, 1H), 7.53 (t, J=7.5 Hz, 1H), 7.66 (s, 1H), 7.77 (t, J=6.9 Hz, 1H), 8.30-8.37 (m, 1H), 12.49 (br s, 1H); APCI-MS (m/z) 499.51 (M+H)⁺.

Example 10

2-(1,3-Dimethyl-2,4-dioxo-1,2,3,4-tetrahydrothieno[2,3-d]pyrimidin-5-yl)-N-{4-[4-fluoro-3-(trifluoromethoxy)phenyl]-1,3-thiazol-2-yl}acetamide

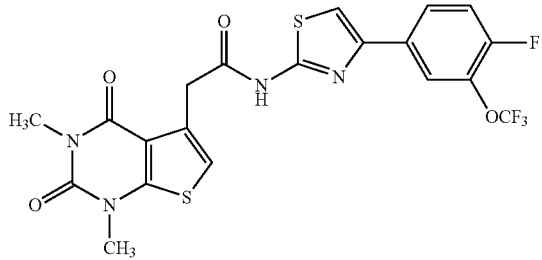

The title compound was prepared according to the general procedure (Method A) by coupling Intermediate 1 (100 mg, 0.393 mmol) with 4-[4-fluoro-3-(trifluoromethoxy)phenyl]-1,3-thiazol-2-amine (109 mg, 0.393 mmol) in the presence of EDCI hydrochloride (90 mg, 0.472 mmol), HOBt (16 mg, 0.118 mmol) and DMAP (5 mg, 0.039 mmol) in 1,2 dichloroethane (4 ml) to give 35 mg of the product as an off-white solid; ¹H NMR (300 MHz, DMSO-d₆) δ 3.19 (s, 3H), 3.47 (s, 3H), 4.06 (s, 2H), 7.07 (s, 1H), 7.59 (t, J=8.7 Hz, 1H), 7.76 (s, 1H), 8.00-8.06 (m, 2H), 12.44 (br s, 1H); APCI-MS (m/z) 513.11 (M−H)⁻.

Example 11

2-(1,3-Dimethyl-2,4-dioxo-1,2,3,4-tetrahydrothieno[2,3-d]pyrimidin-5-yl)-N-{4-[3-fluoro-4-(trifluoromethoxy)phenyl]-1,3-thiazol-2-yl}acetamide

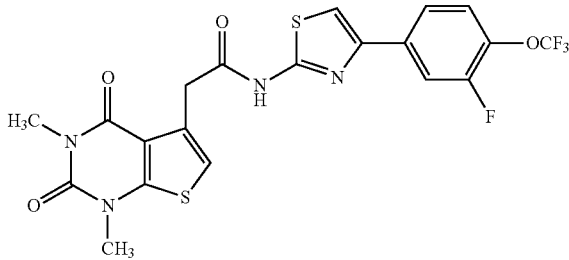 [SMILES: Cn1c(=O)c2c(CC(=O)Nc3nc(-c4ccc(OC(F)(F)F)c(F)c4)cs3)csc2n(C)c1=O]

The title compound was prepared according to the general procedure (Method A) by coupling Intermediate 1 (100 mg, 0.393 mmol) with 4-[3-fluoro-4-(trifluoromethoxy)phenyl]-1,3-thiazol-2-amine (109 mg, 0.393 mmol) in the presence of EDCI hydrochloride (90 mg, 0.471 mmol), HOBt (16 mg, 0.117 mmol) and DMAP (5 mg, 0.039 mmol) in 1,2 dichloroethane (4 ml) to give 35 mg of the product as a white solid; ¹H NMR (300 MHz, DMSO-d₆) δ 3.19 (s, 3H), 3.47 (s, 3H), 4.07 (s, 2H), 7.07 (s, 1H), 7.64 (t, J=8.1 Hz, 1H), 7.80 (s, 1H), 7.85 (d, J=8.7 Hz, 1H), 7.93-8.01 (m, 1H), 12.45 (br s, 1H); APCI-MS (m/z) 515.02 (M+H)⁺.

Example 12

N-[4-(3,4-Dichlorophenyl)-1,3-thiazol-2-yl]-2-(1,3-dimethyl-2,4-dioxo-1,2,3,4-tetrahydrothieno[2,3-d]pyrimidin-5-yl)acetamide

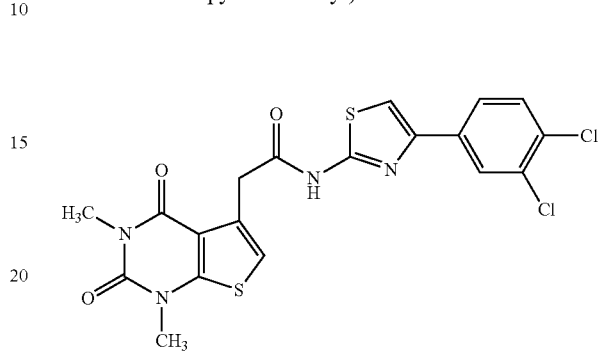

The title compound was prepared according to the general procedure (Method A) by coupling Intermediate 1 (100 mg, 0.393 mmol) with 4-(3,4-dichlorophenyl)-1,3-thiazol-2-amine (96.5 mg, 0.393 mmol) in the presence of EDCI hydrochloride (90 mg, 0.471 mmol), HOBt (16 mg, 0.118 mmol) and DMAP (5 mg, 0.039 mmol) in 1,2 dichloroethane (4 ml) to give 40 mg of the product as a white solid; ¹H NMR (300 MHz, DMSO-d₆) δ 3.19 (s, 3H), 3.47 (s, 3H), 4.06 (s, 2H), 7.07 (s, 1H), 7.70 (d, J=8.4 Hz, 1H), 7.80 (s, 1H), 7.89 (d, J=6.9 Hz, 1H), 8.14 (s, 1H), 12.43 (br s, 1H); APCI-MS (m/z) 479.32 (M−H)⁺.

Example 13

N-{4-[2,4-Difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide

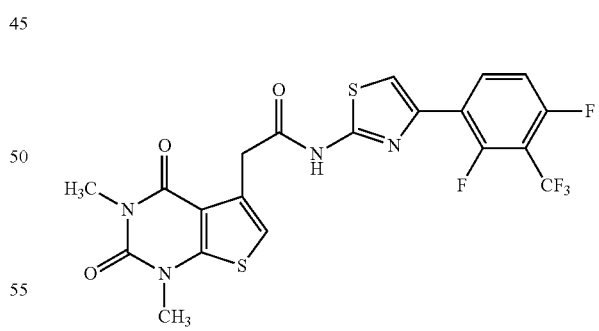

The title compound was prepared according to the general procedure (Method A) by coupling Intermediate 1 (100 mg, 0.393 mmol) with 4-[2,4-difluoro-3-(trifluoromethyl)phenyl]-1,3-thiazol-2-amine (110 mg, 0.393 mmol) in the presence of EDCI hydrochloride (90 mg, 0.471 mmol), HOBt (16 mg, 0.117 mmol) and DMAP (5 mg, 0.039 mmol) in 1,2 dichloroethane (4 ml) to give 20 mg of the product as a white solid; ¹H NMR (300 MHz, DMSO-d₆) δ 3.19 (s, 3H), 3.47 (s, 3H), 4.07 (s, 2H), 7.08 (s, 1H), 7.55 (t, J=9.0 Hz, 1H), 7.62 (s, 1H), 8.34 (q, J=6.9 Hz, 1H), 12.50 (br s, 1H); ESI-MS (m/z) 517.09 (M+H)⁺.

Example 14

[N-{4-[2,4-Difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide] sodium

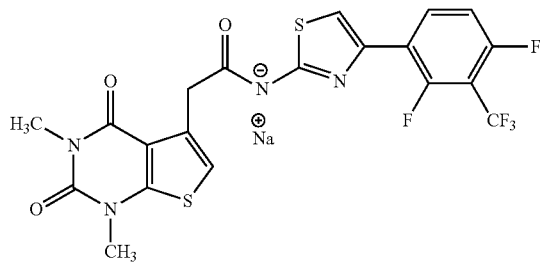 [SMILES: Cn1c(=O)c2c(CC(=O)[N-]c3nc(-c4ccc(F)c(C(F)(F)F)c4F)cs3)csc2n(C)c1=O ; [Na+]]

To a solution of Example 12 (50 mg, 0.096 mmol) in dry THF (1 ml) was added sodium hydride (60% dispersion in mineral oil, 5 mg, 0.106 mmol) at room temperature and stirred for 2 h. The excess of solvent was removed under reduced pressure and solid obtained was washed with hexane (2×5 ml), dry diethyl ether (5 ml) and dried well to give 50 mg of the product as an off-white solid; $^1$H NMR (300 MHz, DMSO-$d_6$) δ 3.23 (s, 3H), 3.46 (s, 3H), 3.81 (s, 2H), 6.89 (s, 1H), 7.04 (s, 1H), 7.40 (t, J=9.6 Hz, 1H), 8.41 (q, J=6.9 Hz, 1H); ESI-MS (m/z) 517.09 (M+H)⁺.

Example 15

N-{4-[2,3-Difluoro-4-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide

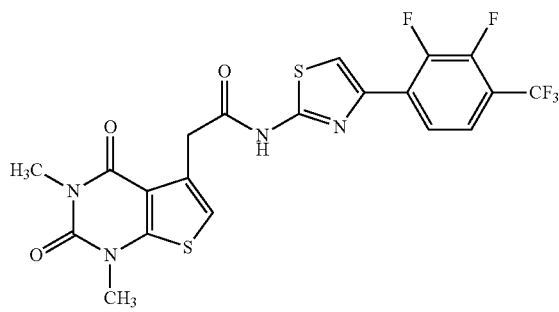 [SMILES: Cn1c(=O)c2c(CC(=O)Nc3nc(-c4ccc(C(F)(F)F)c(F)c4F)cs3)csc2n(C)c1=O]

The title compound was prepared according to the general procedure (Method A) by coupling Intermediate 1 (100 mg, 0.393 mmol) with 4-[2,3-difluoro-4-(trifluoromethyl)phenyl]-1,3-thiazol-2-amine (110 mg, 0.393 mmol) in the presence of EDCI hydrochloride (90 mg, 0.472 mmol), HOBt (16 mg, 0.117 mmol) and DMAP (5 mg, 0.039 mmol) in 1,2 dichloroethane (4 ml) to give 27 mg of the product as an off-white solid; $^1$H NMR (300 MHz, DMSO-$d_6$) δ 3.19 (s, 3H), 3.47 (s, 3H), 4.08 (s, 2H), 7.08 (s, 1H), 7.70-7.80 (m, 2H), 7.98-8.04 (m, 1H), 12.56 (br s, 1H); APCI-MS (m/z) 517.06 (M+H)⁺.

Example 16

N-{4-[3,5-Difluoro-4-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide

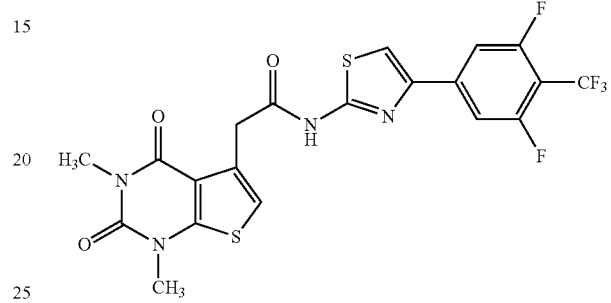

The title compound was prepared according to the general procedure (Method A) by coupling Intermediate 1 (100 mg, 0.393 mmol) with 4-[3,5-difluoro-4-(trifluoromethyl)phenyl]-1,3-thiazol-2-amine (110 mg, 0.393 mmol) in the presence of EDCI hydrochloride (90 mg, 0.472 mmol), HOBt (16 mg, 0.117 mmol) and DMAP (5 mg, 0.039 mmol) in 1,2 dichloroethane (4 ml) to give 30 mg of the product as an off-white solid; $^1$H NMR (300 MHz, DMSO-$d_6$) δ 3.19 (s, 3H), 3.47 (s, 3H), 4.07 (s, 2H), 7.07 (s, 1H), 7.83 (s, 1H), 7.87 (s, 1H), 8.06 (s, 1H), 12.51 (br s, 1H); APCI-MS (m/z) 517.01 (M+H)⁺.

Example 17

N-[4-(4-tert-Butylphenyl)-1,3-thiazol-2-yl]-2-(1,3,6-trimethyl-2,4-dioxo-1,2,3,4-tetrahydrothieno[2,3-d]pyrimidin-5-yl)acetamide

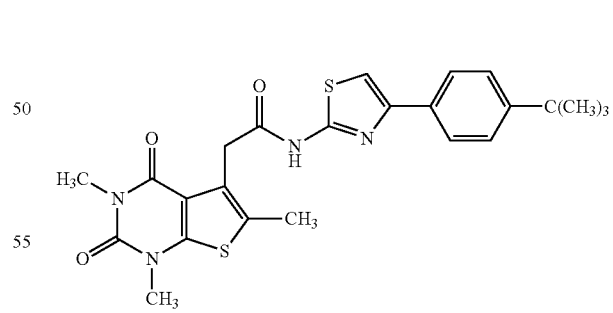

The title compound was prepared according to the general procedure (Method A) by coupling Intermediate 2 (100 mg, 0.373 mmol) with 4-(4-tert-butyl phenyl)-1,3-thiazol-2-amine (86 mg, 0.373 mmol) in the presence of EDCI hydrochloride (85 mg, 0.447 mmol), HOBt (15 mg, 0.111 mmol) and DMAP (5 mg, 0.037 mmol) in 1,2 dichloroethane (4 ml) to give 38 mg of the product as a white solid. $^1$H NMR (300 MHz, DMSO-$d_6$) δ 1.30 (s, 9H), 2.35 (s, 3H), 3.18 (s, 3H), 3.44 (s, 3H), 4.05 (s, 2H), 7.45 (d, J=7.8 Hz, 2H), 7.51 (s, 1H), 7.82 (d, J=7.8 Hz, 2H), 12.39 (s, 1H); APCI-MS (m/z) 483.05 (M+H)$^+$.

Example 18

N-{4-[3-(Trifluoromethoxy)phenyl]-1,3-thiazol-2-yl}-2-(1,3,6-trimethyl-2,4-dioxo-1,2,3,4-tetrahydrothieno[2,3-d]pyrimidin-5-yl)acetamide

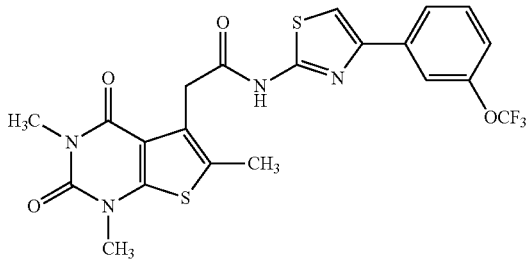 [SMILES: Cc1sc2c(c1CC(=O)Nc1nc(-c3cccc(OC(F)(F)F)c3)cs1)c(=O)n(C)c(=O)n2C]

The title compound was prepared according to the general procedure (Method A) by coupling Intermediate 2 (100 mg, 0.373 mmol) with 4-(3-trifluoromethoxyphenyl)-1,3-thiazol-2-amine (97 mg, 0.373 mmol) in the presence of EDCI hydrochloride (85 mg, 0.447 mmol), HOBt (15 mg, 0.111 mmol) and DMAP (5 mg, 0.037 mmol) in 1,2-dichloroethane (4 ml) to give 21 mg of the product as a white solid. $^1$H NMR (300 MHz, DMSO-d$_6$) δ 2.36 (s, 3H), 3.18 (s, 3H), 3.44 (s, 3H), 4.06 (s, 2H), 7.33 (d, J=7.2 Hz, 1H), 7.58 (t, J=7.8 Hz, 1H), 7.78 (s, 1H), 7.97-7.85 (m, 2H), 12.45 (s, 1H); APCI-MS (m/z) 511.02 (M+H).

Example 19

N-[4-(4-Chlorophenyl)-1,3-thiazol-2-yl]-2-(1,3,6-trimethyl-2,4-dioxo-1,2,3,4-tetrahydrothieno[2,3-d]pyrimidin-5-yl)acetamide

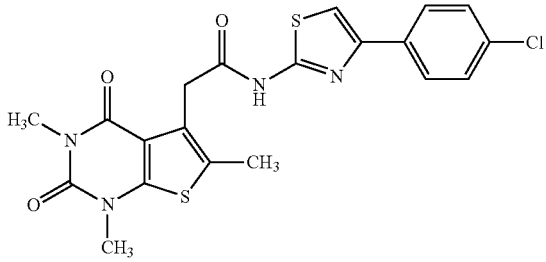 [SMILES: Cc1sc2c(c1CC(=O)Nc1nc(-c3ccc(Cl)cc3)cs1)c(=O)n(C)c(=O)n2C]

The title compound was prepared according to the general procedure (Method A) by coupling Intermediate 2 (200 mg, 0.746 mmol) with 4-(4-chlorophenyl)-1,3-thiazol-2-amine (157 mg, 0.746 mmol) in the presence of EDCI hydrochloride (171 mg, 0.895 mmol), HOBt (30 mg, 0.223 mmol) and DMAP (9.11 mg, 0.074 mmol) in 1,2 dichloroethane (4 ml) to give 13 mg of the product as a yellow solid; $^1$H NMR (300 MHz, DMSO-d$_6$) δ 2.36 (s, 3H), 3.18 (s, 3H), 3.44 (s, 3H), 4.06 (s, 2H), 7.50 (d, J=8.7 Hz, 2H), 7.65 (s, 1H), 7.92 (d, J=8.4 Hz, 2H), 12.40 (br s, 1H); APCI-MS (m/z) 461.11 (M+H)$^+$.

Example 20

N-[4-(3,4-Dichlorophenyl)-1,3-thiazol-2-yl]-2-(1,3,6-trimethyl-2,4-dioxo-1,2,3,4-tetrahydrothieno[2,3-d]pyrimidin-5-yl)acetamide

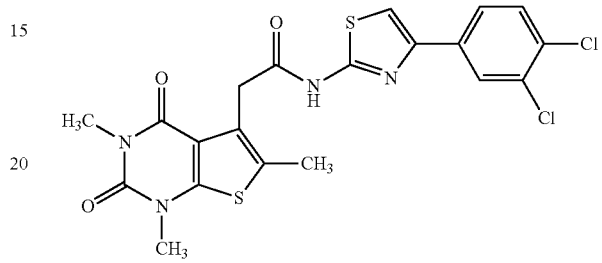

The title compound was prepared according to the general procedure (Method A) by coupling Intermediate 2 (100 mg, 0.373 mmol) with 4-(3,4-dichlorophenyl)-1,3-thiazol-2-amine (91 mg, 0.373 mmol) in the presence of EDCI hydrochloride (85 mg, 0.445 mmol), HOBt (15 mg, 0.111 mmol) and DMAP (5 mg, 0.037 mmol) in 1,2 dichloroethane (3.7 ml) to give 13 mg of the product as a white solid; $^1$H NMR (300 MHz, DMSO-d$_6$) δ 2.36 (s, 3H), 3.18 (s, 3H), 3.44 (s, 3H), 4.06 (s, 2H), 7.71 (d, J=8.1 Hz, 1H), 7.81 (s, 1H), 7.89 (d, J=8.1 Hz, 1H), 8.15 (s, 1H), 12.45 (br s, 1H). APCI-MS (m/z) 495.40 (M+H)$^+$.

Example 21

N-[4-(2,3-Difluorophenyl)-1,3-thiazol-2-yl]-2-(1,3,6-trimethyl-2,4-dioxo-1,2,3,4-tetrahydrothieno[2,3-d]pyrimidin-5-yl)acetamide

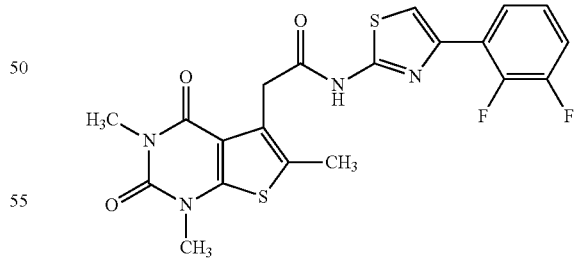

The title compound was prepared according to the general procedure (Method A) by coupling Intermediate 2 (100 mg, 0.373 mmol) with 4-(2,3-difluorophenyl)-1,3-thiazol-2-amine (80 mg, 0.373 mmol) in the presence of EDCI hydrochloride (85 mg, 0.447 mmol), HOBt (15 mg, 0.111 mmol) and DMAP (5 mg, 0.037 mmol) in 1,2-dichloroethane (4 ml) to give 15 mg of the product as an off-white solid; $^1$H NMR (300 MHz, DMSO-d$_6$) 2.36 (s, 3H), 3.18 (s, 3H); 3.44 (s, 3H), 4.06 (s, 2H), 7.28-7.46 (m, 2H), 7.59 (s, 1H), 7.78-7.87 (m, 1H), 12.48 (br s, 1H). APCI-MS (m/z) 510.95 (M+H)⁺.

Example 22

N-[4-(2,4-Difluorophenyl)-1,3-thiazol-2-yl]-2-(1,3,6-trimethyl-2,4-dioxo-1,2,3,4-tetrahydrothieno[2,3-d]pyrimidin-5-yl)acetamide

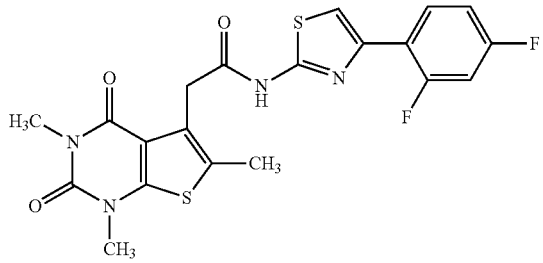 [SMILES: Cc1sc2c(c1CC(=O)Nc1nc(-c3ccc(F)cc3F)cs1)c(=O)n(C)c(=O)n2C]

The title compound was prepared according to the general procedure (Method A) by coupling Intermediate 2 (100 mg, 0.373 mmol) with 4-(2,4-difluorophenyl)-1,3-thiazol-2-amine (97 mg, 0.373 mmol) in the presence of EDCI hydrochloride (85 mg, 0.447 mmol), HOBt (15 mg, 0.111 mmol) and DMAP (4.5 mg, 0.037 mmol) in 1,2-dichloroethane (3 ml) to give 25 mg of the product as a white solid; ¹H NMR (300 MHz, DMSO-$d_6$) δ 2.36 (s, 3H), 3.18 (s, 3H); 3.44 (s, 3H), 4.06 (s, 2H), 7.22 (t, J=6.6 Hz, 1H), 7.33-7.41 (m, 1H), 7.46 (s, 1H), 8.06 (d, J=7.2 Hz, 1H), 12.43 (br s, 1H); ESI-MS (m/z) 463.06 (M+H)⁺.

Example 23

N-{4-[4-Fluoro-3-(trifluoromethyl)phenyl]-1,3-thiazol-2-yl}-2-(1,3,6-trimethyl-2,4-dioxo-1,2,3,4-tetrahydrothieno[2,3-d]pyrimidin-5-yl)acetamide

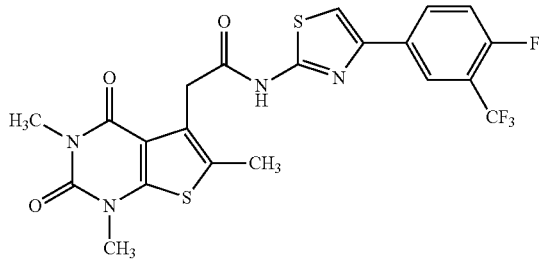 [SMILES: Cc1sc2c(c1CC(=O)Nc1nc(-c3ccc(F)c(C(F)(F)F)c3)cs1)c(=O)n(C)c(=O)n2C]

The title compound was prepared according to the general procedure (Method A) by coupling Intermediate 2 (100 mg, 0.373 mmol) with 4-[4-fluoro-3-(trifluoromethyl)phenyl]-1,3-thiazol-2-amine (97 mg, 0.373 mmol) in the presence of EDCI hydrochloride (85 mg, 0.445 mmol), HOBt (15 mg, 0.111 mmol) and DMAP (4.5 mg, 0.037 mmol) in 1,2 dichloroethane (3.7 ml) to give 28 mg of the product as a white solid; ¹H NMR (300 MHz, DMSO-$d_6$) δ 2.36 (s, 3H), 3.18 (s, 3H), 3.44 (s, 3H), 4.06 (s, 2H), 7.61 (d, J=9.0 Hz, 1H), 7.82 (s, 1H), 8.24-8.30 (m, 2H), 12.47 (br s, 1H); APCI-MS (m/z) 513.09 (M+H)⁺.

Example 24

N-{4-[3-Fluoro-4-(trifluoromethyl)phenyl]-1,3-thiazol-2-yl}-2-(1,3,6-trimethyl-2,4-dioxo-1,2,3,4-tetrahydrothieno[2,3-d]pyrimidin-5-yl)acetamide

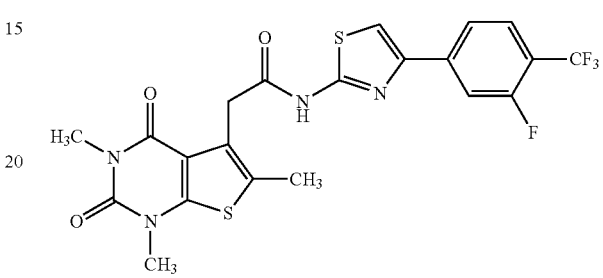

The title compound was prepared according to the general procedure (Method A) by coupling Intermediate 2 (100 mg, 0.373 mmol) with 4-[3-fluoro-4-(trifluoromethyl)phenyl]-1,3-thiazol-2-amine (97 mg, 0.373 mmol) in the presence of EDCI hydrochloride (85 mg, 0.447 mmol), HOBt (15 mg, 0.111 mmol) and DMAP (5 mg, 0.037 mmol) in 1,2 dichloroethane (4 ml) to give 24 mg of the product as a white solid; ¹H NMR (300 MHz, DMSO-$d_6$) δ 2.36 (s, 3H), 3.18 (s, 3H), 3.44 (s, 3H), 4.06 (s, 2H), 8.01-7.85 (m, 4H), 12.49 (s, 1H); APCI-MS (m/z) 513.14 (M+H)⁺.

Example 25

N-{4-[4-Fluoro-3-(trifluoromethoxy)phenyl]-1,3-thiazol-2-yl}-2-(1,3,6-trimethyl-2,4-dioxo-1,2,3,4-tetrahydrothieno[2,3-d]pyrimidin-5-yl)acetamide

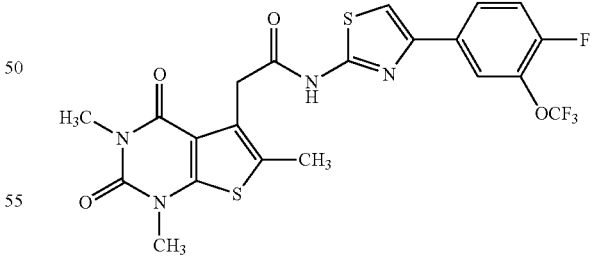

The title compound was prepared according to the general procedure (Method A) by coupling Intermediate 2 (180 mg, 0.671 mmol) with 4-[4-fluoro-3-(trifluoromethoxy)phenyl]-1,3-thiazol-2-amine (187 mg, 0.671 mmol) in the presence of EDCI hydrochloride (154 mg, 0.805 mmol), HOBt (27.2 mg, 0.201 mmol) and DMAP (8.19 mg, 0.0071 mmol) in 1,2 dichloroethane (7 ml) to give 17.5 mg of the product as an off-white solid; ¹H NMR (300 MHz, DMSO-$d_6$) δ 2.35 (s, 3H), 3.18 (s, 3H), 3.44 (s, 3H), 4.06 (s, 2H), 7.58 (t, J=9.0 Hz, 1H), 7.74 (s, 1H), 8.00-8.06 (m, 2H), 12.40 (br s, 1H); APCI-MS (m/z) 529.00 (M+H)+.

Example 26

N-{4-[3-Fluoro-4-(trifluoromethoxy)phenyl]-1,3-thiazol-2-yl}-2-(1,3,6-trimethyl-2,4-dioxo-1,2,3,4-tetrahydrothieno[2,3-d]pyrimidin-5-yl)acetamide

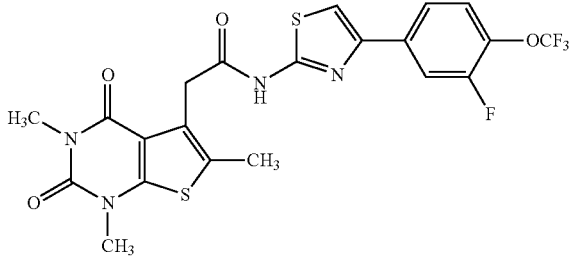 [SMILES: Cc1sc2c(c1CC(=O)Nc1nc(-c3ccc(OC(F)(F)F)c(F)c3)cs1)c(=O)n(C)c(=O)n2C]

The title compound was prepared according to the general procedure (Method A) by coupling Intermediate 2 (180 mg, 0.671 mmol) with 4-[3-fluoro-4-(trifluoromethoxy)phenyl]-1,3-thiazol-2-amine (187 mg, 0.671 mmol) in the presence of EDCI hydrochloride (154 mg, 0.805 mmol), HOBt (27.2 mg, 0.201 mmol) and DMAP (8.19 mg, 0.0071 mmol) in 1,2 dichloroethane (7 ml) to give 54 mg of the product as an off-white solid; $^1$H NMR (300 MHz, DMSO-$d_6$) δ 2.36 (s, 3H), 3.18 (s, 3H), 3.44 (s, 3H), 4.06 (s, 2H), 7.65 (t, J=9.3 Hz, 1H), 7.80 (s, 1H), 7.85 (d, J=8.7 Hz, 1H), 7.98 (d, J=9.0, 1H), 12.47 (br s, 1H); APCI-MS (m/z) 529.06 (M+H)+.

Example 27

N-{4-[2,4-Difluoro-3-(trifluoromethyl)phenyl]-1,3-thiazol-2-yl}-2-(1,3,6-trimethyl-2,4-dioxo-1,2,3,4-tetrahydrothieno[2,3-d]pyrimidin-5-yl)acetamide

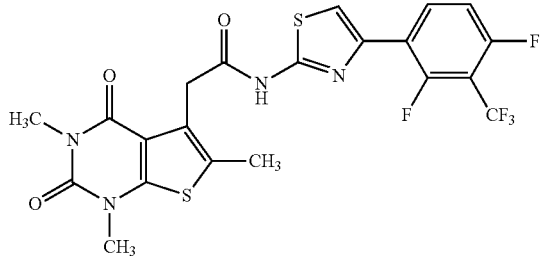 [SMILES: Cc1sc2c(c1CC(=O)Nc1nc(-c3ccc(F)c(C(F)(F)F)c3F)cs1)c(=O)n(C)c(=O)n2C]

The title compound was prepared according to the general procedure (Method B) by coupling Intermediate 2 (150 mg, 0.559 mmol) with 4-(2,4-difluoro-3-(trifluoromethyl)phenyl)-1,3-thiazol-2-amine (156 mg, 0.559 mmol) in the presence of EDCI hydrochloride (214 mg, 1.119 mmol), DMAP (13.5 mg, 0.119 mmol) in the mixture of THF:DMF (3:1, 2.8 ml) to give 27 mg of the product as an off-white solid; $^1$H NMR (300 MHz, CDCl$_3$) δ 2.55 (s, 3H), 3.53 (2s, 6H), 4.04 (s, 2H), 7.07 (t, J=9.0 Hz, 1H), 7.38 (s, 1H), 8.33 (q, J=8.7 Hz, 1H), 10.96 (br s, 1H); APCI-MS (m/z) 513.14 (M+H)+.

Example 28

N-[4-(3-Trifluoromethoxyphenyl)-1H-imidazol-2-yl]-2-(1,3,6-trimethyl-2,4-dioxo-1,2,3,4-tetrahydrothieno[2,3-d]pyrimidin-5-yl)acetamide

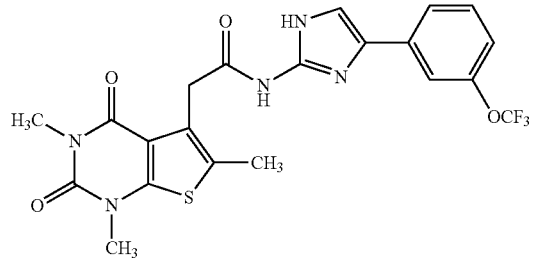 [SMILES: Cc1sc2c(c1CC(=O)Nc1nc(-c3cccc(OC(F)(F)F)c3)c[nH]1)c(=O)n(C)c(=O)n2C]

The title compound was prepared according to the general procedure (Method A) by coupling Intermediate 2 (140 mg, 0.522 mmol) with 4-[3-(trifluoromethoxy)phenyl]-1H-imidazol-2-amine (126 mg, 0.522 mmol) in the presence of EDCI hydrochloride (120 mg, 0.626 mmol), HOBt (21 mg, 0.156 mmol) and DMAP (6.38 mg, 0.052 mmol) in 1,2 dichloroethane (4 ml) to give 30 mg of the product as an off-white solid; $^1$H NMR (300 MHz, DMSO-$d_6$) δ 2.36 (s, 3H), 3.20 (s, 3H), 3.44 (s, 3H), 4.10 (s, 2H), 7.10-7.16 (m, 1H), 7.39-7.50 (m, 2H), 7.68 (s, 1H), 7.72-7.80 (m, 1H), 11.38 (br s, 1H), 11.68 (br s, 1H); APCI-MS (m/z) 494.11 (M+H)+.

Example 29

N-{4-[3-Fluoro-4-(trifluoromethyl)phenyl]-1H-imidazol-2-yl}-2-(1,3,6-trimethyl-2,4-dioxo-1,2,3,4-tetrahydrothieno[2,3-d]pyrimidin-5-yl)acetamide

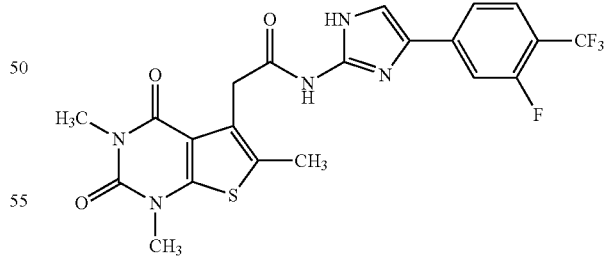

The title compound was prepared according to the general procedure (Method A) by coupling Intermediate 2 (150 mg, 0.559 mmol) with 4-[3-fluoro-4-(trifluoromethyl)phenyl]-1H-imidazol-2-amine (137 mg, 0.559 mmol) in the presence of EDCI hydrochloride (128 mg, 0.671 mmol), HOBt (22 mg, 0.167 mmol) and DMAP (6.83 mg, 0.055 mmol) in 1,2 dichloroethane (6 ml) to give 16.5 mg of the product as an off-white solid; $^1$H NMR (300 MHz, DMSO-$d_6$) δ 2.36 (s, 3H), 3.20 (s, 3H), 3.44 (s, 3H), 3.98 (s, 2H), 7.57 (s, 1H), 7.70-7.80 (m, 3H), 11.40 (br s, 1H), 11.83 (br s, 1H); APCI-MS (m/z) 496.26 (M+H)$^+$.

Example 30

N-[4-(4-Cyanophenyl)-1,3-thiazol-2-yl]-2-(6-ethyl-1,3-dimethyl-2,4-dioxo-1,2,3,4-tetrahydrothieno[2,3-d]pyrimidin-5-yl)acetamide

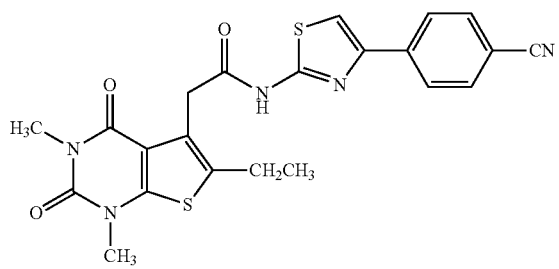 [SMILES: CCc1sc2c(c1CC(=O)Nc1nc(-c3ccc(C#N)cc3)cs1)c(=O)n(C)c(=O)n2C]

The title compound was prepared according to the general procedure (Method A) by coupling Intermediate 3 (150 mg, 0.531 mmol) with 4-(4-cyanophenyl)-1,3-thiazol-2-amine (107 mg, 0.531 mmol) in the presence of EDCI hydrochloride (122 mg, 0.638 mmol), HOBt (21 mg, 0.159 mmol) and DMAP (6.4 mg, 0.053 mmol) in 1,2 dichloroethane (5.3 ml) to give 10 mg of the product as an off-white solid; $^1$H NMR (300 MHz, DMSO-$d_6$) δ 1.19 (t, J=7.5 Hz, 3H), 2.79 (q, J=7.8, 2H), 3.18 (s, 3H), 3.47 (s, 3H), 4.07 (s, 2H), 7.87-7.93 (m, 3H), 8.09 (d, J=8.4 Hz, 2H), 12.48 (br s, 1H); ESI-MS (m/z) 464.31 (M−H)$^-$.

Example 31

N-{4-[3-Fluoro-4-(trifluoromethyl)phenyl]-1,3-thiazol-2-yl}-2-(6-ethyl-1,3-dimethyl-2,4-dioxo-1,2,3,4-tetrahydrothieno[2,3-d]pyrimidin-5-yl)acetamide

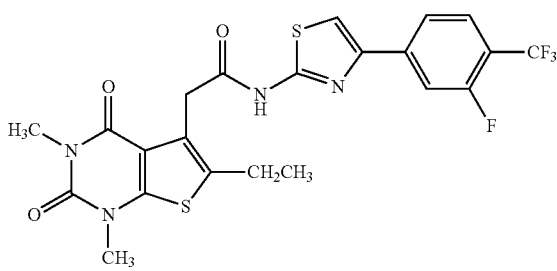 [SMILES: CCc1sc2c(c1CC(=O)Nc1nc(-c3ccc(C(F)(F)F)c(F)c3)cs1)c(=O)n(C)c(=O)n2C]

The title compound was prepared according to the general procedure (Method B) by coupling Intermediate 3 (115 mg, 0.407 mmol) with 4-[3-fluoro-4-(trifluoromethyl)phenyl]-1,3-thiazol-2-amine (106 mg, 0.407 mmol) in the presence of EDCI hydrochloride (156 mg, 0.814 mmol), DMAP (10 mg, 0.081 mmol) in dry THF:DMF (3:1, 14 ml) to give 15 mg of the product as an off-white solid; $^1$H NMR (300 MHz, DMSO-$d_6$) δ 1.19 (t, J=7.5 Hz, 3H), 2.79 (q, J=7.2 Hz, 2H), 3.18 (s, 3H), 3.45 (s, 3H), 4.07 (s, 2H), 7.80-8.04 (m, 4H), 12.51 (br s, 1H). APCI-MS (m/z) 527.09 (M+H)$^+$.

Example 32

N-[4-(2,4-Difluoro-3-trifluoromethyl)phenyl]-1,3-thiazol-2-yl]-2-(6-ethyl-1,3-dimethyl-2,4-dioxo-1,2,3,4-tetrahydrothieno[2,3-d]pyrimidin-5-yl)acetamide

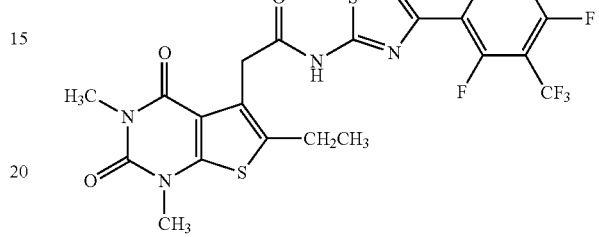

The title compound was prepared according to the general procedure (Method B) by coupling Intermediate 3 (200 mg, 0.709 mmol) with 4-(2,4-difluoro-3-(trifluoromethyl)phenyl)-1,3-thiazol-2-amine (199 mg, 0.709 mmol) in the presence of EDCI hydrochloride (271 mg, 1.41 mmol), DMAP (17 mg, 0.141 mmol) in dry THF:DMF (3:1, 3.54 ml) to give 13 mg of the product as an off-white solid; $^1$H NMR (300 MHz, CDCl$_3$): δ 1.33 (t, J=7.2 Hz, 3H), 2.99 (q, J=8.1 Hz, 2H), 3.40 (s, 3H), 3.52 (s, 3H), 4.03 (s, 2H), 7.07 (d, J=9.0 Hz, 1H), 7.38 (s, 1H), 8.33 (q, J=8.4 Hz, 1H), 10.98 (br s, 1H); APCI-MS (m/z) 545.08 (M+H)$^+$.

Example 33

N-{4-[4-(Difluoromethoxy)-3,5-difluorophenyl]-1,3-thiazol-2-yl}-2-(6-ethyl-1,3-dimethyl-2,4-dioxo-1,2,3,4-tetrahydrothieno[2,3-d]pyrimidin-5-yl)acetamide

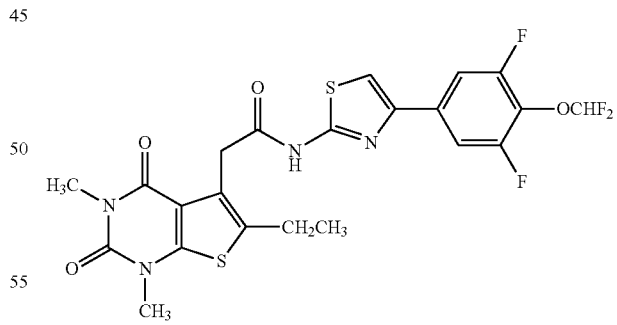

The title compound was prepared according to the general procedure (Method A) by coupling Intermediate 3 (125 mg, 0.443 mmol) with 4-[4-(difluoromethoxy)-3,5-difluorophenyl]-1,3-thiazol-2-amine (123 mg, 0.443 mmol) in the presence of EDCI hydrochloride (102 mg, 0.531 mmol), HOBt (18 mg, 0.132 mmol) and DMAP (5.4 mg, 0.044 mmol) in 1,2 dichloroethane (4.5 ml) to give 18 mg of the product as a white solid; $^1$H NMR (300 MHz, DMSO-$d_6$) δ 1.19 (t, J=7.5 Hz, 3H), 2.78 (q, J=7.5 Hz, 2H), 3.18 (s, 3H), 3.45 (s, 3H), 4.07 (s, 2H), 7.28 (t, J=72.3 Hz, 1H), 7.76-7.87 (m, 3H), 12.47 (br s, 1H); ESI-MS (m/z) 464.31 (M−H)⁻.

Example 34

N-{4-[3,5-Difluoro-4-(2,2,2-trifluoroethoxy)phenyl]-1,3-thiazol-2-yl}-2-(6-ethyl-1,3-dimethyl-2,4-dioxo-1,2,3,4-tetrahydrothieno[2,3-d]pyrimidin-5-yl)acetamide

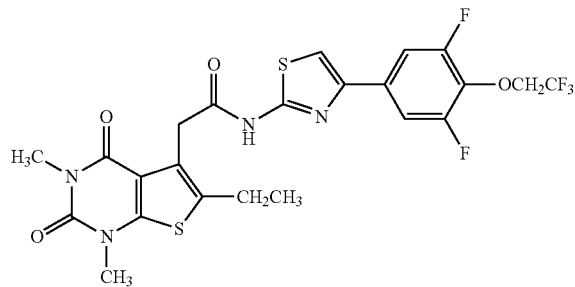

The title compound was prepared according to the general procedure (Method A) by coupling Intermediate 3 (150 mg, 0.531 mmol) with 4-[3,5-difluoro-4-(2,2,2-trifluoroethoxy)phenyl]-1,3-thiazol-2-amine (165 mg, 0.531 mmol) in the presence of EDCI hydrochloride (122 mg, 0.638 mmol), HOBt (21 mg, 0.159 mmol) and DMAP (6.5 mg, 0.053 mmol) in 1,2 dichloroethane (3 ml) to give 60 mg of the product as a white solid; $^1$H NMR (300 MHz, DMSO-$d_6$) δ 1.19 (d, J=7.5 Hz, 3H); 2.78 (q, J=7.8 Hz, 2H), 3.18 (s, 3H), 3.45 (s, 3H), 4.06 (s, 2H), 4.86 (q, J=8.7 Hz, 2H), 7.62-7.79 (m, 3H), 12.45 (br s, 1H); APCI-MS (m/z) 575.75 (M+H)⁺.

Example 35

N-{4-[3-Fluoro-4-(trifluoromethyl)phenyl]-1,3-thiazol-2-yl}-2-(1,3-dimethyl-2,4-dioxo-6-propyl-1,2,3,4-tetrahydrothieno[2,3-d]pyrimidin-5-yl)acetamide

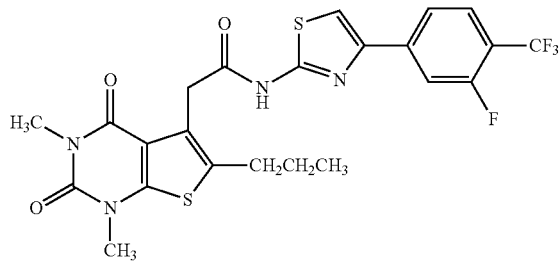

The title compound was prepared according to the general procedure (Method B) by coupling Intermediate 4 (200 mg, 0.674 mmol) with 4-[3-fluoro-4-(trifluoromethyl)phenyl]-1,3-thiazol-2-amine (176 mg, 0.674 mmol) in the presence of EDCI hydrochloride (258 mg, 1.349 mmol), DMAP (16 mg, 0.134 mmol) in dry THF:DMF (3:1, 3.37 ml) to give 12 mg of the product as an off-white solid; $^1$H NMR (300 MHz, CDCl$_3$) δ 0.94-1.04 (m, 3H), 1.54-1.60 (m, 2H), 2.70-2.78 (m, 2H), 3.18 (s, 3H), 3.45 (s, 3H), 4.07 (s, 2H), 7.85-8.00 (m, 4H), 12.47 (br s, 1H); ESI-MS (m/z) 540.85 (M+H)⁺.

Example 36

N-{4-[4-Difluoromethoxy-3,5-difluorophenyl]-1,3-thiazol-2-yl}-2-(1,3-dimethyl-2,4-dioxo-6-propyl-1,2,3,4-tetrahydrothieno[2,3-d]pyrimidin-5-yl)acetamide

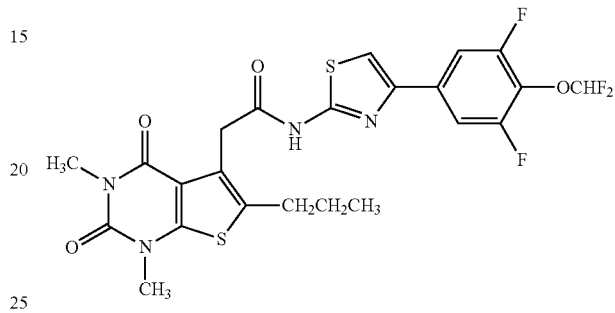

The title compound was prepared according to the general procedure (Method B) by coupling Intermediate 4 (150 mg, 0.506 mmol) with 4-[4-difluoromethoxy-3,5-difluorophenyl]-1,3-thiazol-2-amine (140 mg, 0.506 mmol) in the presence of EDCI hydrochloride (194 mg, 1.012 mmol), DMAP (12.3 mg, 0.101 mmol) in the mixture of THF:DMF (3:1, 2.53 ml) to give 12 mg of the product as an off-white solid; $^1$H NMR (300 MHz, DMSO-$d_6$) δ 1.00-1.06 (m, 3H), 1.45-1.64 (m, 2H), 2.64-2.84 (m, 2H), 3.17 (s, 3H), 3.45 (s, 3H), 4.06 (s, 2H), 7.28 (t, J=73.2 Hz, 1H), 7.75-7.87 (m, 3H), 12.46 (br s, 1H). APCI-MS (m/z) 557.57 (M+H)⁺.

Example 37

N-{4-[3-Fluoro-4-(trifluoromethyl)phenyl]-1,3-thiazol-2-yl}-2-(6-isopropyl-1,3-dimethyl-2,4-dioxo-1,2,3,4-tetrahydrothieno[2,3-d]pyrimidin-5-yl)acetamide

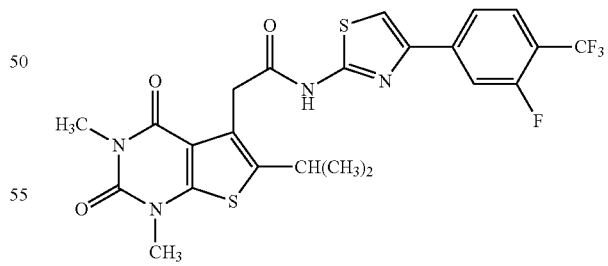

The title compound was prepared according to the general procedure (Method A) by coupling Intermediate 5 (110 mg, 0.371 mmol) with 4-[3-fluoro-4-(trifluoromethyl)phenyl]-1,3-thiazol-2-amine (97 mg, 0.371 mmol) in the presence of EDCI hydrochloride (85 mg, 0.445 mmol), HOBt (15 mg, 0.111 mmol) and DMAP (4.5 mg, 0.037 mmol) in 1,2 dichloroethane (3.7 ml) to give 46 mg of the product as a white solid; $^1$H NMR (300 MHz, DMSO-$d_6$) δ 1.25 (d, J=6.0 Hz, 6H), 3.18 (s, 3H), 3.38-3.43 (m, 1H), 3.46 (s, 3H), 4.10 (s, 2H), 7.86-8.05 (m, 4H), 12.52 (br s, 1H); APCI-MS (m/z) 541.09 (M+H)+.

Example 38

N-[3-(4-Chlorophenyl)isoxazol-5-yl]-2-(1,3-dimethyl-2,4-dioxo-1,2,3,4-tetrahydrothieno[2,3-d]pyrimidin-5-yl)acetamide

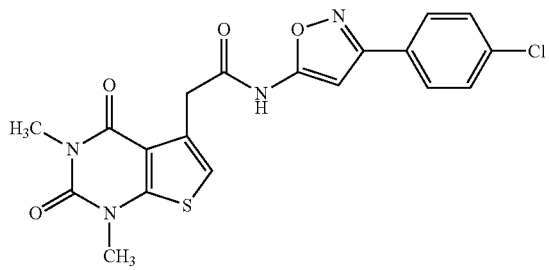 [SMILES: Cn1c(=O)c2c(CC(=O)Nc3cc(-c4ccc(Cl)cc4)no3)csc2n(C)c1=O]

The title compound was prepared according to the general procedure (Method A) by coupling Intermediate 1 (100 mg, 0.393 mmol) with 3-(4-chlorophenyl)isoxazol-5-amine (76 mg, 0.393 mmol) in the presence of EDCI hydrochloride (90 mg, 0.472 mmol), HOBt (16 mg, 0.118 mmol) and DMAP (5 mg, 0.039 mmol) in 1,2 dichloroethane (4 ml) to give 50 mg of the product as an off-white solid; $^1$H NMR (300 MHz, DMSO-$d_6$) δ 3.20 (s, 3H), 3.47 (s, 3H), 4.01 (s, 2H), 6.67 (s, 1H), 7.07 (s, 1H), 7.55 (d, J=8.4 Hz, 2H), 7.85 (d, J=8.4 Hz, 2H), 11.90 (br s, 1H); APCI-MS (m/z) 429.17 (M−H)−.

Example 39

N-[5-(4-Bromophenyl)isoxazol-3-yl]-2-(1,3-dimethyl-2,4-dioxo-1,2,3,4-tetrahydrothieno[2,3-d]pyrimidin-5-yl)acetamide

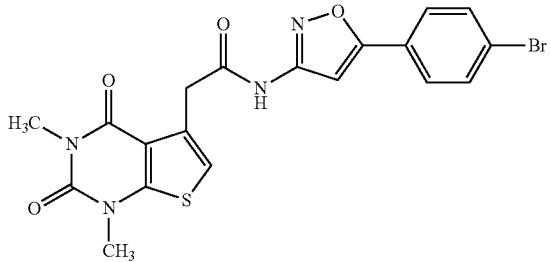 [SMILES: Cn1c(=O)c2c(CC(=O)Nc3cc(-c4ccc(Br)cc4)on3)csc2n(C)c1=O]

The title compound was prepared according to the general procedure (Method A) by coupling Intermediate 1 (100 mg, 0.393 mmol) with 5-(4-bromophenyl)isoxazol-3-amine (94 mg, 0.393 mmol) in the presence of EDCI hydrochloride (90 mg, 0.472 mmol), HOBt (16 mg, 0.118 mmol) and DMAP (5 mg, 0.039 mmol) in 1,2 dichloroethane (4 ml) to give 45 mg of the product as an off-white solid; $^1$H NMR (300 MHz, DMSO-$d_6$) δ 3.20 (s, 3H), 3.47 (s, 3H), 3.99 (s, 2H), 7.05 (s, 1H), 7.33 (s, 1H), 7.72 (d, J=8.1 Hz, 2H), 7.81 (d, J=8.4 Hz, 2H), 11.20 (br s, 1H); APCI-MS (m/z) 475.01 (M+H).

Example 40

N-[1-(4-Bromophenyl)-1H-pyrazol-3-yl]-2-(1,3-dimethyl-2,4-dioxo-1,2,3,4-tetrahydrothieno[2,3-d]pyrimidin-5-yl)acetamide

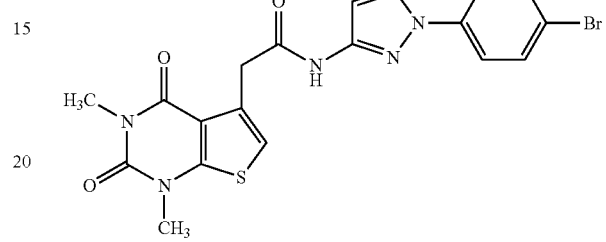

The title compound was prepared according to the general procedure (Method A) by coupling Intermediate 1 (100 mg, 0.393 mmol) with 1-(4-bromophenyl)-1H-pyrazol-3-amine (93.5 mg, 0.393 mmol) in the presence of EDCI hydrochloride (90 mg, 0.472 mmol), HOBt (16 mg, 0.118 mmol) and DMAP (5 mg, 0.039 mmol) in 1,2 dichloroethane (6 ml) to give 45 mg of the product as an off-white solid; $^1$H NMR (300 MHz, DMSO-$d_6$) δ 3.21 (s, 3H), 3.46 (s, 3H), 3.95 (s, 2H), 6.75 (s, 1H), 7.02 (s, 1H), 7.67 (d, J=8.7 Hz, 2H), 7.74 (d, J=9.0 Hz, 2H), 8.41 (s, 1H), 10.82 (br s, 1H); APCI-MS (m/z) 475.95 (M+H)+.

Example 41

N-[3-(4-Chlorophenyl)-1H-pyrazol-5-yl]-2-(1,3-dimethyl-2,4-dioxo-1,2,3,4-tetrahydrothieno[3,4-d]pyrimidin-5-yl)acetamide

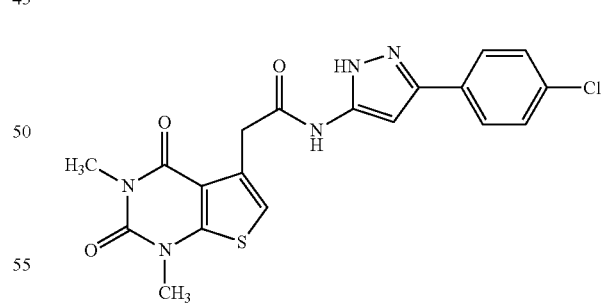

The title compound was prepared according to the general procedure (Method A) by coupling Intermediate 1 (100 mg, 0.393 mmol) with 3-(4-chlorophenyl)-1H-pyrazol-5-amine (76 mg, 0.393 mmol) in the presence of EDCI hydrochloride (90 mg, 0.471 mmol), HOBt (16 mg, 0.117 mmol) and DMAP (5 mg, 0.039 mmol) in 1,2 dichloroethane (6 ml) to give 36 mg of the product as an off-white solid; $^1$H NMR (300 MHz, DMSO-$d_6$) δ 3.22 (s, 3H), 3.46 (s, 3H), 3.93 (s, 2H), 6.86 (s, 1H), 7.01 (s, 1H), 7.50 (d, J=8.4, 1H), 7.70 (d, J=8.1, 1H), 10.51 (s, 1H), 12.86 (br s, 1H); ESI-MS (m/z) 428.22 (M−H)⁻.

Example 42

N-[5-(4-Bromophenyl)-1,3,4-thiadiazol-2-yl]-2-(1,3-dimethyl-2,4-dioxo-1,2,3,4-tetrahydrothieno[2,3-d]pyrimidin-5-yl)acetamide

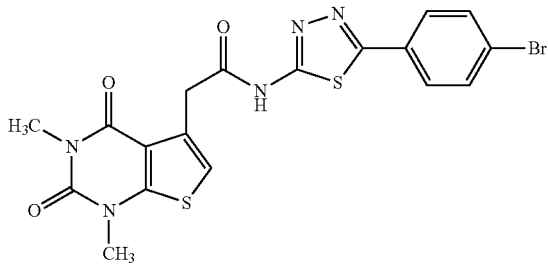 [SMILES: Cn1c(=O)c2c(CC(=O)Nc3nnc(-c4ccc(Br)cc4)s3)csc2n(C)c1=O]

The title compound was prepared according to the general procedure (Method A) by coupling Intermediate 1 (100 mg, 0.393 mmol) with 5-(4-bromophenyl)-1,3,4-thiadiazol-2-amine (101 mg, 0.393 mmol) in the presence of EDCI hydrochloride (90 mg, 0.472 mmol), HOBt (16 mg, 0.118 mmol) and DMAP (5 mg, 0.039 mmol) in 1,2 dichloroethane (4 ml) to give 45 mg of the product as an off-white solid; ¹H NMR (300 MHz, DMSO-$d_6$) δ 3.18 (s, 3H), 3.47 (s, 3H), 4.11 (s, 2H), 7.09 (s, 1H), 7.72 (d, J=8.4 Hz, 2H), 7.87 (d, J=8.1 Hz, 2H), 12.85 (br s, 1H); APCI-MS (m/z) 493.93 (M+H)⁺.

Example 43

N-[4-(4-Bromophenyl)pyrimidin-2-yl]-2-(1,3-dimethyl-2,4-dioxo-1,2,3,4-tetrahydrothieno[2,3-d]pyrimidin-5-yl)acetamide

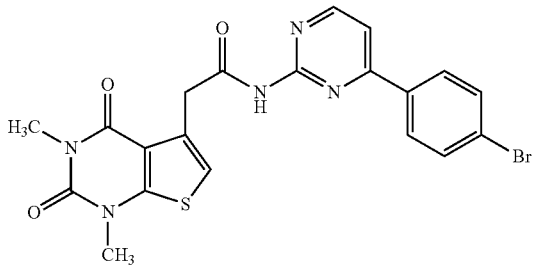 [SMILES: Cn1c(=O)c2c(CC(=O)Nc3nccc(-c4ccc(Br)cc4)n3)csc2n(C)c1=O]

The title compound was prepared according to the general procedure (Method A) by coupling Intermediate 1 (100 mg, 0.393 mmol) with 4-(4-bromophenyl)pyrimidin-2-amine (98 mg, 0.393 mmol) in the presence of EDCI hydrochloride (90 mg, 0.472 mmol), HOBt (16 mg, 0.118 mmol) and DMAP (5 mg, 0.039 mmol) in 1,2 dichloroethane (4 ml) to give 28 mg of the product as an off-white solid; ¹H NMR (300 MHz, CF₃CO₂D) δ 3.57 (s, 3H), 3.77 (s, 3H), 4.45 (s, 2H), 7.18 (s, 1H), 7.80-7.86 (m, 2H), 8.06-8.18 (m, 3H), 8.64-8.70 (m, 1H); APCI-MS (m/z) 485.96 (M)⁺.

Example 44

2-(1,3-Dimethyl-2,4-dioxo-1,2,3,4-tetrahydrothieno[3,4-d]pyrimidin-5-yl)-N-[4-(4-isobutylphenyl)-1,3-thiazol-2-yl]acetamide

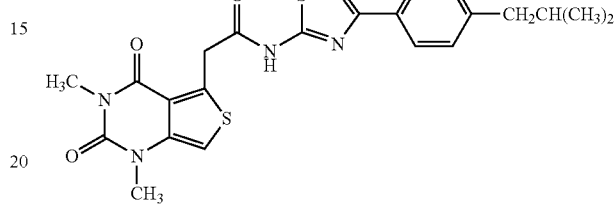

The title compound was prepared according to the general procedure (Method C) by coupling Intermediate 6 (150 mg, 0.531 mmol) with 4-(4-isobutylphenyl)-1,3-thiazol-2-amine (148 mg, 0.638 mmol) in the presence of sodium hydride (60% dispersion in mineral oil, 43 mg, 1.062 mmol) in dry toluene (6 ml) to give 17 mg of the product as an off-white solid; ¹H NMR (300 MHz, DMSO-$d_6$) δ 0.90 (d, J=6.9 Hz, 6H), 1.82-1.92 (m, 1H), 2.48 (d, J=7.5 Hz, 2H), 3.48 (s, 1H), 3.49, (s, 3H), 4.40 (s, 2H), 6.48 (s, 1H), 7.06 (s, 1H), 7.17 (d, J=7.8 Hz, 2H), 7.73 (d, J=7.8 Hz, 2H), 10.57 (br s, 1H); APCI-MS (m/z) 469.20 (M+H)⁺.

Example 45

N-[4-(4-Chlorophenyl)-1,3-thiazol-2-yl]-2-(1,3-dimethyl-2,4-dioxo-1,2,3,4-tetrahydrothieno[3,4-d]pyrimidin-5-yl)acetamide

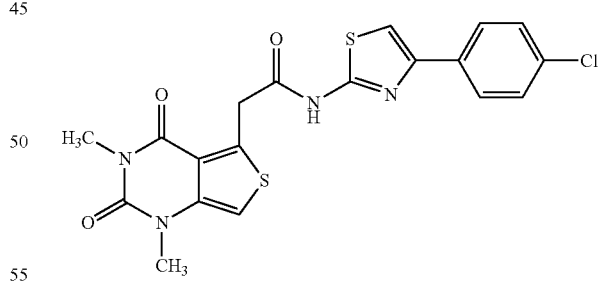

The title compound was prepared according to the general procedure (Method C) by coupling Intermediate 6 (150 mg, 0.531 mmol) with 4-(4-chlorophenyl)-1,3-thiazol-2-amine (133 mg, 0.637 mmol) in the presence of sodium hydride (60% dispersion in mineral oil, 43 mg, 1.062 mmol) in dry toluene (6 ml) to give 90 mg of the product as an off-white solid; ¹H NMR (300 MHz, DMSO-$d_6$) δ 3.19 (s, 3H), 3.38 (s, 3H), 4.55 (s, 2H), 7.01 (s, 1H), 7.49 (d, J=8.4, 2H), 7.68 (s, 1H), 7.93 (d, J=7.8 Hz, 2H), 12.59 (br s, 1H); APCI-MS (m/z) 447.09 (M+H)⁺.

Example 46

2-(1,3-Dimethyl-2,4-dioxo-1,2,3,4-tetrahydrothieno[3,4-d]pyrimidin-5-yl)-N-[4-(3-trifluoromethyl)phenyl]-1,3-thiazol-2-yl]acetamide

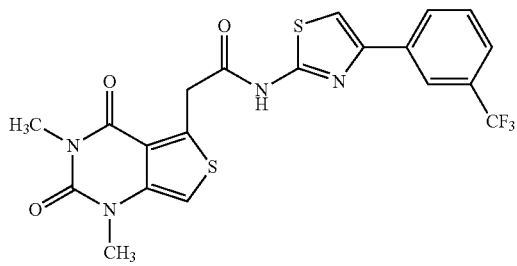 [SMILES: Cn1c(=O)c2c(CC(=O)Nc3nc(-c4cccc(C(F)(F)F)c4)cs3)scc2n(C)c1=O]

The title compound was prepared according to the general procedure (Method C) by coupling Intermediate 6 (150 mg, 0.531 mmol) with 4-[3-(trifluoromethyl)phenyl]-1,3-thiazol-2-amine (155 mg, 0.638 mmol) in the presence of sodium hydride (60% dispersion in mineral oil, 43 mg, 1.062 mmol) in dry toluene (6 ml) to give 42 mg of the product as an off-white solid; $^1$H NMR (300 MHz, DMSO-$d_6$) δ 3.19 (s, 3H), 3.39 (s, 3H), 4.55 (s, 2H), 7.02 (s, 1H), 7.65-7.72 (m, 2H), 7.88 (s, 1H), 8.20-8.26 (m, 2H), 12.66 (br s, 1H); APCI-MS (m/z) 481.05 (M+H)$^+$.

Example 47

2-(1,3-Dimethyl-2,4-dioxo-1,2,3,4-tetrahydrothieno[3,4-d]pyrimidin-5-yl)-N-[4-(4-trifluoromethyl)phenyl]-1,3-thiazol-2-yl]acetamide

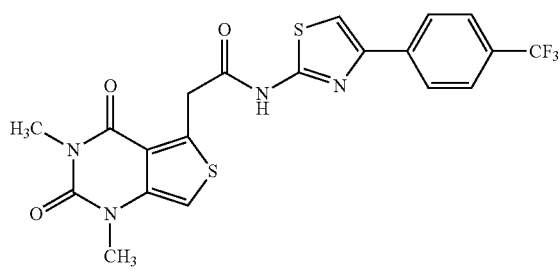

The title compound was prepared according to the general procedure (Method C) by coupling Intermediate 6 (150 mg, 0.531 mmol) with 4-[4-(trifluoromethyl)phenyl]-1,3-thiazol-2-amine (155 mg, 0.638 mmol) in the presence of sodium hydride (60% dispersion in mineral oil, 43 mg, 1.062 mmol) in dry toluene (6 ml) to give 23 mg of the product as an off-white solid; $^1$H NMR (300 MHz, DMSO-$d_6$) δ 3.20 (s, 3H), 3.40 (s, 3H), 4.56 (s, 2H), 7.03 (s, 1H), 7.81 (d, J=8.1, 2H), 7.86 (s, 1H), 8.12 (d, J=8.4, 2H), 12.66 (br s, 1H); APCI-MS (m/z) 481.11 (M+H)$^+$.

Example 48

2-(1,3-Dimethyl-2,4-dioxo-1,2,3,4-tetrahydrothieno[3,4-d]pyrimidin-5-yl)-N-{4-[3-(trifluoromethoxy)phenyl]-1,3-thiazol-2-yl}acetamide

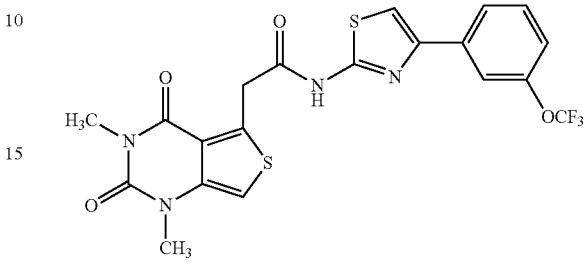

The title compound was prepared according to the general procedure (Method C) by coupling Intermediate 6 (150 mg, 0.531 mmol) with 4-[3-(trifluoromethoxy)phenyl]-1,3-thiazol-2-amine (165 mg, 0.638 mmol) in the presence of sodium hydride (60% dispersion in mineral oil, 43 mg, 1.062 mmol) in dry toluene (6 ml) to give 240 mg of the product as an off-white solid; $^1$H NMR (300 MHz, DMSO-$d_6$) δ 3.19 (s, 3H), 3.40 (s, 3H), 4.55 (s, 2H), 7.03 (s, 1H), 7.33 (d, J=8.4 Hz, 1H), 7.58 (t, J=7.8 Hz, 1H), 7.81 (s, 1H), 7.87 (s, 1H), 7.95 (d, J=8.4 Hz, 1H), 12.63 (br s, 1H); APCI-MS (m/z) 497.09 (M+H)$^+$.

Example 49

2-(1,3-Dimethyl-2,4-dioxo-1,2,3,4-tetrahydrothieno[3,4-d]pyrimidin-5-yl)-N-{4-[4-fluoro-3-(trifluoromethyl)phenyl]-1,3-thiazol-2-yl}acetamide

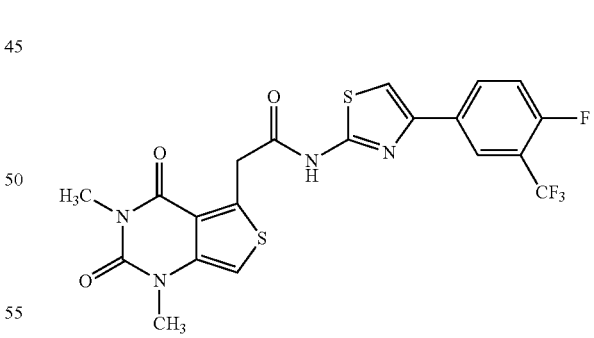

The title compound was prepared according to the general procedure (Method C) by coupling Intermediate 6 (150 mg, 0.531 mmol) with 4-[4-fluoro-3-(trifluoromethyl)phenyl]-1,3-thiazol-2-amine (167 mg, 0.638 mmol) in the presence of sodium hydride (60% dispersion in mineral oil, 43 mg, 1.062 mmol) in dry toluene (6 ml) to give 90 mg of the product as an off-white solid; $^1$H NMR (300 MHz, DMSO-$d_6$) δ 3.19 (s, 3H), 3.39 (s, 3H), 4.55 (s, 2H), 7.03 (s, 1H), 7.61 (t, J=9.0 Hz, 1H), 7.86 (s, 1H), 8.24-8.30 (m, 2H), 12.66 (br s, 1H); APCI-MS (m/z) 499.00 (M+H)+.

Example 50

2-(1,3-Dimethyl-2,4-dioxo-1,2,3,4-tetrahydrothieno[3,4-d]pyrimidin-5-yl)-N-{4-[3-fluoro-4-(trifluoromethyl)phenyl]-1,3-thiazol-2-yl}acetamide

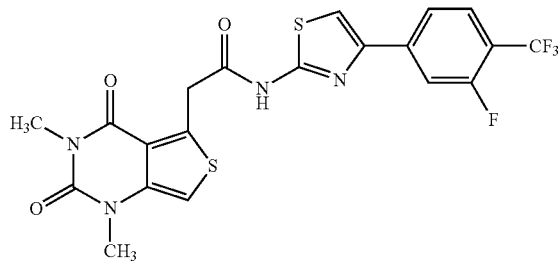 [SMILES: Cn1c(=O)c2c(CC(=O)Nc3nc(-c4ccc(C(F)(F)F)cc4)cs3)scc2n(C)c1=O]

The title compound was prepared according to the general procedure (Method C) by coupling Intermediate 6 (150 mg, 0.531 mmol) with 4-[3-fluoro-4-(trifluoromethyl)phenyl]-1,3-thiazol-2-amine (167 mg, 0.638 mmol) in the presence of sodium hydride (60% dispersion in mineral oil, 43 mg, 1.062 mmol) in dry toluene (6 ml) to give 68 mg of the product as an off-white solid; $^1$H NMR (300 MHz, DMSO-$d_6$) δ 3.19 (s, 3H), 3.39 (s, 3H), 4.56 (s, 2H), 7.03 (s, 1H), 7.83-7.97 (m, 3H), 7.99 (s, 1H), 12.68 (br s, 1H); APCI-MS (m/z) 499.09 (M+H)+.

Example 51

2-(1,3-Dimethyl-2,4-dioxo-1,2,3,4-tetrahydrothieno[3,4-d]pyrimidin-5-yl)-N-{4-[2-fluoro-4-(trifluoromethyl)phenyl]-1,3-thiazol-2-yl}acetamide

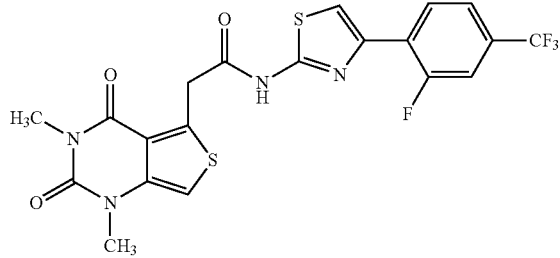 [SMILES: Cn1c(=O)c2c(CC(=O)Nc3nc(-c4ccc(C(F)(F)F)cc4F)cs3)scc2n(C)c1=O]

The title compound was prepared according to the general procedure (Method C) by coupling Intermediate 6 (90 mg, 0.319 mmol) with 4-[2-fluoro-4-(trifluoromethyl)phenyl]-1,3-thiazol-2-amine (100 mg, 0.382 mmol) in the presence of sodium hydride (60% dispersion in mineral oil, 25 mg, 0.638 mmol) in dry toluene (4 ml) to give 150 mg of the product as a white solid; $^1$H NMR (300 MHz, DMSO-$d_6$) δ 3.20 (s, 3H), 3.39 (s, 3H), 4.55 (s, 2H), 7.02 (s, 1H), 7.68-7.82 (m, 3H), 8.27 (t, J=7.8 Hz, 1H), 12.46 (br s, 1H); APCI-MS (m/z) 499.05 (M+H)+.

Example 52

2-(1,3-Dimethyl-2,4-dioxo-1,2,3,4-tetrahydrothieno[3,4-d]pyrimidin-5-yl)-N-{4-[3-fluoro-4-(trifluoromethoxy)phenyl]-1,3-thiazol-2-yl}acetamide

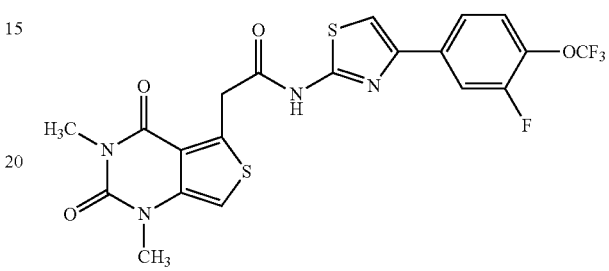

The title compound was prepared according to the general procedure (Method C) by coupling Intermediate 6 (150 mg, 0.531 mmol) with 4-[3-fluoro-4-(trifluoromethoxy)phenyl]-1,3-thiazol-2-amine (177 mg, 0.638 mmol) in the presence of sodium hydride (60% dispersion in mineral oil, 43 mg, 1.062 mmol) in dry toluene (6 ml) to give 35 mg of the product as an off-white solid; $^1$H NMR (300 MHz, DMSO-$d_6$) δ 3.19 (s, 3H), 3.39 (s, 3H), 4.56 (s, 2H), 7.03 (s, 1H), 7.67 (t, J=7.8 Hz, 1H), 7.82-7.89 (m, 2H), 7.98 (d, J=9.0 Hz, 1H), 12.65 (br s, 1H); APCI-MS (m/z) 515.18 (M+H)+.

Example 53

N-[4-(3,4-Dichlorophenyl)-1,3-thiazol-2-yl]-2-(1,3-dimethyl-2,4-dioxo-1,2,3,4-tetrahydrothieno[3,4-d]pyrimidin-5-yl)acetamide

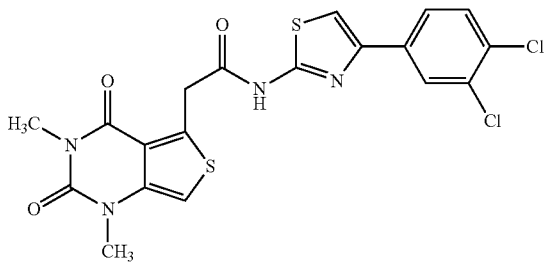

The title compound was prepared according to the general procedure (Method C) by coupling Intermediate 6 (150 mg, 0.531 mmol) with 4-(3,4-dichlorophenyl)-1,3-thiazol-2-amine (156 mg, 0.638 mmol) in the presence of sodium hydride (60% dispersion in mineral oil, 43 mg, 1.062 mmol) in dry toluene (6 ml) to give 15 mg of the product as an off-white solid; $^1$H NMR (300 MHz, DMSO-$d_6$) δ 3.19 (s, 3H), 3.39 (s, 3H), 4.55 (s, 2H), 7.03 (s, 1H), 7.71 (d, J=8.4 Hz, 1H), 7.84 (s, 1H), 7.89 (d, J=6.6 Hz, 1H), 12.65 (br s, 1H); APCI-MS (m/z) 481.07 (M+H)⁺.

Example 54

2-(1,3-Dimethyl-2,4-dioxo-1,2,3,4-tetrahydrothieno[3,4-d]pyrimidin-5-yl)-N-{4-[3-fluoro-5-(trifluoromethyl)phenyl]-1,3-thiazol-2-yl}acetamide

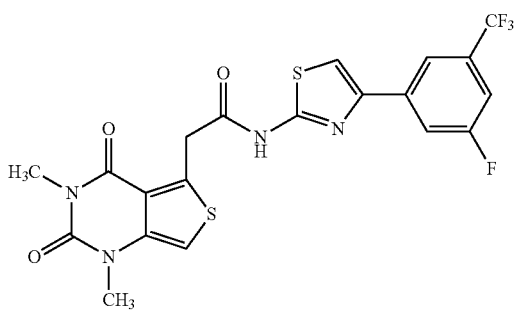 [SMILES: Cn1c(=O)c2c(CC(=O)Nc3nc(-c4cc(F)cc(C(F)(F)F)c4)cs3)scc2n(C)c1=O]

The title compound was prepared according to the general procedure (Method C) by coupling Intermediate 6 (150 mg, 0.531 mmol) with 4-[3-fluoro-5-(trifluoromethyl)phenyl]-1,3-thiazol-2-amine (167.8 mg, 0.638 mmol) in the presence of sodium hydride (60% dispersion in mineral oil, 43 mg, 1.062 mmol) in dry toluene (6 ml) to give 13 mg of the product as a white solid; $^1$H NMR (300 MHz, DMSO-d$_6$) δ 3.19 (s, 3H), 3.39 (s, 3H), 4.56 (s, 2H), 7.03 (s, 1H), 7.65 (d, J=8.4, 1H), 8.01 (s, 1H), 8.06 (d, J=10.2 Hz, 1H), 8.13 (s, 1H), 12.68 (br s, 1H); APCI-MS (m/z) 499.07 (M+H)⁺.

Example 55

2-(1,3-Dimethyl-2,4-dioxo-1,2,3,4-tetrahydrothieno[3,4-d]pyrimidin-5-yl)-N-{4-[4-fluoro-3-(trifluoromethoxy)phenyl]-1,3-thiazol-2-yl}acetamide

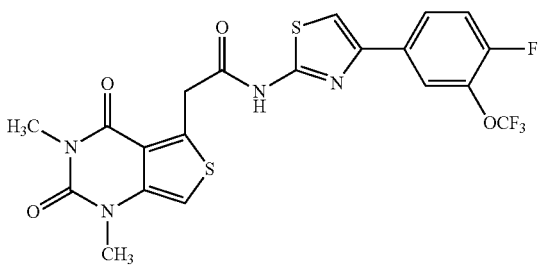

The title compound was prepared according to the general procedure (Method C) by coupling Intermediate 6 (150 mg, 0.531 mmol) with 4-[4-fluoro-3-(trifluoromethoxy)phenyl]-1,3-thiazol-2-amine (177 mg, 0.638 mmol) in the presence of sodium hydride (60% dispersion in mineral oil, 36 mg, 0.744 mmol) in dry toluene (6 ml) to give 55 mg of the product as an off-white solid; $^1$H NMR (300 MHz, DMSO-d$_6$) δ 3.19 (s, 3H), 3.39 (s, 3H), 4.55 (s, 2H), 7.03 (s, 1H), 7.59 (d, J=8.7 Hz, 1H), 7.80 (s, 1H), 8.00-8.05 (m, 2H), 12.63 (br s, 1H); APCI-MS (m/z) 513.12 (M−H)⁻.

Example 56

N-{4-[2,3-Difluoro-4-(trifluoromethyl)phenyl]-1,3-thiazol-2-yl}-2-(1,3-dimethyl-2,4-dioxo-1,2,3,4-tetrahydrothieno[3,4-d]pyrimidin-5-yl)acetamide

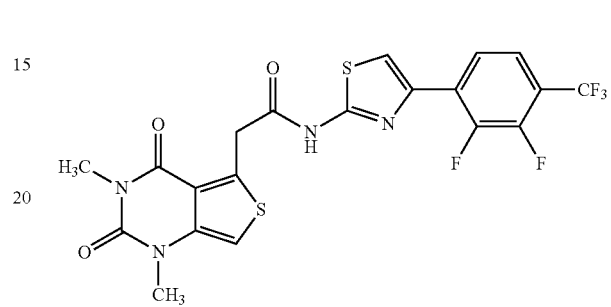

The title compound was prepared according to the general procedure (Method C) by coupling Intermediate 6 (150 mg, 0.531 mmol) with 4-[2,3-difluoro-4-(trifluoromethyl)phenyl]-1,3-thiazol-2-amine (179 mg, 0.638 mmol) in the presence of sodium hydride (60% dispersion in mineral oil, 43 mg, 1.062 mmol) in dry toluene (6 ml) to give 42 mg of the product as an off-white solid; $^1$H NMR (300 MHz, DMSO-d$_6$) δ 3.19 (s, 3H), 3.40 (s, 3H), 4.57 (s, 2H), 7.03 (s, 1H), 7.74 (t, J=7.5, 1H), 7.81 (s, 1H), 8.02 (d, J=6.6, 1H), 12.73 (br s, 1H); APCI-MS (m/z) 517.04 (M+H)⁺.

Example 57

N-{4-[2,4-Difluoro-3-(trifluoromethyl)phenyl]-1,3-thiazol-2-yl}-2-(1,3-dimethyl-2,4-dioxo-1,2,3,4-tetrahydrothieno[3,4-d]pyrimidin-5-yl)acetamide

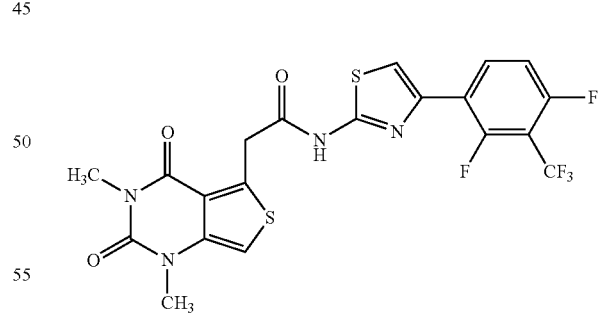

The title compound was prepared according to the general procedure (Method C) by coupling Intermediate 6 (150 mg, 0.531 mmol) with 4-[2,4-difluoro-3-(trifluoromethyl)phenyl]-1,3-thiazol-2-amine (179 mg, 0.638 mmol) in the presence of sodium hydride (60% dispersion in mineral oil, 43 mg, 1.062 mmol) in dry toluene (6 ml) to give 42 mg of the product as an off-white solid; $^1$H NMR (300 MHz, DMSO-d$_6$) δ 3.19 (s, 3H), 3.39 (s, 3H), 4.56 (s, 2H), 7.03 (s, 1H), 7.51

(t, J=9.0 Hz, 1H), 7.64 (s, 1H), 8.34 (q, J=6.9 Hz, 1H), 12.67 (br s, 1H); APCI-MS (m/z) 517.39 (M+H).

Example 58

N-{4-[3,5-difluoro-4-(trifluoromethyl)phenyl]-1,3-thiazol-2-yl}-2-(1,3-dimethyl-2,4-dioxo-1,2,3,4-tetrahydrothieno[3,4-d]pyrimidin-5-yl)acetamide

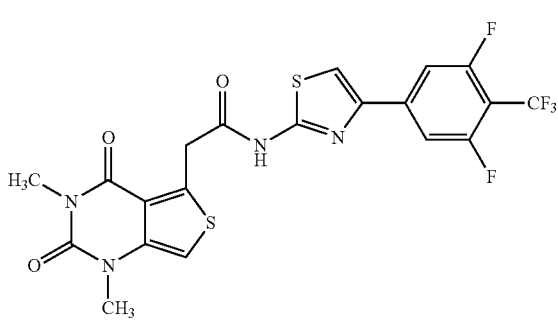 [SMILES: Cn1c(=O)c2c(CC(=O)Nc3nc(-c4cc(F)c(C(F)(F)F)c(F)c4)cs3)scc2n(C)c1=O]

The title compound was prepared according to the general procedure (Method C) by coupling Intermediate 6 (150 mg, 0.531 mmol) with 4-[3,5-difluoro-4-(trifluoromethyl)phenyl]-1,3-thiazol-2-amine (179 mg, 0.638 mmol) in the presence of sodium hydride (60% dispersion in mineral oil, 43 mg, 1.062 mmol) in dry toluene (6 ml) to give 40 mg of the product as an off-white solid; $^1$H NMR (300 MHz, DMSO-$d_6$) δ 3.19 (s, 3H), 3.39 (s, 3H), 4.56 (s, 2H), 7.03 (s, 1H), 7.83 (s, 1H), 7.87 (s, 1H), 8.09 (s, 1H), 12.70 (br s, 1H); APCI-MS (m/z) 517.04 (M+H)$^+$.

Example 59

N-{4-[4-(Difluoromethoxy)-3,5-difluorophenyl]-1,3-thiazol-2-yl}-2-(1,3-dimethyl-2,4-dioxo-1,2,3,4-tetrahydrothieno[3,4-d]pyrimidin-5-yl)acetamide

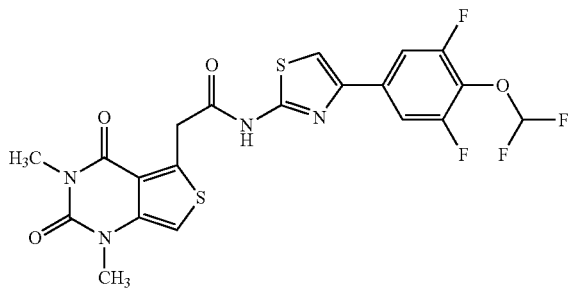 [SMILES: Cn1c(=O)c2c(CC(=O)Nc3nc(-c4cc(F)c(OC(F)F)c(F)c4)cs3)scc2n(C)c1=O]

The title compound was prepared according to the general procedure (Method C) by coupling Intermediate 6 (150 mg, 0.531 mmol) with 4-[4-(difluoromethoxy)-3,5-difluorophenyl]-1,3-thiazol-2-amine (176 mg, 0.638 mmol) in the presence of sodium hydride (60% dispersion in mineral oil, 43 mg, 1.062 mmol) in dry toluene (6 ml) to give 50 mg of the product as brown solid; $^1$H NMR (300 MHz, DMSO-$d_6$) δ 3.19 (s, 3H), 3.39 (s, 3H), 4.56 (s, 2H), 7.03 (s, 1H), 7.27 (t, J=73.8, 1H), 7.77 (s, 1H), 7.80 (s, 1H), 7.88 (s, 1H), 12.64 (br s, 1H); APCI-MS (m/z) 481.05 (M+H)$^+$.

Example 60

N-{4-[3,5-Difluoro-4-(2,2,2-difluoro-ethoxy)phenyl]-1,3-thiazol-2-yl}-2-(1,3-dimethyl-2,4-dioxo-1,2,3,4-tetrahydrothieno[3,4-d]pyrimidin-5-yl)acetamide

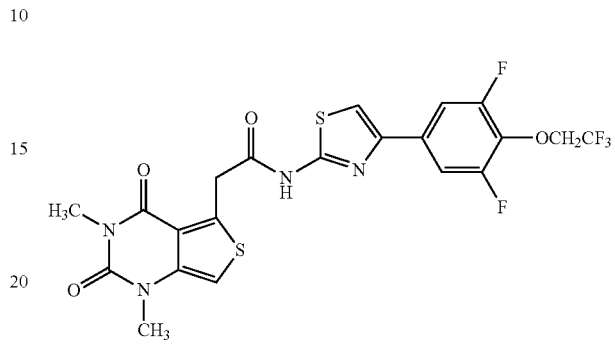

The title compound was prepared according to the general procedure (Method C) by coupling Intermediate 6 (150 mg, 0.531 mmol) with 4-[3,5-difluoro-4-(2,2,2-trifluoroethoxy)phenyl]-1,3-thiazol-2-amine (197 mg, 0.638 mmol) in the presence of sodium hydride (60% dispersion in mineral oil, 43 mg, 1.062 mmol) in dry toluene (6 ml) to give 45 mg of the product as an off-white solid; $^1$H NMR (300 MHz, DMSO-$d_6$) δ 3.22 (s, 3H), 3.45 (s, 3H), 4.61 (s, 2H), 4.91 (q, J=8.7 Hz, 2H), 7.08 (s, 1H), 7.76 (d, J=9.9 Hz, 2H), 7.86 (s, 1H), 12.66 (br s, 1H); APCI-MS (m/z) 547.17 (M+H)$^+$.

Pharmacological Activity

The illustrative examples of the present invention are screened for TRPA1 activity according to a modified procedure described in (a) Tóth, A. et al. Life Sciences, 2003, 73, 487-498. (b) McNamara C, R. et al, Proc. Natl. Acad. Sci. U.S.A., 2007, 104, 13525-13530. The screening of the compounds can be carried out by other methods and procedures known to persons skilled in the art.

Screening for TRPA1 Antagonist Using the $^{45}$Calcium Uptake Assay:

The inhibition of TRPA1 receptor activation was measured as inhibition of allyl isothiocyanate (AITC) induced cellular uptake of radioactive calcium.

Test compounds were dissolved in 100% DMSO to prepare 10 mM stock and then diluted using plain medium with 0.1% BSA and 1.8 mM $CaCl_2$ to get the desired concentration. The final concentration of DMSO in the reaction was 0.5% (v/v). Human TRPA1 expressing CHO cells were grown in F-12 DMEM medium with 10% FBS, 1% penicillin-streptomycin solution, and 400 g/ml of G-418. Rat TRPA1 expressing CHO cells were grown in F-12 DMEM medium with 10% FBS, 1% penicillin-streptomycin solution, and 400 µg/ml of Zeocin. Cells were seeded 24 h prior to the assay in 96 well plates so as to get ~50,000 cells per well on the day of experiment. Cells were treated with the test compounds for 10 minutes followed by the addition of AITC at a final concentration of 30 µM (for human TRPA1) and/or 10 µM (for rat TRPA1) and 5 µCi/ml $^{45}Ca^{+2}$ for 3 minutes. Cells were washed and lysed using a buffer containing 1% Triton X-100, 0.1% deoxycholate and 0.1% SDS. Radioactivity in the lysate was measured in a Packard TopCount after addition of liquid scintillant.

(Toth et al, *Life Sciences* (2003) 73, 487-498; McNamara C R et al, *Proceedings of the National Academy of Sciences*, (2007) 104, 13525-13530).

Concentration response curves were plotted as a % of maximal response obtained in the absence of test antagonist. $IC_{50}$ values can be calculated from concentration response curve by nonlinear regression analysis using GraphPad PRISM software.

The compounds prepared were tested using the above assay procedure and the results obtained are given in Table 2 and 3 for human and rat respectively. Percentage inhibition at concentrations of 1.0 μM and 10.0 μM are given in the tables along with $IC_{50}$ (nM) details for selected examples. The $IC_{50}$ (nM) values of the compounds are set forth in Table 2 and 3 wherein "A" refers to an $IC_{50}$ value of less than 50 nM, "B" refers to $IC_{50}$ value in range of 50.01 to 500.0 nM.

TABLE 2

In-vitro screening results (human) of compounds of invention

| Examples | Percentage inhibition at 1.0 μM | at 10.0 μM | Human $IC_{50}$ value (Range) |
|---|---|---|---|
| Example 1 | 13.22 | 45.97 | — |
| Example 2 | 98.95 | 98.83 | B |
| Example 3 | 88.95 | 98.49 | B |
| Example 4 | 29.07 | 99.47 | — |
| Example 5 | 95.27 | 99.86 | A |
| Example 6 | 100.0 | 100.0 | A |
| Example 7 | 80.36 | 99.80 | A |
| Example 8 | 89.82 | 99.91 | A |
| Example 9 | 99.16 | 98.42 | A |
| Example 10 | 98.22 | 99.45 | A |
| Example 11 | 98.63 | 97.11 | A |
| Example 12 | 99.73 | 99.82 | A |
| Example 13 | 98.20 | 98.09 | A |
| Example 14 | — | — | A |
| Example 15 | 60.05 | 96.77 | — |
| Example 16 | 99.12 | 99.11 | A |
| Example 17 | 97.52 | 98.77 | B |
| Example 18 | 98.55 | 100.00 | B |
| Example 19 | 95.03 | 98.18 | B |
| Example 20 | 98.97 | 99.58 | A |
| Example 21 | 95.42 | 100.00 | B |
| Example 22 | 89.80 | 100.00 | B |
| Example 23 | 97.67 | 99.01 | A |
| Example 24 | 98.49 | 99.93 | A |
| Example 25 | 98.54 | 98.80 | A |
| Example 26 | 100.00 | 100.00 | A |
| Example 27 | 93.22 | 99.13 | A |
| Example 28 | 10.03 | 46.83 | — |
| Example 29 | 91.66 | 97.99 | B |
| Example 30 | 88.92 | 98.44 | B |
| Example 31 | 98.03 | 98.46 | A |
| Example 32 | 99.23 | 99.28 | A |
| Example 33 | 96.94 | 96.89 | A |
| Example 34 | 97.40 | 98.42 | A |
| Example 35 | 99.14 | 99.96 | A |
| Example 36 | 98.90 | 99.78 | A |
| Example 37 | 99.01 | 97.73 | A |
| Example 38 | 25.04 | 87.93 | — |
| Example 39 | 47.83 | 78.58 | — |
| Example 40 | 99.86 | 100.0 | A |
| Example 41 | 0.0 | 0.0 | — |
| Example 42 | 9.74 | 74.57 | — |
| Example 43 | 30.51 | 4.42 | — |
| Example 44 | 91.40 | 93.23 | B |
| Example 45 | 93.98 | 98.89 | B |
| Example 46 | 93.89 | 98.51 | A |
| Example 47 | 97.89 | 98.79 | A |
| Example 48 | 95.48 | 98.89 | B |
| Example 49 | 95.96 | 99.84 | A |
| Example 50 | 99.49 | 100.00 | A |
| Example 51 | 96.93 | 99.71 | A |
| Example 52 | 97.98 | 94.44 | A |
| Example 53 | 97.77 | 99.28 | B |
| Example 54 | 95.09 | 99.69 | A |
| Example 55 | 99.59 | 99.80 | A |
| Example 56 | 94.42 | 99.46 | A |
| Example 57 | 96.92 | 91.02 | A |
| Example 58 | 84.93 | 95.78 | A |
| Example 59 | 89.33 | 91.42 | A |
| Example 60 | 97.99 | 97.42 | A |

TABLE 3

In-vitro screening results (rat) of compounds of invention

| Examples | Percentage inhibition at 1.0 μM | at 10.0 μM | Rat $IC_{50}$ value (Range) |
|---|---|---|---|
| Example 2 | 91.39 | 99.34 | — |
| Example 3 | 82.36 | 99.66 | — |
| Example 5 | — | — | A |
| Example 6 | 99.71 | 99.87 | B |
| Example 7 | 26.59 | 100.0 | — |
| Example 8 | 95.53 | 100.0 | B |
| Example 9 | 100.0 | 100.0 | B |
| Example 10 | 96.08 | 100.0 | B |
| Example 11 | 98.77 | 99.84 | A |
| Example 12 | 97.80 | 100.0 | B |
| Example 13 | — | — | A |
| Example 14 | — | — | A |
| Example 16 | 38.72 | 98.72 | — |
| Example 17 | 93.11 | 99.23 | B |
| Example 18 | 95.68 | 100.0 | — |
| Example 19 | 89.38 | 99.24 | — |
| Example 20 | 83.44 | 91.19 | B |
| Example 21 | 93.55 | 99.74 | — |
| Example 22 | 89.79 | 99.84 | — |
| Example 23 | 100.0 | 99.68 | B |
| Example 24 | 99.77 | 99.97 | B |
| Example 25 | 99.15 | 99.35 | B |
| Example 26 | 98.25 | 98.10 | B |
| Example 27 | 97.94 | 98.05 | B |
| Example 30 | 46.41 | 83.57 | — |
| Example 31 | 96.78 | 97.31 | B |
| Example 32 | 99.90 | 98.85 | A |
| Example 33 | 96.47 | 97.29 | B |
| Example 34 | 88.68 | 93.28 | B |
| Example 35 | 90.09 | 98.26 | B |
| Example 36 | 99.09 | 99.49 | B |
| Example 37 | 94.86 | 97.04 | A |
| Example 44 | 84.10 | 95.27 | — |
| Example 45 | 66.21 | 94.79 | — |
| Example 46 | 93.17 | 99.74 | B |
| Example 47 | 88.93 | 99.59 | — |
| Example 48 | 92.52 | 100.0 | — |
| Example 49 | 89.89 | 99.03 | B |
| Example 50 | 57.41 | 99.12 | — |
| Example 51 | 93.05 | 99.98 | B |
| Example 52 | 92.35 | 98.12 | B |
| Example 53 | 42.66 | 97.94 | — |
| Example 54 | 41.58 | 91.85 | — |
| Example 55 | 70.44 | 99.94 | — |
| Example 56 | 96.89 | 100.0 | B |
| Example 57 | 97.04 | 100.0 | A |
| Example 58 | 71.08 | 71.70 | — |
| Example 59 | 12.65 | 87.60 | — |
| Example 60 | 20.96 | 95.94 | — |

We claim:

1. A method for relieving the symptoms or inhibiting arresting or reducing a disease or condition associated with TRPA1 function in a subject in need thereof comprising administering to the subject an effective amount of a compound of the formula (I)

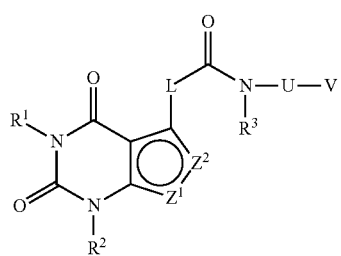

or a pharmaceutically acceptable salt thereof,
wherein,
- $R^1$ and $R^2$, which may be the same or different, are independently selected from hydrogen, substituted or unsubstituted alkyl, haloalkyl, alkenyl, alkynyl, cycloalkyl, cycloalkylalkyl, arylalkyl, $(CR^xR^y)_nOR^x$, $COR^x$, $COOR^x$, $CONR^xR^y$, and $(CH_2)$—$CHR^xR^y$;
- $R^3$ is selected from hydrogen, substituted or unsubstituted alkyl, alkenyl, alkynyl, cycloalkyl, cycloalkylalkyl, and cycloalkenyl;
- L is a linker selected from —$(CR^xR^y)_n$—, —O—$(CR^xR^y)_n$—, —C(O)—, —$NR^x$—, —$S(O)_mNR^x$—, —$NR^x(CR^xR^y)_n$— and —$S(O)_mNR^x(CR^xR^y)_n$;
- $Z^1$ and $Z^2$ are independently sulfur or $CR^a$; with a proviso that either of $Z^1$ or $Z^2$ is always sulfur;
- $R^a$ is selected from hydrogen, cyano, halogen, substituted or unsubstituted alkyl, haloalkyl, alkenyl, alkynyl, cycloalkyl, cycloalkylalkyl, $OR^x$, $(CR^xR^y)_nOR^x$, $COR^x$, $COOR^x$, $CONR^xR^y$, $S(O)_mNR^xR^y$, $NR^xR^y$, $NR^x(CR^xR^y)_nOR^x$, $(CH_2)_nNR^xR^y$, $(CH_2)_nCHR^xR^y$, $NR^x(CR^xR^y)_nCONR^xR^y$, $(CH_2)_nNHCOR^x$, $(CH_2)_nNH(CH_2)_nSO_2R^x$, $(CH_2)_nNHSO_2R^x$, $SR^x$ and $OR^x$;
- U is selected from substituted or unsubstituted aryl, substituted or unsubstituted five membered heterocycles selected from the group consisting of thiazole, isothiazole, oxazole, isoxazole, thiadiazole, oxadiazole, pyrazole, imidazole, furan, thiophene, pyrrole, 1,2,3-triazole, and 1,2,4-triazole, or substituted or unsubstituted six membered heterocycle selected from the group consisting of pyrimidine, pyridine and pyridazine;
- V is selected from hydrogen, cyano, nitro, —$NR^xR^y$, halogen, hydroxyl, substituted or unsubstituted alkyl, alkenyl, alkynyl, cycloalkyl, cycloalkylalkyl, cycloalkenyl, haloalkyl, haloalkoxy, cycloalkylalkoxy, aryl, arylalkyl, biaryl, heteroaryl, heteroarylalkyl, heterocyclic ring and heterocyclylalkyl, —$C(O)OR^x$, —$OR^x$, —$C(O)NR^xR^y$, —$C(O)R^x$, and —$SO_2NR^xR^y$; or U and V together may form an optionally substituted 3 to 7 membered saturated or unsaturated cyclic ring that may optionally include one or more heteroatoms selected from O, S and N;
- at each occurrence, $R^x$ and $R^y$ are independently selected from hydrogen, hydroxyl, halogen, substituted or unsubstituted alkyl, alkenyl, alkynyl, cycloalkyl, cycloalkylalkyl, cycloalkenyl, aryl, arylalkyl, heteroaryl, heteroarylalkyl, heterocyclic ring and heterocyclylalkyl; and
- at each occurrence, 'm' and 'n' are independently selected from 0 to 2, both inclusive;

wherein the disease or condition is selected from pain, complex regional pain syndrome, postoperative pain, rheumatoid arthritic pain, back pain, visceral pain, cancer pain, algesia, neuralgia, migraine, neuropathies, diabetic neuropathy, sciatica, HIV-related neuropathy, post-herpetic neuralgia, fibromyalgia, nerve injury, ischaemia, neurodegeneration, stroke, post stroke pain, multiple sclerosis, respiratory diseases, cough, inflammatory disorders, oesophagitis, gastroeosophagal reflux disorder (GERD), irritable bowel syndrome, inflammatory bowel disease, pelvic hypersensitivity, urinary incontinence, cystitis, burns, psoriasis, eczema, emesis, stomach duodenal ulcer and pruritus.

2. The method according to claim 1, wherein L is $CH_2$.

3. The method according to claim 1, wherein $R^1$ and $R^2$ are $(C_1-C_4)$alkyl.

4. The method according to claim 3, wherein $(C_1-C_4)$alkyl is methyl.

5. The method according to claim 1, wherein $R^3$ is hydrogen.

6. The method according to claim 1, wherein U is thiazole, imidazole, isoxazole, pyrazole, thiadiazole or pyrimidine.

7. The method according to claim 1, wherein V is aryl.

8. The method according to claim 7, wherein aryl is phenyl.

9. The method according to claim 1 wherein the compound is

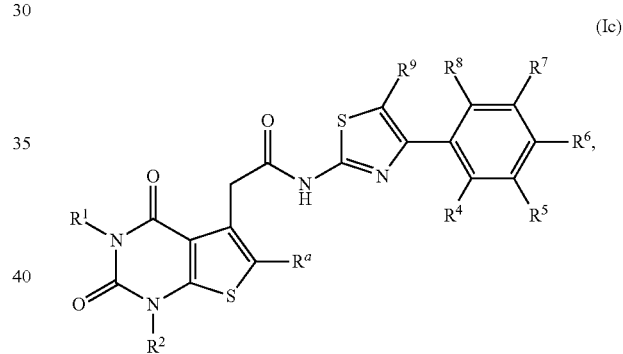

or a pharmaceutically acceptable salt thereof,
wherein $R^1$, $R^2$ and $R^a$, which may be the same or different, are each independently hydrogen or $(C_1-C_4)$alkyl;
$R^4$, $R^5$, $R^6$, $R^7$, $R^8$ and $R^9$, which may be same or different, are each independently selected from the group comprising of hydrogen, halogen, cyano, hydroxyl, nitro, amino, substituted or unsubstituted alkyl, alkoxy, haloalkyl, haloalkoxy, cycloalkyl, cycloalkylalkyl, cycloalkenyl, cycloalkylalkoxy, aryl, arylalkyl, biaryl, heteroaryl, heteroarylalkyl, heterocyclic ring and heterocyclylalkyl.

10. The method according to claim 9, wherein $R^1$ and $R^2$ are methyl.

11. The method according to claim 9, wherein $R^4$, $R^5$, $R^6$ and $R^7$ are independently selected from the group consisting of hydrogen, fluoro, trifluoromethyl or trifluoromethoxy.

12. The method according to claim 9, wherein $R^8$ and $R^9$ are hydrogen.

13. The method according to claim 1 wherein compound is selected from:
2-(1,3-Dimethyl-2,4-dioxo-1,2,3,4-tetrahydrothieno[2,3-d]pyrimidin-5-yl)-N-[4-(trifluoromethyl)-1,3-thiazol-2-yl]acetamide;

N-[4-(4-Chlorophenyl)-1,3-thiazol-2-yl]-2-(1,3-dimethyl-2,4-dioxo-1,2,3,4-tetrahydrothieno[2,3-d]pyrimidin-5-yl)acetamide;
2-(1,3-Dimethyl-2,4-dioxo-1,2,3,4-tetrahydrothieno[2,3-d]pyrimidin-5-yl)-N-{4-[3-(trifluoromethoxy)phenyl]-1,3-thiazol-2-yl}acetamide;
2-(1,3-Dimethyl-2,4-dioxo-1,2,3,4-tetrahydrothieno[2,3-d]pyrimidin-5-yl)-N-[4-(4-isobutylphenyl)-1,3-thiazol-2-yl]acetamide;
2-(1,3-Dimethyl-2,4-dioxo-1,2,3,4-tetrahydrothieno[2,3-d]pyrimidin-5-yl)-N-{4-[3-fluoro-4-(trifluoromethyl)phenyl]-1,3-thiazol-2-yl}acetamide;
2-(1,3-Dimethyl-2,4-dioxo-1,2,3,4-tetrahydrothieno[2,3-d]pyrimidin-5-yl)-N-{4-[4-fluoro-3-(trifluoromethyl)phenyl]-1,3-thiazol-2-yl}acetamide;
2-(1,3-Dimethyl-2,4-dioxo-1,2,3,4-tetrahydrothieno[2,3-d]pyrimidin-5-yl)-N-{4-[2-fluoro-4-(trifluoromethyl)phenyl]-1,3-thiazol-2-yl}acetamide;
2-(1,3-Dimethyl-2,4-dioxo-1,2,3,4-tetrahydrothieno[2,3-d]pyrimidin-5-yl)-N-{4-[3-fluoro-5-(trifluoromethyl)phenyl]-1,3-thiazol-2-yl}acetamide;
2-(1,3-Dimethyl-2,4-dioxo-1,2,3,4-tetrahydrothieno[2,3-d]pyrimidin-5-yl)-N-{4-[2-fluoro-3-(trifluoromethyl)phenyl]-1,3-thiazol-2-yl}acetamide;
2-(1,3-Dimethyl-2,4-dioxo-1,2,3,4-tetrahydrothieno[2,3-d]pyrimidin-5-yl)-N-{4-[4-fluoro-3-(trifluoromethoxy)phenyl]-1,3-thiazol-2-yl}acetamide;
2-(1,3-Dimethyl-2,4-dioxo-1,2,3,4-tetrahydrothieno[2,3-d]pyrimidin-5-yl)-N-{4-[3-fluoro-4-(trifluoromethoxy)phenyl]-1,3-thiazol-2-yl}acetamide;
N-[4-(3,4-Dichlorophenyl)-1,3-thiazol-2-yl]-2-(1,3-dimethyl-2,4-dioxo-1,2,3,4-tetrahydrothieno[2,3-d]pyrimidin-5-yl)acetamide;
N-{4-[2,4-Difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide;
[N-{4-[2,4-Difluoro-3-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide]sodium;
N-{4-[2,3-Difluoro-4-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide;
N-{4-[3,5-Difluoro-4-(trifluoromethyl)phenyl]-1,3-thiazol-2-yl}-2-(1,3-dimethyl-2,4-dioxo-1,2,3,4-tetrahydrothieno[2,3-d]pyrimidin-5-yl)acetamide;
N-[4-(4-tert-Butylphenyl)-1,3-thiazol-2-yl]-2-(1,3,6-trimethyl-2,4-dioxo-1,2,3,4-tetrahydrothieno[2,3-d]pyrimidin-5-yl)acetamide;
N-{4-[3-(Trifluoromethoxy)phenyl]-1,3-thiazol-2-yl}-2-(1,3,6-trimethyl-2,4-dioxo-1,2,3,4-tetrahydrothieno[2,3-d]pyrimidin-5-yl)acetamide;
N-[4-(4-Chlorophenyl)-1,3-thiazol-2-yl]-2-(1,3,6-trimethyl-2,4-dioxo-1,2,3,4-tetrahydrothieno[2,3-d]pyrimidin-5-yl)acetamide;
N-[4-(3,4-Dichlorophenyl)-1,3-thiazol-2-yl]-2-(1,3,6-trimethyl-2,4-dioxo-1,2,3,4-tetrahydrothieno[2,3-d]pyrimidin-5-yl)acetamide;
N-[4-(2,3-Difluorophenyl)-1,3-thiazol-2-yl]-2-(1,3,6-trimethyl-2,4-dioxo-1,2,3,4-tetrahydrothieno[2,3-d]pyrimidin-5-yl)acetamide;
N-[4-(2,4-Difluorophenyl)-1,3-thiazol-2-yl]-2-(1,3,6-trimethyl-2,4-dioxo-1,2,3,4-tetrahydrothieno[2,3-d]pyrimidin-5-yl)acetamide;
N-{4-[4-Fluoro-3-(trifluoromethyl)phenyl]-1,3-thiazol-2-yl}-2-(1,3,6-trimethyl-2,4-dioxo-1,2,3,4-tetrahydrothieno[2,3-d]pyrimidin-5-yl)acetamide;
N-{4-[3-Fluoro-4-(trifluoromethyl)phenyl]-1,3-thiazol-2-yl}-2-(1,3,6-trimethyl-2,4-dioxo-1,2,3,4-tetrahydrothieno[2,3-d]pyrimidin-5-yl)acetamide;
N-{4-[4-Fluoro-3-(trifluoromethoxy)phenyl]-1,3-thiazol-2-yl}-2-(1,3,6-trimethyl-2,4-dioxo-1,2,3,4-tetrahydrothieno[2,3-d]pyrimidin-5-yl)acetamide;
N-{4-[3-Fluoro-4-(trifluoromethoxy)phenyl]-1,3-thiazol-2-yl}-2-(1,3,6-trimethyl-2,4-dioxo-1,2,3,4-tetrahydrothieno[2,3-d]pyrimidin-5-yl)acetamide;
N-{4-[2,4-Difluoro-3-(trifluoromethyl)phenyl]-1,3-thiazol-2-yl}-2-(1,3,6-trimethyl-2,4-dioxo-1,2,3,4-tetrahydrothieno[2,3-d]pyrimidin-5-yl)acetamide;
N-[4-(3-Trifluoromethoxyphenyl)-1H-imidazol-2-yl]-2-(1,3,6-trimethyl-2,4-dioxo-1,2,3,4-tetrahydrothieno[2,3-d]pyrimidin-5-yl)acetamide;
N-{4-[3-Fluoro-4-(trifluoromethyl)phenyl]-1H-imidazol-2-yl}-2-(1,3,6-trimethyl-2,4-dioxo-1,2,3,4-tetrahydrothieno[2,3-d]pyrimidin-5-yl)acetamide;
N-[4-(4-Cyanophenyl)-1,3-thiazol-2-yl]-2-(6-ethyl-1,3-dimethyl-2,4-dioxo-1,2,3,4-tetrahydrothieno[2,3-d]pyrimidin-5-yl)acetamide;
N-{4-[3-Fluoro-4-(trifluoromethyl)phenyl]-1,3-thiazol-2-yl}-2-(6-ethyl-1,3-dimethyl-2,4-dioxo-1,2,3,4-tetrahydrothieno[2,3-d]pyrimidin-5-yl)acetamide;
N-[4-(2,4-Difluoro-3-trifluoromethyl)phenyl)-1,3-thiazol-2-yl]-2-(6-ethyl-1,3-dimethyl-2,4-dioxo-1,2,3,4-tetrahydrothieno[2,3-d]pyrimidin-5-yl)acetamide;
N-{4-[4-(Difluoromethoxy)-3,5-difluorophenyl]-1,3-thiazol-2-yl}-2-(6-ethyl-1,3-dimethyl-2,4-dioxo-1,2,3,4-tetrahydrothieno[2,3-d]pyrimidin-5-yl)acetamide;
N-{4-[3,5-Difluoro-4-(2,2,2-trifluoroethoxyl)phenyl]-1,3-thiazol-2-yl}-2-(6-ethyl-1,3-dimethyl-2,4-dioxo-1,2,3,4-tetrahydrothieno[2,3-d]pyrimidin-5-yl)acetamide;
N-{4-[3-Fluoro-4-(trifluoromethyl)phenyl]-1,3-thiazol-2-yl}-2-(1,3-dimethyl-2,4-dioxo-6-propyl-1,2,3,4-tetrahydrothieno[2,3-d]pyrimidin-5-yl) acetamide;
N-{4-[Difluoromethoxy-3,5-difluorophenyl]-1,3-thiazol-2-yl}-2-(1,3-dimethyl-2,4-dioxo-6-propyl-1,2,3,4-tetrahydrothieno[2,3-d]pyrimidin-5-yl) acetamide;
N-{4-[3-Fluoro-4-(trifluoromethyl)phenyl]-1,3-thiazol-2-yl}-2-(6-isopropyl-1,3-dimethyl-2,4-dioxo-1,2,3,4-tetrahydrothieno[2,3-d]pyrimidin-5-yl)acetamide;
N-[3-(4-Chlorophenyl)isoxazol-5-yl]-2-(1,3-dimethyl-2,4-dioxo-1,2,3,4-tetrahydrothieno[2,3-d]pyrimidin-5-yl)acetamide;
N-[5-(4-Bromophenyl)isoxazol-3-yl]-2-(1,3-dimethyl-2,4-dioxo-1,2,3,4-tetrahydrothieno[2,3-d]pyrimidin-5-yl)acetamide;
N-[1-(4-Bromophenyl)-1H-pyrazol-3-yl]-2-(1,3-dimethyl-2,4-dioxo-1,2,3,4-tetrahydrothieno[2,3-d]pyrimidin-5-yl)acetamide;
N-[3-(4-Chlorophenyl)-1H-pyrazol-5-yl]-2-(1,3-dimethyl-2,4-dioxo-1,2,3,4-tetrahydrothieno[3,4-d]pyrimidin-5-yl)acetamide;
N-[5-(4-Bromophenyl)-1,3,4-thiadiazol-2-yl]-2-(1,3-dimethyl-2,4-dioxo-1,2,3,4-tetrahydrothieno[2,3-d]pyrimidin-5-yl)acetamide;
N-[4-(4-Bromophenyl)pyrimidin-2-yl]-2-(1,3-dimethyl-2,4-dioxo-1,2,3,4-tetrahydrothieno[2,3-d]pyrimidin-5-yl)acetamide;
2-(1,3-Dimethyl-2,4-dioxo-1,2,3,4-tetrahydrothieno[3,4-d]pyrimidin-5-yl)-N-[4-(4-isobutylphenyl)-1,3-thiazol-2-yl]acetamide;
N-[4-(4-Chlorophenyl)-1,3-thiazol-2-yl]-2-(1,3-dimethyl-2,4-dioxo-1,2,3,4-tetrahydrothieno[3,4-d]pyrimidin-5-yl)acetamide;

2-(1,3-Dimethyl-2,4-dioxo-1,2,3,4-tetrahydrothieno[3,4-d]pyrimidin-5-yl)-N-[4-(3-trifluoromethyl)phenyl]-1,3-thiazol-2-yl]acetamide;

2-(1,3-Dimethyl-2,4-dioxo-1,2,3,4-tetrahydrothieno[3,4-d]pyrimidin-5-yl)-N-[4-(4-trifluoromethyl)phenyl]-1,3-thiazol-2-yl]acetamide;

2-(1,3-Dimethyl-2,4-dioxo-1,2,3,4-tetrahydrothieno[3,4-d]pyrimidin-5-yl)-N-{4-[3-(trifluoromethoxy)phenyl]-1,3-thiazol-2-yl}acetamide;

2-(1,3-Dimethyl-2,4-dioxo-1,2,3,4-tetrahydrothieno[3,4-d]pyrimidin-5-yl)-N-{4-[4-fluoro-3-(trifluoromethyl)phenyl]-1,3-thiazol-2-yl}acetamide;

2-(1,3-Dimethyl-2,4-dioxo-1,2,3,4-tetrahydrothieno[3,4-d]pyrimidin-5-yl)-N-{4-[3-fluoro-4-(trifluoromethyl)phenyl]-1,3-thiazol-2-yl}acetamide;

2-(1,3-Dimethyl-2,4-dioxo-1,2,3,4-tetrahydrothieno[3,4-d]pyrimidin-5-yl)-N-{4-[2-fluoro-4-(trifluoromethyl)phenyl]-1,3-thiazol-2-yl}acetamide;

2-(1,3-Dimethyl-2,4-dioxo-1,2,3,4-tetrahydrothieno[3,4-d]pyrimidin-5-yl)-N-{4-[3-fluoro-4-(trifluoromethoxy)phenyl]-1,3-thiazol-2-yl}acetamide;

N-[4-(3,4-Dichlorophenyl)-1,3-thiazol-2-yl]-2-(1,3-dimethyl-2,4-dioxo-1,2,3,4-tetrahydrothieno[3,4-d]pyrimidin-5-yl)acetamide;

2-(1,3-Dimethyl-2,4-dioxo-1,2,3,4-tetrahydrothieno[3,4-d]pyrimidin-5-yl)-N-{4-[3-fluoro-5-(trifluoromethyl)phenyl]-1,3-thiazol-2-yl}acetamide;

2-(1,3-Dimethyl-2,4-dioxo-1,2,3,4-tetrahydrothieno[3,4-d]pyrimidin-5-yl)-N-{4-[4-fluoro-3-(trifluoromethoxy)phenyl]-1,3-thiazol-2-yl}acetamide;

N-{4-[2,3-Difluoro-4-(trifluoromethyl)phenyl]-1,3-thiazol-2-yl}-2-(1,3-dimethyl-2,4-dioxo-1,2,3,4-tetrahydrothieno[3,4-d]pyrimidin-5-yl)acetamide;

N-{4-[2,4-Difluoro-3-(trifluoromethyl)phenyl]-1,3-thiazol-2-yl}-2-(1,3-dimethyl-2,4-dioxo-1,2,3,4-tetrahydrothieno[3,4-d]pyrimidin-5-yl)acetamide;

N-{4-[3,5-difluoro-4-(trifluoromethyl)phenyl]-1,3-thiazol-2-yl}-dimethyl-2,4-dioxo-1,2,3,4-tetrahydrothieno[3,4-d]pyrimidin-5-yl)acetamide;

N-{4-[4-(Difluoromethoxy)-3,5-difluorophenyl]-1,3-thiazol-2-yl}-dimethyl-2,4-dioxo-1,2,3,4-tetrahydrothieno[3,4-d]pyrimidin-5-yl)acetamide; and N-{4-[3,5-Difluoro-4-(2,2,2-trifluoro-ethoxy)phenyl]-1,3-thiazol-2-yl}-2-(1,3-dimethyl-2,4-dioxo-1,2,3,4-tetrahydrothieno[3,4-d]pyrimidin-5-yl)acetamide;

or a pharmaceutically acceptable salt thereof.

14. The method according to claim 1 wherein the compound is

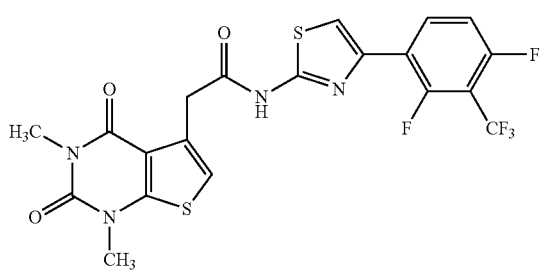 [SMILES: Cn1c(=O)c2c(CC(=O)Nc3nc(-c4ccc(F)c(C(F)(F)F)c4F)cs3)csc2n(C)c1=O]

or a pharmaceutically acceptable salt thereof and the disease or condition is pain.

15. The method according to claim 1 wherein the compound is

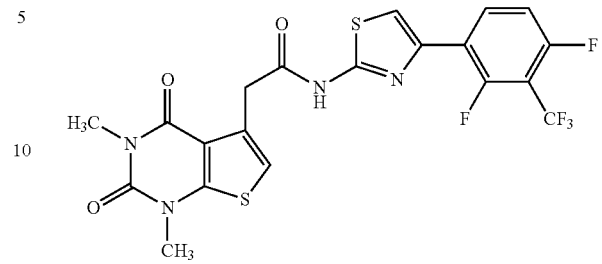

or a pharmaceutically acceptable salt thereof and the disease or condition is cough.

16. A process for preparing a compound of formula (Ic):

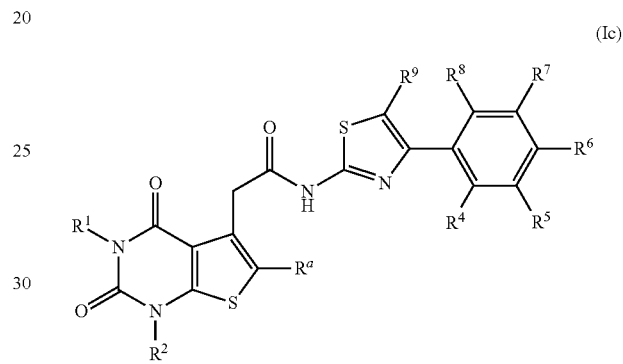

or a pharmaceutically acceptable salt thereof, which comprises reacting a compound of formula (25) with amine compound of formula (46)

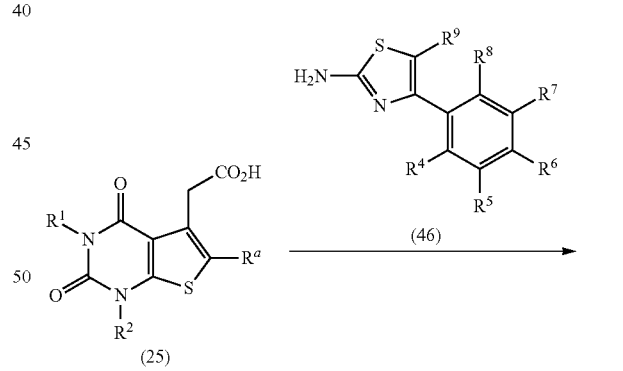

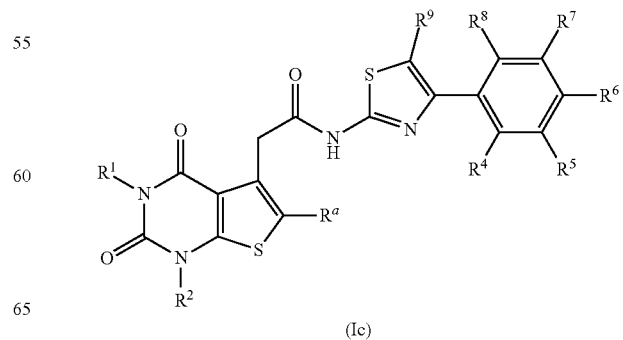

wherein,

R¹, R² and Rᵃ, which may be the same or different, are each independently hydrogen or (C₁-C₄)alkyl;

R⁴, R⁵, R⁶, R⁷, R⁸ and R⁹, which may be same or different, are each independently selected from the group comprising of hydrogen, halogen, cyano, hydroxyl, nitro, amino, substituted or unsubstituted alkyl, alkoxy, haloalkyl, haloalkoxy, cycloalkyl, cycloalkylalkyl, cycloalkenyl, cycloalkylalkoxy, aryl, arylalkyl, biaryl, heteroaryl, heteroarylalkyl, heterocyclic ring and heterocyclylalkyl.

17. The process according to claim 16, wherein R¹ and R² are methyl and Rᵃ is hydrogen.

18. The process according to claim 16, wherein R⁴, R⁵, R⁶ and R⁷ are independently selected from hydrogen, fluoro, trifluoromethyl and trifluoromethoxy.

19. The process according to claim 16, wherein R⁸ and R⁹ are hydrogen.

20. The process according to claim 16, wherein compound of formula (25) is reacted with amine compound of formula (46) in the presence of coupling agent.

21. The process of claim 20, wherein the coupling agent is 1-ethyl-3-(3-dimethylaminopropyl)carbodiimide hydrochloride and hydroxybenzotriazole.

22. The process according to claim 16, wherein compound of formula (25) is reacted with amine compound of formula (46) in the presence of base.

23. The process according to claim 22 wherein the base is 4-dimethylaminopyridine, triethylamine or N-methyl morpholine.

24. A process for preparing compound of formula (II)

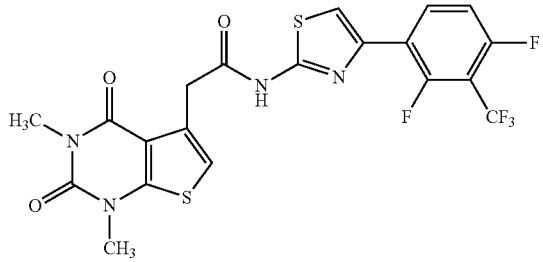 [SMILES: Cn1c(=O)c2c(CC(=O)Nc3nc(-c4ccc(F)c(C(F)(F)F)c4F)cs3)csc2n(C)c1=O]

(II)

or a pharmaceutically acceptable salt thereof, which comprises reacting intermediate 1 with 4-[2,4-difluoro-3-(trifluoromethyl)phenyl]-1,3-thiazol-2-amine

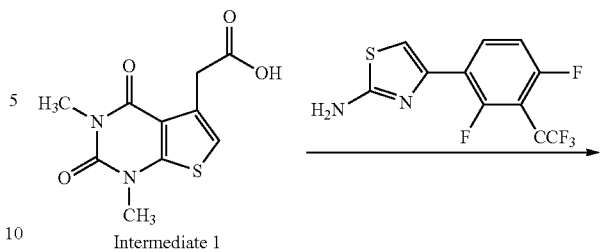

Intermediate 1

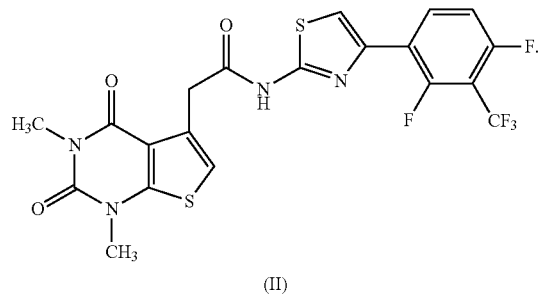

(II)

25. The process according to claim 24, wherein intermediate 1 is reacted with 4-[2,4-difluoro-3-(trifluoromethyl)phenyl]-1,3-thiazol-2-amine in the presence of coupling agent.

26. The process of claim 25, wherein the coupling agent is 1-ethyl-3-(3-dimethylaminopropyl)carbodiimide hydrochloride and hydroxybenzotriazole.

27. The process according to claim 24, wherein intermediate 1 is reacted with 4-[2,4-difluoro-3-(trifluoromethyl)phenyl]-1,3-thiazol-2-amine in the presence of base.

28. The process of claim 27, wherein the base is 4-dimethylaminopyridine, triethylamine or N-methyl morpholine.

29. The method according to claim 1 wherein the compound is

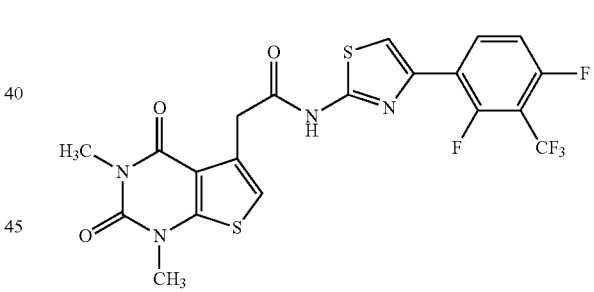

or a pharmaceutically acceptable salt thereof and the disease or condition is diabetic neuropathy.

* * * * *